(12) United States Patent
Fagg, IV et al.

(10) Patent No.: US 11,344,583 B2
(45) Date of Patent: *May 31, 2022

(54) COMPOSITIONS CONTAINING AMNIOTIC COMPONENTS AND METHODS FOR PREPARATION AND USE THEREOF

(71) Applicant: Merakris Therapeutics Inc., Research Triangle Park, NC (US)

(72) Inventors: William Samuel Fagg, IV, Galveston, TX (US); Thomas Christopher Broderick, Hillsborough, NC (US)

(73) Assignee: Merakris Therapeutics Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/288,809

(22) Filed: Feb. 28, 2019

(65) Prior Publication Data

US 2019/0300848 A1   Oct. 3, 2019

Related U.S. Application Data

(63) Continuation-in-part of application No. PCT/US2018/047818, filed on Aug. 23, 2018.

(60) Provisional application No. 62/549,076, filed on Aug. 23, 2017.

(51) Int. Cl.

| | |
|---|---|
| *A61K 35/50* | (2015.01) |
| *A61P 17/02* | (2006.01) |
| *A01N 1/02* | (2006.01) |
| *A61K 8/67* | (2006.01) |
| *A61K 8/98* | (2006.01) |
| *A61K 9/00* | (2006.01) |
| *A61K 31/355* | (2006.01) |
| *A61K 31/455* | (2006.01) |
| *A61K 35/51* | (2015.01) |
| *A61L 27/36* | (2006.01) |
| *A61L 27/54* | (2006.01) |
| *A61Q 19/00* | (2006.01) |
| *A61Q 19/08* | (2006.01) |
| *C12N 5/073* | (2010.01) |
| *C12N 5/0775* | (2010.01) |
| *A61K 8/99* | (2017.01) |
| *A01N 63/10* | (2020.01) |

(52) U.S. Cl.
CPC ............ *A61K 35/50* (2013.01); *A01N 1/0226* (2013.01); *A01N 63/10* (2020.01); *A61K 8/675* (2013.01); *A61K 8/678* (2013.01); *A61K 8/982* (2013.01); *A61K 8/99* (2013.01); *A61K 9/0014* (2013.01); *A61K 31/355* (2013.01); *A61K 31/455* (2013.01); *A61K 35/51* (2013.01); *A61L 27/3604* (2013.01); *A61L 27/3683* (2013.01); *A61L 27/54* (2013.01); *A61P 17/02* (2018.01); *A61Q 19/00* (2013.01); *A61Q 19/007* (2013.01); *A61Q 19/08* (2013.01); *C12N 5/0605* (2013.01); *C12N 5/0665* (2013.01); *A61K 2800/10* (2013.01); *A61K 2800/522* (2013.01); *A61K 2800/805* (2013.01); *C12N 2501/999* (2013.01); *C12N 2506/025* (2013.01)

(58) Field of Classification Search
CPC ............... C12N 5/0605; C12N 5/0665; C12N 2501/999; C12N 2506/025; A61K 8/99; A61K 8/675; A61K 8/678; A61K 8/982; A61K 9/0014; A61K 31/355; A61K 31/455; A61K 35/50; A61K 35/51; A61P 17/02; A01N 1/0226; A01N 63/00; A61L 27/3604; A61L 27/3683; A61L 27/54; A61Q 19/00; A61Q 19/007; A61Q 19/08

See application file for complete search history.

(56) References Cited

U.S. PATENT DOCUMENTS

| | | | |
|---|---|---|---|
| 4,496,086 | A | 1/1985 | Duchadeau |
| 4,798,824 | A | 1/1989 | Belzer et al. |
| 5,152,456 | A | 10/1992 | Ross et al. |
| 5,261,601 | A | 11/1993 | Ross et al. |
| 5,280,784 | A | 1/1994 | Kohler |
| 5,309,900 | A | 5/1994 | Knoch et al. |

(Continued)

FOREIGN PATENT DOCUMENTS

| | | | |
|---|---|---|---|
| CN | 105039244 A | * | 11/2015 |
| WO | 2008/036447 A2 | | 3/2008 |

(Continued)

OTHER PUBLICATIONS

Rouiller et al. "A high-throughput media design approach for high performance mammalian fed-batch cultures." MAbs. May-Jun. 2013;5(3):501-11 (Year: 2013).*

(Continued)

*Primary Examiner* — Titilayo Moloye
(74) *Attorney, Agent, or Firm* — McCarter & English, LLP; Beverly W. Lubit

(57) ABSTRACT

Compositions are provided that contain biologically active components of amniotic fluid including growth factors and other proteins, carbohydrates, lipids, and metabolites. The compositions containing biologically active components of amniotic fluid can be useful for a range of therapeutic treatments including joint and soft tissue repair, regulation of skin condition, and for use in organ preservation, such as for use in organ transplant procedures. Advantages of the compositions include that they can be reproducibly produced, without the inherent variability of amniotic fluid from individual donors, and that they are free of fetal waste.

11 Claims, 25 Drawing Sheets

(56) References Cited

U.S. PATENT DOCUMENTS

| | | | |
|---|---|---|---|
| 5,312,046 | A | 5/1994 | Knoch et al. |
| 5,458,136 | A | 10/1995 | Jaser et al. |
| 5,461,695 | A | 10/1995 | Knoch |
| 5,518,179 | A | 5/1996 | Humberstone et al. |
| 5,549,102 | A | 8/1996 | Lintl et al. |
| 5,552,267 | A | 9/1996 | Stern et al. |
| 5,740,966 | A | 4/1998 | Blaha-Schnabel |
| 5,957,389 | A | 9/1999 | Wunderlich et al. |
| 6,000,394 | A | 12/1999 | Blaha-Schnabel et al. |
| 6,085,741 | A | 7/2000 | Becker |
| 6,106,479 | A | 8/2000 | Wunderlich et al. |
| 6,176,237 | B1 | 1/2001 | Wunderlich et al. |
| 6,513,519 | B2 | 2/2003 | Gallem |
| 6,513,727 | B1 | 2/2003 | Jaser et al. |
| 6,962,151 | B1 | 11/2005 | Knoch et al. |
| 6,983,747 | B2 | 1/2006 | Gallem et al. |
| 7,059,320 | B2 | 6/2006 | Feiner et al. |
| 7,252,085 | B2 | 8/2007 | Kunschir |
| 8,551,538 | B2 | 10/2013 | Qian |
| 9,132,156 | B1 | 9/2015 | Werber et al. |
| 9,220,631 | B2 | 12/2015 | Sigg et al. |
| 9,579,350 | B1 | 2/2017 | Harrell |
| 2001/0003586 | A1 | 6/2001 | Vatter et al. |
| 2003/0211604 | A1 | 11/2003 | E. Brown |
| 2004/0081681 | A1 | 4/2004 | Vromen |
| 2005/0118712 | A1 | 6/2005 | Tsai et al. |
| 2007/0207127 | A1 | 9/2007 | Kato et al. |
| 2007/0292401 | A1 | 12/2007 | Harmon et al. |
| 2010/0317104 | A1 | 12/2010 | Elefanty et al. |
| 2012/0141399 | A1* | 6/2012 | You .................. A61Q 17/04 424/62 |
| 2013/0183387 | A1* | 7/2013 | Palladino ............ A61K 31/56 424/582 |
| 2014/0050706 | A1 | 2/2014 | Shroff |
| 2014/0336600 | A1 | 11/2014 | Harrell |
| 2015/0050251 | A1 | 2/2015 | Trumpower et al. |
| 2015/0140114 | A1 | 5/2015 | Sasko |
| 2016/0022744 | A1 | 1/2016 | Burt |
| 2016/0287752 | A1 | 10/2016 | Britt |
| 2016/0310534 | A1 | 10/2016 | Chang et al. |
| 2016/0375064 | A1 | 12/2016 | Beaudry et al. |
| 2017/0042943 | A1 | 2/2017 | Namin et al. |
| 2018/0000869 | A1 | 1/2018 | Britt |
| 2019/0300848 | A1 | 10/2019 | Fagg, IV et al. |

FOREIGN PATENT DOCUMENTS

| | | | |
|---|---|---|---|
| WO | 2013/082487 | A1 | 6/2013 |
| WO | 2017/003954 | A1 | 1/2017 |
| WO | 2017023690 | A1 | 2/2017 |

OTHER PUBLICATIONS

Rathbone et al. "Effect of various concentrations of antibiotics on osteogenic cell viability and activity." J Orthop Res. Jul. 2011;29(7):1070-4. (Year: 2011).*

Souza et al. "Effect of amikacin, cephalothin, clindamycin and vancomycin on in vitro fibroblast growth." Genetics and Molecular Biology [online]. 2004, v. 27, n. 3 [Accessed May 31, 2021], pp. 454-459. (Year: 2004).*

Wang Y. Wnt/Planar cell polarity signaling: A new paradigm for cancer therapy. Mol Cancer Ther, 2009; 8(8):2103-2109.

Wei, C. J., et al. Connexins and cell signaling development and disease. (2004) Annu Rev Cell Dev Biol 20, 811-38.

Welch, M. et al., Temporal relationships of F-actin bundle formation, collagen and fibronectin matrix assembly, and fibronectin receptor expression to wound contraction. J. Cell Biol, 110, pp. 133-145 (1990).

Werber, B., et al. A Prospective Study of 20 Foot and Ankle Wounds Treated with Cryopreserved Amniotic Membrane and Fluid Allograft. The Journal of Foot & Ankle Surgery. vol. 52, Issue 5, Sep.-Oct. 2013, pp. 615-621.

Werner, S. et al., The function of KGF in morphogenesis of epithelium and reepithelialization of wounds. Science, 266, pp. 819-822 (1994).

Weyrich AS and Zimmerman GA., Platelets: signaling cells in the immune continuum. Trends Immunol Sep. 2004; 25(9): 489-495.

Wilson, GJ et al., Acellular matrix allograft small caliber vascular prostheses. Trans Am Soc Artif Intern 1990; 36:340-343.

Woodley, D. et al., Collagen telopeptides (cross-linking sites) play a role in collagen gel lattice contraction. J Invest Dermatol, 97, 580-585 (1991).

Wu, M., et al. Comparison of the Biological Characteristics of Mesenchymal Stem Cells Derived from the Human Placenta and Umbilical Cord. Scientific Reports | (2018) 8:5014. DOI:10.1038/s41598-018-23396-1.

Xu, J. and Clark, R., Extracellular matrix alters PDGF regulation of fibroblast integrins. J Cell Biol, 132, pp. 239-249 (1996).

Yao, T, et al. Animal-cell culture media: History, characteristics, and current issues. Reprod Med Biol. 2017;16:99-117.

Zhang, X., et al., Mesenchymal progenitor cells derived from chorionic villi of human placenta for cartilage tissue engineering. Biochem Biophys Res Commun, 2006, 340: 944-952.

Zhang, X., et al., Successful immortalization of mesenchymal progenitor cells derived from human placenta and the differentiation abilities of immortalized cells. Biochem Biophys Res Commun, 2006, 351: 853-859.

Zhao, B., et al. Exosomal MicroRNAs Derived from Human Amniotic Epithelial Cells Accelerate Wound Healing by Promoting the Proliferation and Migration of Fibroblasts. Stem Cells International, vol. 2018, Article ID 5420463, 10 pages.

Chen, Q., et al. Human amniotic epithelial cell feeder layers maintain iPS cell pluripotency by inhibiting endogenous DNA methyltransferase 1. Experimental and therapeutic medicine 6: 1145-1154, 2013.

Buseman, J.,et al. Amniotic Fluid for Ex Vivo Skin Preservation: A Comparative Study of Tissue Preservation Solutions. Annals of Plastic Surgery: Dec. 2013—vol. 71—Issue 6—p. 643-645.

Ilan, N. et al., Distinct signal transduction pathways are utilized during the tube formation and survival phases of in vitro angiogenesis. J Cell Sci, 111, 3621-3631 (1998).

Kim, EY, et al. The potential of mesenchymal stem cells derived from amniotic membrane and amniotic fluid for neuronal regenerative therapy. BMB Rep. 2014; 47(3): 135-140.

Koizumi, N., et al. Growth factor mRNA and protein in preserved human amniotic membrane. Current Eye Research. 2000, vol. 20, No. 3, pp. 173-177.

Kumar, V., et al. Animal Models for the Evaluation of Wound Healing Activity. International Bulletin of Drug Research., 3(5): 93-107, 2013.

Leibovich, S, and Ross, R., The Role of the Macrophage in Wound Repair, A Study with Hydrocortisone and Antimacrophage Serum. Am J Pathol, 78, pp. 1-100 (1975).

Lichtenberger, BM, et al. Epidermal [beta]-catenin activation remodels the dermis via paracrine signalling to distinct fibroblast lineages. Nat Commun. Feb. 3, 2016;7:10537. doi: 10.1038/ncomms10537.

Madlener, M. et al., Matrix Metalloproteinases (MMPs) and Their Physiological Inhibitors (TIMPs) Are Differentially Expressed during Excisional Skin Wound Repair. Exp Cell Res, 242, 201-210, Article No. EX984049 (1998).

Madri, J. et al., Angiogenesis in Clark, R. Ed. The molecular and cellular biology of wound repair. 2nd Ed. New York, Plenum Press, pp. 355-371 (1996).

Malone, JM et al., Detergent-extracted small-diameter vascular prostheses. J Vasc Surg 1984; 1 :181-91.

Mignatti, P. et al., Proteinases and Tissue Remodeling. In Clark, R. Ed. The molecular and cellular biology of wound repair. 2nd Ed. New York, Plenum Press, 427-474 (1996).

Miki, T. Amnion-derived stem cells: in quest of clinical applications. Stem Cell Research & Therapy 2011, 2:25.

Miki, T. et al., Amnion-Derived Pluripotent/Multipotent Stem Cells. Stem Cell Reviews, 2006, 2:133-142.

Miki, T. et al., Stem Cell Characteristics of Amniotic Epithelial Cells. Stem Cells, 2005, 23: 1549-1559.

(56) References Cited

OTHER PUBLICATIONS

Miyagi C, et al., STAT3 noncell-autonomously controls planar cell polarity during zebrafish convergence and extension. J Cell Biol 2004, 166(7):975-981.

Montesano, R. and Orci, L. Transforming growth factor f3 stimulates collagen-matrix contraction by fibroblasts: Implications for wound healing. Proc Natl Acad Sci USA, 85, 4894-4897 (1988).

Nanney, L. and King, L. Epidermal Growth Factor and Transforming Growth Factor-alpha. In Clark, R. Ed. The molecular and cellular biology of wound repair. 2nd Ed. New York, Plenum Press, pp. 171-194 (1996).

Nissen, N. et al., Vascular Endothelial Growth Factor Mediates Angiogenic Activity during the Proliferative Phase of Wound Healing. Am J Pathol, 152, 1445-1552 (1998).

Oliveira, MS, et al. Placental-derived stem cells: Culture, differentiation and challenges. World J Stem Cells, May 26, 2015; 7(4): 769-775.

Orczyk-Pawilowicz, M., et al., "Metabolomics of human amniotic fluid and maternal plasma during normal pregnancy," PLos ONE (2016) 11(4): e0152740.

Ozgenel G Y et al., Effects of human amniotic fluid on peripheral nerve scarring and regeneration in rats. J Neurosurg 2003; 98: 371-377.

Paladini, R. et al., Onset of re-epithelialization after skin injury correlates with a reorganization of keratin filaments in wound edge keratinocytes : defining a potential role for keratin 16. J. Cell Biol, 132, pp. 381-397 (1996).

Parolini, O. et al., Concise Review: Isolation and Characterization of Cells from Human Term Placenta: Outcome of the First International Workshop on Placenta Derived Stem Cells Stem Cell, 2008, 26:300-311.

Pilcher, B. et al., The Activity of Collagenase-1 Is Required for Keratinocyte Migration on a Type I Collagen Matrix. J Cell Biol, 137, pp. 1445-1457 (1997).

Pintucci, G. et al., Angiogenesis and the fibrinolytic system. Semin Thromb Hemost, 22, 517-524 (1996).

Qian D, et al., Wnt5a functions in planar cell polarity regulation in mice. Dev Biol 2007, 306(1):121-133.

Qiu, C, et al. Targeting connexin 43 expression accelerates the rate of wound repair. Curr Biol 13, 1697-703 (2003).

Rappolee, D. et al., Wound macrophages express TGF-alpha and other growth factors in vivo: analysis by mRNA phenotyping. Science, 241, pp. 708-712 (1988).

Rennie, K. et al., "Applications of amniotic membrane and fluid in stem cell biology and regenerative medicine," Stem Cells Intl. (2012) Article ID 721538, 13 pages.

Riches, D., In Clark R., Ed. The molecular and cellular biology of wound repair, 2nd Ed. New York, Plenum Press, Chapter 3 pp. 95-141. 1988.

Roberts, A. and Sporn, M, Transforming Growth Factor-beta. Clark, R. ed. The molecular and cellular biology of wound repair. 2nd Ed. New York, Plenum Press, pp. 275-308 (1996).

Robson MC et al., Wound healing: Biologic features and approaches to maximize healing trajectories. Curr Probl Surg 2001; 38: 72-140.

Robson, M. et al., Platelet-derived growth factor BB for the treatment of chronic pressure ulcers. Lancet, 339, pp. 23-25 (1992).

Robson, M. et al., The safety and effect of topically applied recombinant basic fibroblast growth factor on the healing of chronic pressure sores.. Ann Surg, 216, pp. 401-406 (1992).

Roubelakis, MG, et al., Amniotic fluid and amniotic membrane stem cells: marker discovery, Stem Cells Intl (2012) article 107836.

Schiro, J. et al., Integrin alpha 2 beta 1 (VLA-2) mediates reorganization and contraction of collagen matrices by human cells. Cell, 67, 403-410 (1991).

Semenov, M. V.; Snapshot: Noncanoncal Wnt Signaling Pathways. Cell 2007, 131: 1378.

Sephel, G.C. and Woodward, S.C. Repair, Regeneration and Fibrosis. Rubin's Pathology, Chapter 3. Rubin, R. and Strayer, D.S. Eds; 5th Ed., Wolters Kluwyer Health, /Lippincott Williams & Wilkins, Philadelphia, PA (2008), at 71.

Shao-Cong Sun, Non-canonical NF-kB signaling pathway, Cell Res. (2011)21: 71-85.

Siar C H, et al. Differential expression of canonical and non-canonical Wnt ligands in ameloblastoma. J. Oral Pathol. Med., 2012, 41(4):332-339.

Singer AF and Clark RA, Cutaneous wound healing. N Engl J Med Sep. 2, 1999; 341(10): 738-746.

Soncini, M. et al., Isolation and characterization of mesenchymal cells from human fetal membranes. J Tissue Eng Regen Med, 2007, 1:296-305.

Southard, James H. and Belzer, Folkert O., Organ Preservation. Annual Review of Medicine. (1995) 46: 235-47.

Steed, D. Clinical evaluation of recombinant human platelet—derived growth factor for the treatment of lower extremity diabetic ulcers. J Vasc Surg, 21, pp. 71-78 (1995).

Sun, Shao-Cong, Non-canonical NF-kB signaling pathway, Cell Res. (2011) 21: 71-85.

Swanson, D. K., et al., Improved heart preservation with UW preservation solution. Journal of Heart Transplantation, (1988), vol. 7, No. 6, pp. 456-467.

Takeuchi M, et al., The prickle-Related Gene in Vertebrates Is Essential for Gastrulation Cell Movements. Curr Biol 2003, 13(8):674-679.

Vaalamo, M. et al., Distinct Populations of Stromal Cells Express Collagenase-3 (MMP-13) and Collagenase-1 (MMP-1) in Chronic Ulcers but Not in Normally Healing Wounds. J Invest Dermatol, 109, pp. 96-101 (1997).

Van Raemdonck, D. et al., Machine perfusion in organ transplantation: a tool for ex-vivo graft conditioning with mesenchymal stem cells?. Curr. Opin. Organ Transplant. (2013) 18: 24-33.

Velnar T et al., The Wound Healing Process: an Overview of the Cellular and Molecular Mechanisms. The Journal of International Medical Research 2009; 37: 1528-1542.

Abraham, J. and Klagsburn, M. Modulation of Wound Repair by Members of the Fibroblast Growth Factor family. In Clark, R. Ed. The molecular and cellular biology of wound repair. 2nd Ed. New York, Plenum Press, pp. 195-248 (1996).

Aggarwal, BB, Signalling Pathways of the TNF Superfamily: a Double-Edged Sword. Nature Revs. Immuno. (2003) 3:745-56.

Alonso JE et al., The Management of Complex Orthopedic Injuries.. Surg Clin North Am 1996; 76: 879-903.

Bakhtyar, N., et al. Exosomes from acellular Wharton's jelly of the human umbilical cord promotes skin wound healing. Stem Cell Research & Therapy (2018) 9:193.

Baulier, E. et al. Amniotic Fluid-Derived Mesenchymal Stem Cells Prevent Fibrosis and Preserve Renal Function in a Preclinical Porcine Model of Kidney Transplantation. Stem Cells Translational Medicine. 2014;3:809-820.

Benirschke, K. and Kaufmann, P. Pathology of the human placenta. 4th Ed. New York, Springer-Verlag, 2000, pp. 42-46, 116, 281-297.

Bigbey, M., eta al. Amnion-Derived Fluid and Amniotic Fluid. Axolotl Biologix. MRK0001-v 1.0.0. 2 pages.

Brooks, P. et al., Requirement of vascular integrin alpha v beta 3 for angiogenesis. Science, 264, 569-571 (1994).

Brown, E. Phagocytosis. Bioessays, 17:109-117 (1995).

Brown, L. et al. Expression of vasclar permeability factor (vascular endothelial growth factor) by epidermal keratinocytes during wound healing. J Exp Med, 176, 1375-1379 (1992).

Bugge, T. et al., Loss of Fibrinogen Rescues Mice from the Pleiotropic Effects of Plasminogen Deficiency. Cell, 87, 709-719 (1996).

Camilli, T. C., Striking the Target in Wnt-y Conditions: Intervening in Wnt Signaling During Cancer Progression. Biochem. 2010, Pharmacol. 80(5): 702-711.

Campbell, J. et al., "Biochemical composition of amniotic fluid and extrambryonic coelomic fluid in the first trimester of pregnancy," Br. J. Obstet. Gynaecol. (1992) 99 (7): 563-565.

Carreira-Barbosa F, et al., Prickle 1 regulates cell movements during gastrulation and neuronal migration in zebrafish. Development 2003, 130(17):4037-4046.

Casey, M. and MacDonald P. Interstitial Collagen Synthesis and Processing in Human Amnion: A Property of the Mesenchymal Cells. Biol Reprod, 1996, 55: 1253-1260.

(56) References Cited

OTHER PUBLICATIONS

Chan-Kyung, J., et al. Proteomics Analysis of Human Amniotic Fluid. Molecular & Cellular Proteomics 6:1406-1415, 2007.
Chang, L. et al. The dynamic properties of intermediate filaments during organelle transport. Journal of Cell Science 122, 2914-2923 (2009).
Cho, C-K.J., et al., "Proteomics Analysis of Human Amniotic Fluid," (2007) Molecular & Cellular Proteomics 6: 1406-1415.
Ciubotaru, A. and Haverrich, A., Ex vivo Approach to Treat Failing Organs: Expanding the Limits. Eur. Surg. Res. (2015) 54: 64-74.
Clark R. et al., Fibronectin and Fibrin Provide a Provisional Matrix for Epidermal Cell Migration During Wound Reepithelialization. J. Invest Dermatol, 79, pp. 264-269 (1982).
Clark, R. et al., Collagen matrices attenuate the collagen-synthetic response of cultured fibroblasts to TGF-β. J Cell Sci, 108, pp. 1251-1261 (1995).
Clark, R. et al., Fibronectin is produced by blood vessels in response to injury. J. Exp Med, 156, 646-651 (1982).
Clark, R. et al., Platelet Isoforms of Platelet-derived Growth Factor Stimulate Fibroblasts To Contract Collagen Matrices. J Clin Invest, 84, 1036-1040 (1989).
Clark, R., Fibronectin matrix deposition and fibronectin receptor expression in healing and normal skin. J Invest Dermatol, 94, Suppl, pp. 128S-134S (1990).
Collins, GM et al., Kidney preservation for transportation experimental analysis of optimal perfusate composition. Br. J. Surg. (1972) 59: 187-89.
Courtman, DW et al.,Development of a pericardial acellular matrix biomaterial: biochemical and mechanical effects of cell extraction. J Biomed Mater Res 1994; 28:655-666.
Coutinho, P., et al. Limiting burn extension by transient inhibition of connexin 43 expression at the site of injury. Br J Plast Surg 58, 658-67 (2005).
Cunningham, F. et al., The placenta and fetal membranes, Williams Obstetrics, 20th ed. Appleton and Lange, 1997, 95-125.
Davydova, DA., et al. Cell Phenotypes in Human Amniotic Fluid. Acta Naturae. No. 2. 2009. pp. 98-103.
Desmouliere, A. and Gabbiani, G. The role of the myofibroblast in wound healing and fibrocontractive diseases. In Clark, R. Ed. The molecular and cellular biology of wound repair. 2nd Ed. New York, Plenum Press, Chapter 13 pp. 391-423 (1996).
Eslaminejad, MB., et al. Amniotic Fluid Stem Cells and Their Application in Cell-Based Tissue Regeneration. Int J Fertil Steril. 2012; 6(3): 147-156.
Folkman, J. and D'Amore, P, Blood vessel formation: what is its molecular basis?. Cell, 87, pp. 1153-1155 (1996).
Folkman, J., Angiogenesis and angiogenesis inhibition: an overview, EXS, 79, 1-8, (1997).
Fundamental Immunology, 4th Ed., William E. Paul, ed. Lippincott-Raven Publishers, Philadelphia (1999) at 1051-1053.
Gabbiani, G. et al., Cytoplasmic filaments and gap junctions in epithelial cells and myofibroblasts during wound healing.. J Cell Biol, 76, pp. 561-568 (1978).
Gao X et al., Effects of amniotic fluid on proteases: a possible role of amniotic fluid in fetal wound healing. Ann Plastic Surg 1994; 33: 128-134.
Goliger, J. and Paul, D. Wounding Alters Epidermal Connexin Expression and Gap Junction-mediated Intercellular Communication. Mol Biol Cell, 6, pp. 1491-1501 (1995).
Gordon, MD and Nusse, R. Wnt Signaling: Multiple Pathways, Multiple Receptors, and Multiple Transcription Factors. J. Biol. Chem. (2006) 281 (32) 22429-22433.
Gorentla, BK and Zhong, X-P, T Cell receptor signal transduction in T Lymphocytes, J. Clin. Cell Immunol. (2012) (Suppl 12) 23 pages.
Gray, A. et al., A alpha and B beta chains of fibrinogen stimulate proliferation of human fibroblasts. J Cell Sci,104, pp. 409-413 (1993).
Greiling, D. and Clark R., Fibronectin provides a conduit for fibroblast transmigration from collagenous stroma into fibrin clot provisional matrix. J. Cell Sci, 110, pp. 861-870 (1997).
Grose, R. and Werner, S. (2004). Wound-healing studies in transgenic and knockout mice. Mol Biotechnol 28, 147-66.
Grzywocz, Z. et al. Growth factors and their receptors derived from human amniotic cells in vitro. Folia Histochemica et Cytobiologica (2014) 52 (3):163-70.
Guibert, E.E. et al, Organ Preservation: Current Concepts and New Strategies for the Next Decade. Transfus. Med. Hemother. (2011) 38(2): 125-142.
Guidance for Industry: Chronic Obstructive Pulmonary Disease: Developing Drugs for Treatment. Nov. 2007. http://www.fda.gov/cder/guidance/index.htm.
Gulbis, B, et al. Amniotic fluid biochemistry in second-trimester trisomic pregnancies: relationships to fetal organ maturation and dysfunction. Early Human Development 52 (1998) 211-219.
Gupta, A. et al. (2015) Amnion and Chorion Membranes: Potential Stem Cell Reservoir with Wide Applications in Periodontics. International Journal of Biomaterials vol. 2015, Article ID 274082, 9 pages.
Heidari, Z. et al. Characterization of the Growth Factor Activity of Amniotic Fluid on Cells from Hematopoietic and Lymphoid Organs of Different Life Stages. Microbiol. Immunol., 40(8), 583-589, 1996.
Heldin, C. and Westermark B., In: Clark R., ed. The molecular and cellular biology of wound repair, 2nd Ed. New York, Plenum Press, Chapter 7. pp. 249-273, (1996).
Hu, Y., et al. Exosomes from human umbilical cord blood accelerate cutaneous wound healing through miR-21-3p-mediated promotion of angiogenesis and fibroblast function. Theranostics 2018, vol. 8, Issue 1. 169-184.
Maurer, E. J., et al., Comparison of UW and Collins solution for preservation of the rat heart. Transplantation Proceedings, (1990), vol. 22, No. 2, pp. 548-550.
U.S. Appl. No. 16/640,699, filed Feb. 20, 2020, US-2019-0300848-A1, Published.
PCT/US18/47818, Aug. 23, 2018, WO 2019/040790, Published.

\* cited by examiner

FIG. 2A
SSEA4
FIG. 2B
DAPI
AEC
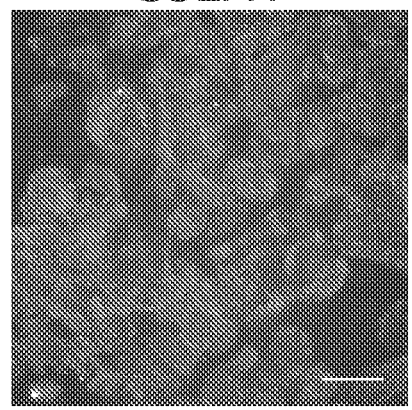
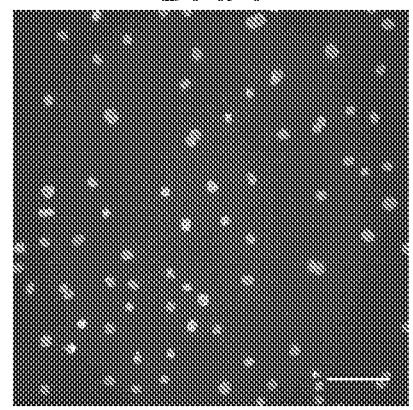
AFC
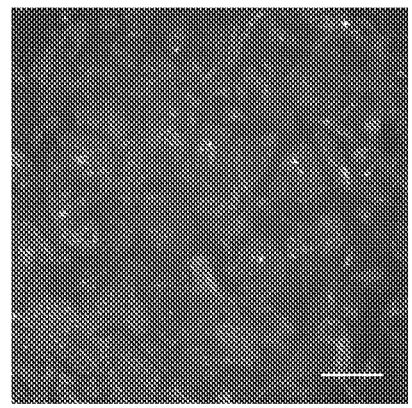
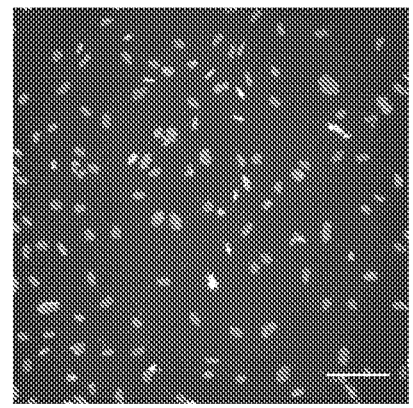
FIG. 2C
FIG. 2D 0h DMEM 24h DMEM 0h SFM2

24h SFM2

0h SFM1

24h SFM1

FIG. 6

| | Trypan blue exclusion assay | Bradford assay | | Liquid chromatography-mass spectrometry | |
|---|---|---|---|---|---|
| | viable cells (+/- SD) | total protein (microgram/ml) | sample | proteins identified | % of total |
| | N/A | 66 | all proteins | 1043 | 100 |
| | 334350 (61384) | 91 | SFM1 | 69 | 6.6 |
| | 43200 (2934) | 79 | co-AC | 824 | 79.0 |
| | | | AEC | 655 | 62.8 |
| | 334000 (12000) | 73 | AFC | 777 | 74.5 |

FIG. 8

| secretome comparison | proteins identified | % of co-AC>0 |
|---|---|---|
| co-AC>0 | 824 | 100 |
| co-AC>BG | 784 | 95.2 |
| co-AC>(BG+AEC) | 452 | 54.9 |
| co-AC>(BG+AFC) | 421 | 51.1 |
| co-AC>(BG+AEC+AFC) | 225 | 27.3 |

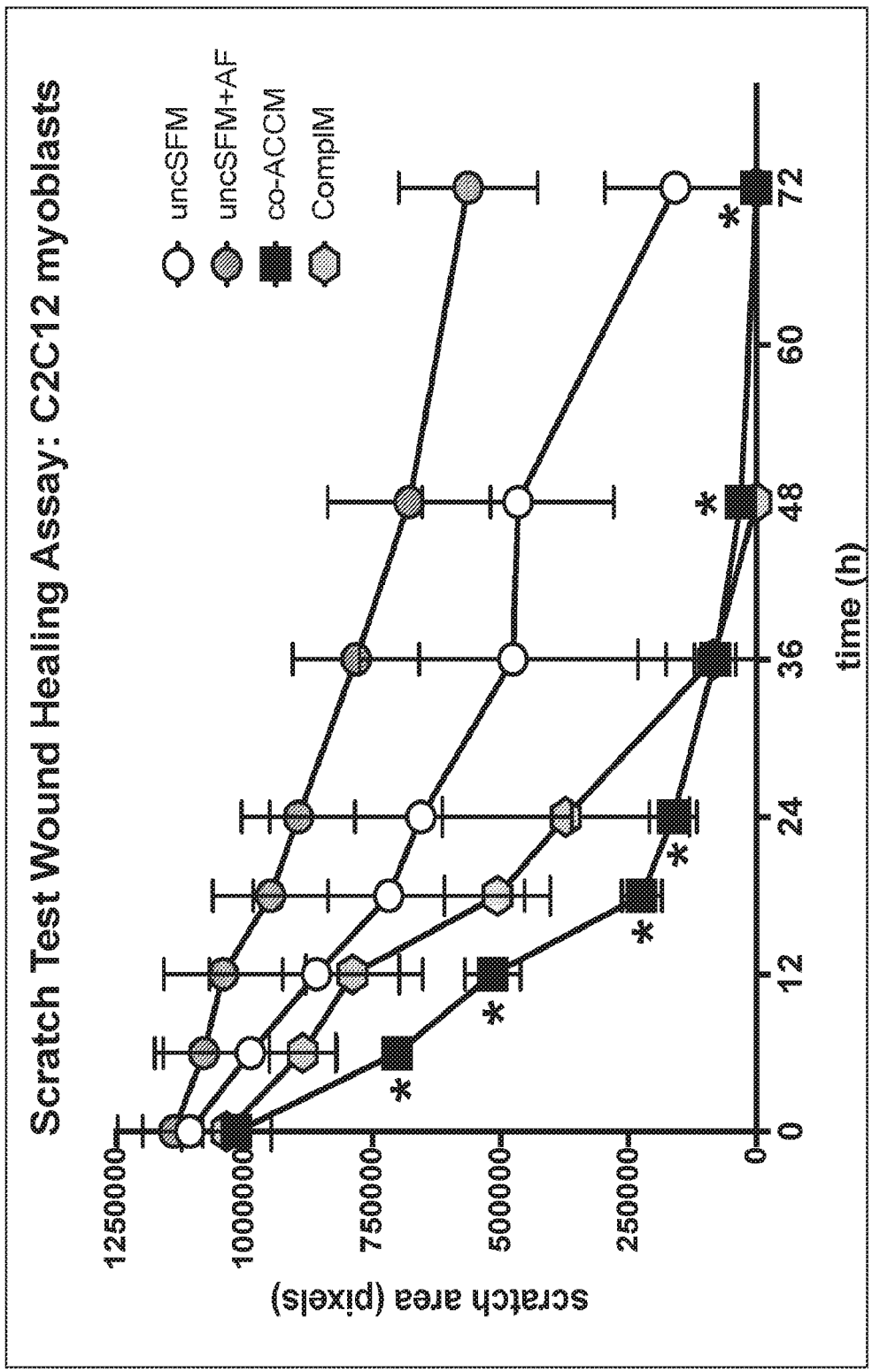

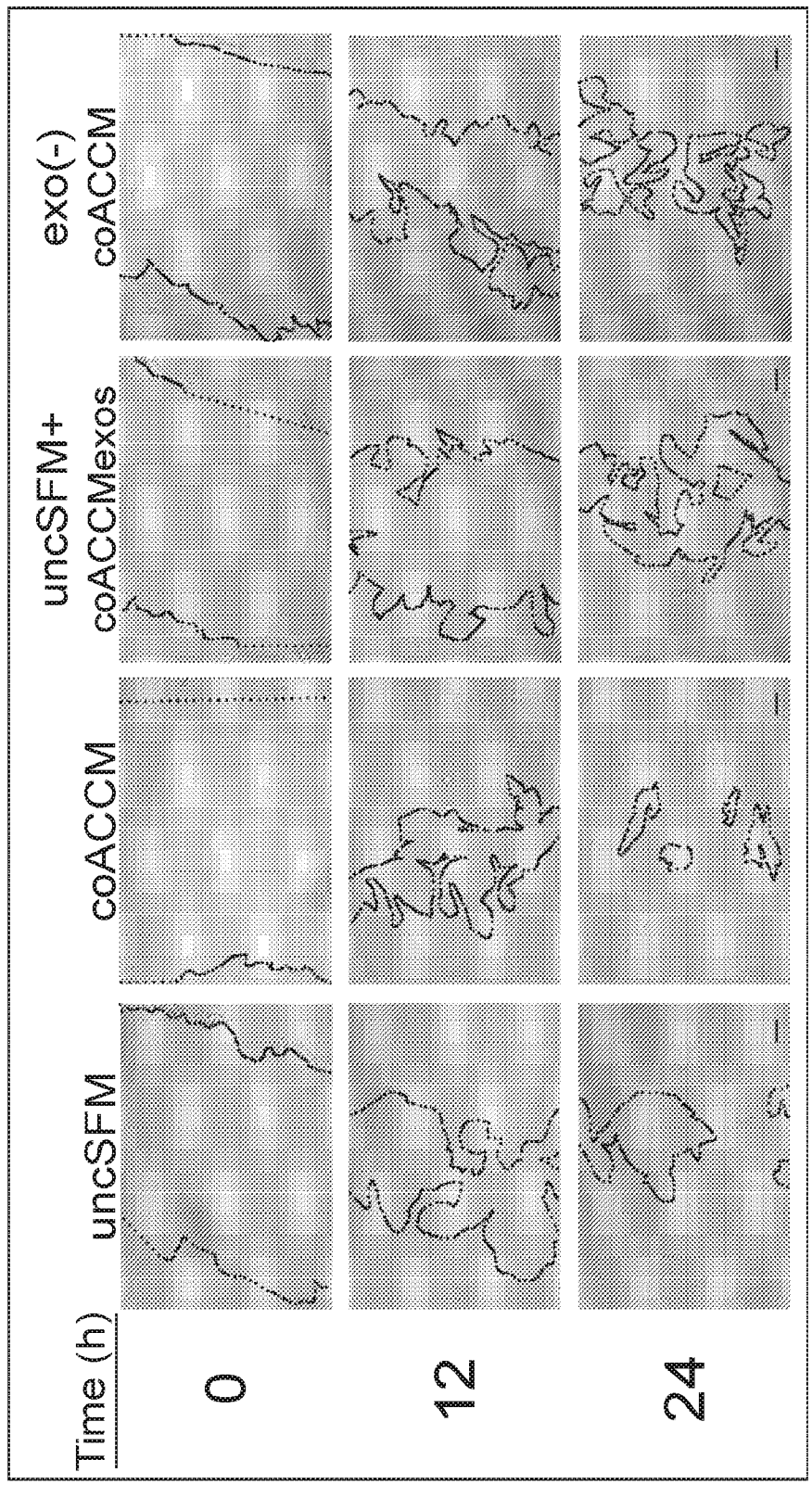

COMPOSITIONS CONTAINING AMNIOTIC COMPONENTS AND METHODS FOR PREPARATION AND USE THEREOF

CROSS REFERENCE TO RELATED APPLICATION(S)

This application is a continuation in part of PCT/US 18/47818 (filed Aug. 23, 2018), entitled COMPOSITIONS CONTAINING AMNIOTIC COMPONENTS AND METHODS FOR PREPARATION AND USE THEREOF, which claims the benefit of priority to U.S. Provisional Patent Application No. 62/549,076 filed on Aug. 23, 2017, entitled "COMPOSITIONS CONTAINING AMNIOTIC COMPONENTS AND METHODS FOR PREPARATION AND USE THEREOF". The contents of each of these applications are incorporated by reference herein.

TECHNICAL FIELD

The present disclosure relates to compositions containing biologically active components of amniotic fluid and methods of preparation and use thereof.

BACKGROUND

The amniotic sac consists of the outer layer chorion and the inner layer amnion. The amniotic fluid is the fluid within the amniotic membrane.

The fetal adnexa (meaning connected parts), is composed of the placenta, fetal membranes, and umbilical cord. At term, the placenta is discoid in shape with a diameter of 15-20 cm and a thickness of 2-3 cm. The fetal membranes, amnion and chorion, which enclose the fetus in the amniotic cavity, and the endometrial decidua extend from the margins of the chorionic disc. The chorionic plate (fetal component of extraembryonic tissue) is a multilayered structure that faces the amniotic cavity. It consists of two different structures: the amniotic membrane (composed of epithelium, compact layer, amniotic mesoderm, and spongy layer) and the chorion (composed of mesenchyme and a region of extravillous proliferating trophoblast cells interposed in varying amounts of Langhans fibrinoid, either covered or not by syncytiotrophoblast).

Villi originate from the chorionic plate and anchor the placenta through the trophoblast of the basal plate and maternal endometrium. From the maternal side, protrusions of the basal plate within the chorionic villi produce the placental septa, which divide the parenchyma into irregular cotyledons (Parolini, O. et al., 2008, Stem Cell, 2008, 26:300-311).

Some villi anchor the placenta to the basal plate, whereas others terminate freely in the intervillous space. Chorionic villi present with different functions and structure. In the term placenta, the stem villi show an inner core of fetal vessels with a distinct muscular wall and connective tissue consisting of fibroblasts, myofibroblasts, and dispersed tissue macrophages (Hofbauer cells). Mature intermediate villi and term villi are composed of capillary vessels and thin mesenchyme. A basement membrane separates the stromal core from an uninterrupted multinucleated layer, called the syncytiotrophoblast. Between the syncytiotrophoblast and its basement membrane are single or aggregated Langhans cytotrophoblastic cells, commonly called cytotrophoblast cells (Parolini, O. et al., 2008, Stem Cell, 2008, 26:300-311).

The placenta contains three layers: the amnion, the chorion, both of which are derived from the embryo, and the decidua, which is maternal tissue derived. The chorion is derived from the trophoblast layer, while the amnion is derived from the epiblast, which gives rise to all of the germ layers of the embryo, as early as 8 days after fertilization. Four regions of fetal placenta can be distinguished: an amniotic epithelial region, an amniotic mesenchymal region, a chorionic mesenchymal region, and a chorionic trophoblastic region. FIG. 2 from Gupta, A. et al. (2015). Amnion and Chorion Membranes: Potential stem cell reservoir with wide applications in periodontics. Intl J. Biomaterials. (2015) article 274082, incorporated by reference herein, shows schematic line representations of the histological architecture of amnion (A) and chorion (C) membranes.

The Amnion

The amnion is a thin, avascular membrane composed of an inner epithelial layer and an outer layer of connective tissue that, and is contiguous, over the umbilical cord, with the fetal skin. The outer layer comprises human amniotic mesenchymal stromal cells (hMSCs), which are surrounded by an intracellular matrix. Grzywocz, Z. et al. Folia Histochemica et Cytobiologica (2014) 52 (3):163-70. The inner layer closest to the fetus is the amniotic epithelium (AE), which is an uninterrupted, single layer of flat, cuboidal and columnar epithelial cells and is in contact with amniotic fluid. It is attached to a distinct basal lamina that is, in turn, connected to the amniotic mesoderm (AM). In the amniotic mesoderm closest to the epithelium, an acellular compact layer is distinguishable, composed of collagens I and III and fibronectin. Deeper in the AM, a network of dispersed fibroblast-like mesenchymal cells and rare macrophages are observed. It has been reported that the mesenchymal layer of amnion contains two subfractions, one comprising a mesenchymal phenotype, also known as amniotic mesenchymal stromal cells, and the second containing monocyte-like cells. Blood vessels or nerves are absent from amniotic membrane. It derives its nutrition directly by diffusion out of the amniotic fluid.

Chorion

A spongy layer of loosely arranged collagen fibers separates the amniotic and chorionic mesoderm. The chorionic membrane (chorion leave) consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297).

Amniotic-Derived Stem Cells

The amniotic membrane itself contains multipotent cells that are able to differentiate in the various layers. Studies have reported their potential in neural and glial cells, cardiac repair and also hepatocyte cells. Studies have shown that human amniotic epithelial cells express stem cell markers and have the ability to differentiate toward all three germ layers. These properties, the ease of isolation of the cells, and the availability of placenta, make amniotic membrane a useful and noncontroversial source of cells for transplantation and regenerative medicine.

Amniotic epithelial cells can be isolated from the amniotic membrane by several methods that are known in the art. According to one such method, the amniotic membrane is stripped from the underlying chorion and digested with trypsin or other digestive enzymes. The isolated cells readily attach to plastic or basement membrane-coated culture dishes. Culture is established commonly in a simple medium such as Dulbecco's Modified Eagle's Medium (DMEM) supplemented with 5%-10% serum and epidermal growth factor (EGF), in which the cells proliferate robustly and display typical cuboidal epithelial morphology. Normally, 2-6 passages are possible before proliferation ceases. Amniotic epithelial cells do not proliferate well at low densities.

Amniotic membrane contains epithelial cells with different surface markers, suggesting some heterogeneity of phenotype. Immediately after isolation, human amniotic epithelial cells express very low levels of human leukocyte antigen (HLA)-A, B, C; however, by passage 2, significant levels are observed. Additional cell surface antigens on human amniotic epithelial cells include, but are not limited to, ATP-binding cassette transporter G2 (ABCG2/BCRP), CD9, CD24, E-cadherin, integrins 6 and 1, c-met (hepatocyte growth factor receptor), stage-specific embryonic antigens (SSEAs) 3 and 4, and tumor rejection antigens 1-60 and 1-81. Surface markers thought to be absent on human amniotic epithelial cells include SSEA-1, CD34, and CD133, whereas other markers, such as CD117 (c-kit) and CCR4 (CC chemokine receptor), are either negative or may be expressed on some cells at very low levels. Although initial cell isolates express very low levels of CD90 (Thy-1), the expression of this antigen increases rapidly in culture (Miki, T. et al., Stem Cells, 2005, 23: 1549-1559; Miki, T. et al., Stem Cells, 2006, 2: 133-142).

In addition to surface markers, human amniotic epithelial cells express molecular markers of pluripotent stem cells, including octamer-binding protein 4 (OCT-4) SRY-related HMG-box gene 2 (SOX-2), and Nanog (Miki, T. et al., Stem Cells, 2005, 23: 1549-1559).

Human amniotic mesenchymal cells (hAMSC) and human chorionic mesenchymal cells (hCMSC) are thought to be derived from extraembryonic mesoderm. hAMSC and hCMSC can be isolated from first-, second-, and third-trimester mesoderm of amnion and chorion, respectively. For hAMSC, isolations are usually performed with term amnion dissected from the deflected part of the fetal membranes to minimize the presence of maternal cells. For example, homogenous hAMSC populations can be obtained by a two-step procedure, whereby: minced amnion tissue is treated with trypsin to remove hAEC and the remaining mesenchymal cells are then released by digestion (e.g., with collagenase or collagenase and DNase). The yield from term amnion is about 1 million hAMSC and 10-fold more hAEC per gram of tissue (Casey, M. and MacDonald P., Biol Reprod, 1996, 55: 1253-1260).

hCMSCs are isolated from both first- and third-trimester chorion after mechanical and enzymatic removal of the trophoblastic layer with dispase. Chorionic mesodermal tissue is then digested (e.g., with collagenase or collagenase plus DNase). Mesenchymal cells also have been isolated from chorionic fetal villi through explant culture, although maternal contamination is more likely (Zhang, X., et al., Biochem Biophys Res Commun, 2006, 340: 944-952; Soncini, M. et al., J Tissue Eng Regen Med, 2007, 1:296-305; Zhang et al., Biochem Biophys Res Commun, 2006, 351: 853-859). The surface marker profile of cultured hAMSC and hCMSC, and mesenchymal stromal cells (MSC) from adult bone marrow are similar.

Growth Factor Activity of Amniotic Fluid

One of the functions of amniotic cells is the release of growth factors and cytokines, which regulate different processes during development of the embryo. Grzywocz, Z. et al. Folia Histochemica et Cytobiologica (2014) 52 (3): During fetal development, VEGF increases permeability of the human amnion. In vitro studies have shown that amnion-produced growth factors participate in angiogenesis, re-epithelialization, and immunomodulation. Some factors (e.g., macrophage colony-stimulating factor (M-CSF) stimulate cell differentiation and proliferation. Other factors, like IGF-2, may promote proliferation.

Growth factors produced by amnion cell fractions and by whole amnion tissue using an in vitro cytokine assay (Id.). The assay detected in supernatants epidermal and fibroblast growth factors (HB-EGF, EGF-2, EGF-R, bFGF, FGF-4, FGF-6, FGF-7), neural and glial growth factors (bNGF, GDNF, NT-3, NT-4), angiogenic growth factors (VEGF, VEGF-D, VEGF-R2, VEGF-R3, PLGF), hematopoietic growth factors (G-CSG, GM-CSF, M-CSF, M-CSF-R, SCF, SCF-R), insulin-like growth factors (IFG-1, IGF-2, IGF-ISR, IGFBP-1, IGFBP-2, IGFBP-3, IGFBP-4, IGFBP-6), platelet derived growth factors (PDGF-AA, PDGF-AB, PDGF-BB, PDGFRa, PDGFRb), transforming growth factors (TGF-a, TGF-b, TGF-b2, TGF-b3) and other proteins (HGF, AR). The study focused on statistically significant changes over time in the level of growth factors and their receptors over time, measured at 3 hr, 6 hr, 24 hr, 48 hr, Cell fractions were isolated as described by Soncini et al, J. Tissue Eng. Regen. Med. (2007) 1:296-305, with minor modifications. Whole human amniotic membranes comprised of equal amounts of hAMSCs and hAECs released EGF-R, IGF-2, IGFBP-2, IGFBP-2, and IGFBP6 into conditioned media. Amniotic cell fraction 1, which stained positively for mesenchymal cell markers CD73 (86%), CD90 (19.3%) and CD105 (2.2%), released only NT-4, the concentration of which increased statistically during the study period, suggesting that NT4 played a local role in the function of the amnion epithelium, possibly related to apoptosis. Amniotic cell fraction 2, which stained positively for epithelial cell markers, cytokeratins 4/5/6/8/10/13/18, and which contained mainly amnion epithelial cells, released hematopoietic growth factors including G-CSF, M-CSF, PDGF, and the angiogenesis regulator, PLGF into conditioned media.

Amniotic Fluid (AF)

Amniotic fluid is a complex and dynamic biological fluid that provides mechanical protection, nutrients, and other molecules required for fetal growth and well-being. (Cho, C-K. J., et al, "Proteomics Analysis of Human Amniotic Fluid," (2007 Molecular & Cellular Proteomics 6: 1406-1415). Both the quantitative and qualitative integrity of AF are essential for normal development of the human fetus during pregnancy.

During embryogenesis, the amniotic cavity first appears at 7-8 days after fertilization and in early gestation the amniotic fluid originates mostly from maternal plasma that crosses the fetal membranes. Rennie, K. et al., "Applications of amniotic membrane and fluid in stem cell biology and regenerative medicine," Stem Cells Intl. (2012) article 721538. Fetal urine first enters the amniotic space at 8-11 weeks gestation, and in the second half of pregnancy, fetal urine becomes the major contributor to amniotic fluid. Id. At this time, fetal skin keratinization is compete, leading to reduced water transport across the skin and a decrease in AF osmolality. Id. For the remainder of gestation, fluid volume is determined by different mechanisms, including fetal urine production, oral, nasal, tracheal and pulmonary fluid secretion, fetal swallowing, and the contributions of the intramembranous pathway. Id.

AF contains water, amino acids, peptides, proteins, carbohydrates, lipids, lactate, pyruvate, enzymes, growth factors, hormones, and electrolytes. (Cho, C-K. J., et al, "Proteomics Analysis of Human Amniotic Fluid," Molecular & Cellular Proteomics (2007) 6: 1406-1415; Rennie, K. et al., "Applications of amniotic membrane and fluid in stem cell biology and regenerative medicine," Stem Cells Intl. (2012) article 721538.). While the major component of AF is water, its overall composition varies throughout pregnancy. Roubelakis, M G, et al., "Amniotic fluid and amniotic membrane stem cells: marker discovery, 'Stem Cells Intl (2012) article 107836). In addition, fluid secretions from the fetus into the AF carry a variety of fetal cells, resulting in a heterogeneous population of cells derived from fetal skin, gastrointestinal, respiratory and urinary tracts, and the amniotic membrane. Rennie, K. et al., "Applications of amniotic membrane and fluid in stem cell biology and regenerative medicine," Stem Cells Intl. (2012) article 721538. As the fetus develops, the volume and composition of the amniotic fluid change drastically, and the complement of cells detected in amniotic fluid samples taken at different gestational ages varies considerably.

Amniotic fluid cells (AFCs) represent a heterogeneous population derived from the three germ layers. These cells have an epithelial origin and are derived from either the developing embryo or the inner surface of the amniotic membrane, which are characterized as amniotic membrane stem cells. Roubelakis, M G, et al., "Amniotic fluid and amniotic membrane stem cells: marker discovery, 'Stem Cells Intl (2012) article 107836). The AFCs are mainly composed of three groups of adherent cells categorized based on their morphological, growth and biochemical characteristics: epitheliod (E-type) cells, which are cuboidal to columnar cells derived from the fetal skin and urine; amniotic fluid (AF-type) cells originating from fetal membranes, and fibroblastic (F-type) cells generated mainly from fibrous connective tissue. The dominant cell type appears to be the AF type, coexpressing keratins and vimentins. Several studies have documented that human amniotic fluid stem cells (AFSCs) can be obtained from a small amount of second trimester AF collected during routine amniocenteses. The isolation of AFSCs can be categorized as follows: (i) a single step cultivation protocol, where the primary culture is left undisturbed for 7 days or more until the first colonies appear; (ii) a two-step cultivation protocol, where amniocytes not attached after 5 days in culture, were collected and further expanded; (iii) cell surface marker selection for CD117 (c-kit receptor) (iv) mechanical isolation of the initial mesenchymal progenitor cell colonies formed in the initial cultures; and (v) short term cultures to isolate fibroblastoid colonies. The majority of the AFSCs isolated following these steps shared a multipotent mesenchymal phenotype, and exhibited higher proliferation potential and a wider differentiation potential compared to adult MSCs. Roubelakis, M G, et al., "Amniotic fluid and amniotic membrane stem cells: marker discovery, 'Stem Cells Intl (2012) article 107836).

A detailed analysis of AFSC-conditioned media revealed the presence of proangiogenic and antiangiogenic factors using Liminex' MAP Technology. Veascular endothelial growth factor (VEGF), stromal cell-derived factor 1 (SDF-1), interleukin 8 (IL-8), monocyte chemotactic protein 1 (MCP-1) and two angiogenesis inhibitors, interferon-gamma (IFNγ) and interferon gamma-induced protein 10 (IP-10) have been identified as secreted proteins. (Id). A relatively small number of AFSCs was shown to be enough to secrete a detectable amount of proangiogenic growth factors and cytokines. Id.

Human Amniotic Fluid Proteome

Analysis of human AF samples from women at 16-18 weeks of gestation showed that albumin comprises nearly 70% of the protein content of AF, with immunoglobulins being the second most abundant fraction. (Cho, C-K. J., et al, "Proteomics Analysis of Human Amniotic Fluid," (2007) Molecular & Cellular Proteomics 6: 1406-1415)). Cho et al identified 842 proteins from 754 distinct genes and 88 proteins from uncharacterized genes in amniotic fluid. The proteins were sorted by the number of unique peptides identified from strong anion exchange (SAX) and strong cation exchange (SCX) methods, which is generally accepted as a semiquantitative measure of protein abundance The top 15 proteins in amniotic fluid with the largest number of unique peptides were, in descending order, albumin, immunoglobulins, fibronectin, serotransferrin, complement C3, α1-antitrypsin, ceruloplasmin, afetoprotein, vitamin D-binding protein, periostin, apolipoprotein A-1, antithrombin III, transforming growth factor β-induced protein ig-h3 precursor; α1-microglobulin and plasminogen. By comparison, the top 15 proteins in plasma in descending order are albumin, immunoglobulins, serotransferrin, fibrinogen, al microglobulin, α1-antitrypsin, complement C3, haptoglobin, apolipoprotein A-1, Apolipoprotien B, α1-acid glycoprotein, lipoprotein, factor H, ceruloplasmin, and complement C4.

Metabolomics

Standard biochemical variables were measured in pure samples of amniotic fluid and extraembryonic coelomic fluid obtained from women with a normal pregnancy between 7 and 12 weeks gestation having termination of pregnancy by transvaginal ultrasound guided amniocentesis. In the first trimester of pregnancy, levels of sodium, potassium and bicarbonate were significantly higher in amniotic fluid, while chloride, urea, bilirubin, protein, albumin, glucose, creatinine, calcium and phosphate were present in higher concentrations in extraembryonic coelomic fluid. Campbell, J. et al., "Biochemical composition of amniotic fluid and extrambryonic coelomic fluid in the first trimester of pregnancy," Br. J. Obstet. Gynaecol. (1992) 99 (7): 563-565.

$^1$H-NMR-based metabolic profiling was applied to track metabolic changes occurring in amniotic fluid and plasma of healthy mothers over the course of pregnancy. (Orczyk-Pawilowicz, et al, "Metabolomics of human amniotic fluid and maternal plasma during normal pregnancy," PLos ONE (2016) 11(4): e0152740). It is established that during the first two-thirds of gestation, the mother is in an anabolic condition. During the third trimester, intensive anabolic processes are occurring in the fetus, while maternal metabolism is switched towards catabolic activity. In AF, the transition from second to third trimester was associated with decreasing levels of glucose, carnitine, amino acids (valine, leucine, isoleucine, alanine, methionine, tyrosine, and phenylalanine) and increasing levels of creatinine, succinate, pyruvate, choline, N,N-dimethylglycine, and urocanate. In plasma, the progression from second trimester to third trimester was related to increasing levels of glycerol, choline and ketone bodies (3-hydroxybutyrate and acetoacetate), while pyruvate concentration was significantly decreased. Lactate to pyruvate ratio was decreased in AF and increased in plasma. The investigators concluded that these results are most likely related to the change in fetal growth dynamics, namely transition into a fast weight-gain phase, which requires considerably higher rates of anabolic processes. In contrast to plasma, the significant decrease in the levels of amino acids in AF is likely associated with fetal maturation and the increased demand for elementary building blocks necessary for protein synthesis.

Amniotic fluid and amniotic tissues contain numerous active biological molecules including proteins, lipids, carbohydrates, and electrolytes; some of which may function as enzymes, hormones, and growth factors. Growth factors are typically proteins that can have diverse biological effects but are characterized as trophic factors that can activate pro-growth cell signaling cascades. Several biologically relevant growth factors found in amniotic fluid include epidermal growth factor (EGF), transforming growth factor alpha (TGF-α), transforming growth factor beta (TGF-β), insulin-like growth factors (IGFs), and erythropoietin (EPO). Amniotic fluid also reduces scarring (Ozgenel G Y et al., J Neurosurg 2003; 98: 371-377), in part due to the presence of hyaluronic acid (Gao X et al., Ann Plastic Surg 1994; 33: 128-134).

Thus, amniotic tissue and amniotic fluid are a source of biological components that stimulate tissue repair and promote skin and connective tissue homeostasis. However, there is significant donor-to-donor variation in the molecular composition of amniotic tissue and fluid, and further it is not guaranteed that amniotic fluid will be safe for use, e.g. for therapeutic use, due to the possibility of infectious disease or maternal/fetal damage. In addition, it is unclear whether many important amniotic factors, such as but not limited to cytokines, growth factors and hyaluronic acid, survive the various processes used in the recovery and storage of amniotic fluid. Therefore, the inherent variability in amniotic tissue as well as the different collection and storage conditions is a challenge for standardizing and reproducing the efficacy of these products in a variety of therapeutic applications.

Thus, an important and unmet need remains for consistent amniotic tissue compositions. The presently disclosed subject matter provides such improved compositions, and methods of preparation and methods of use thereof.

SUMMARY

The present disclosure relates, in part, to methods for culturing amniotic epithelial cells (AECs) and amniotic fluid cells (AFs) to produce a conditioned media (e.g. a composition comprising components of amniotic fluid) with advantageous properties, and compositions comprising the same. The compositions comprising components of amniotic fluid described herein provide an advantage over amniotic fluid in that the described compositions can overcome the variability, safety and storage challenges found with amniotic fluid.

According to one aspect, the disclosure features a method for making a composition comprising components of amniotic fluid, the method comprising (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the conditioned supernatant is the composition comprising components of amniotic fluid. According to some embodiments, the AECs are attached to a surface of the culture system and the AFCs are deposited on top of the AECs. According to some embodiments, the AECs are attached to a surface of the culture system and the AFCs are deposited on top of the AECs. According to some embodiments, the AECs are mitotically inactivated prior to transferring to the cell culture system. According to some embodiments, mitotic inactivation is performed by treatment of the AECs with radiation. According to some embodiments, mitotic inactivation is performed by treatment of the cells with mitomycin C. According to some embodiments, mitomycin C is used at a concentration of 10 ug/ml in complete media for 2 h. According to some embodiments, the lipids comprise arachidonic acid, cholesterol, DL-alpha-tocopherol acetate, linoleic acid, linolenic acid, myristic acid, oleic acid, palmitic acid, palmitoleic acid, and stearic acid. According to some embodiments, the AECs and AFCs are expanded prior to transferring to the cell culture system by passaging the AECs and AFCs one, two or three times. According to some embodiments, the AECs and AFCs are derived from a mammalian tissue without having been previously frozen. According to some embodiments, the mammalian tissue is a human tissue.

According to another aspect, the disclosure features a method for making a composition comprising components of amniotic fluid, the method comprising (a) transferring at least one of cell types selected from the group consisting of: (i) amniotic fluid cells (AFCs), (ii) amniotic epithelial cells (AECs), (iii) placenta cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; and (d) ensuring the sterility of the conditioned supernatant, wherein the conditioned supernatant is the composition comprising components of amniotic fluid. According to some embodiments, the at least one of cell types (i)-(iv) are derived from a mammalian tissue without having been previously frozen. According to some embodiments, the mammalian tissue is a human tissue. According to some embodiments, the cell types consist of at least two of the cell types (i)-(iv). According to some embodiments, the cell types consist of at least three of the cell types (i)-(iv). According to some embodiments, the cell types consist of the four cell types (i)-(iv). According to some embodiments, the at least one of cell types (i)-(iv) are derived from a mammalian tissue without having been previously frozen. According to some embodiments, the mammalian tissue is a human tissue. According to some embodiments, the defined medium essentially free of serum consists of a base media; one or more of monothioglycerol, lipids, or polyvinyl alcohol; and, optionally, one or more antibiotics.

According to another aspect, the disclosure features a composition comprising components of amniotic fluid, wherein the composition is produced by a process comprising (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition comprising components of amniotic fluid. According to some embodiments, the AECs are attached to a surface of the cell culture system and the AFCs are deposited on top of the AECs. According to some embodiments, the AECs are mitotically inactivated prior to transferring to the cell culture system. According to some embodiments, mitotic inactivation is performed by treatment of the AECs with radiation. According to some embodiments, mitotic inactivation is performed by treatment of the cells with mitomycin C. According to some embodiments, the lipids comprise arachidonic acid, cholesterol, DL-alpha-tocopherol acetate, linoleic acid, linolenic acid, myristic acid, oleic acid, palmitic acid, palmitoleic acid, and stearic acid. According to some embodiments, the AECs and AFCs are expanded prior to transferring to the cell culture system by passaging the AECs and AFCs one, two or three or more times. According to some embodiments, the AECs and AFCs are derived from a mammalian tissue without having been previously frozen. According to some embodiments, the mammalian tissue is a human tissue.

According to another aspect, the disclosure features a method for preservation of an organ, the method comprising surrounding the organ in a composition comprising components of amniotic fluid set forth in any of the aspects and embodiments herein, wherein the organ is preserved in the composition. According to some embodiments, the organ is intended for use as a transplant organ.

According to another aspect, the disclosure features a topical composition for regulating skin condition, the composition comprising: i) a safe and effective amount of a composition comprising components of amniotic fluid; and ii) a carrier, wherein the composition comprising components of amniotic fluid is produced by a process comprising (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; (d) ensuring the sterility conditioned supernatant; and (e) one or both of concentrating the sterile conditioned supernatant and isolating one or more proteins, microvesicles/exosomes, nucleic acids, or lipids present in the total protein, wherein the one or both of concentrated conditioned supernatant and isolated proteins, microvesicles/exosomes, nucleic acids, or lipids are the composition comprising components of amniotic fluid. According to some embodiments, the AECs are attached to a surface of the cell culture system and the AFCs are deposited on top of the AECs. According to some embodiments, the AECs are mitotically inactivated prior to transferring to the cell culture system. According to some embodiments, mitotic inactivation is performed by treatment of the AECs with radiation. According to some embodiments, mitotic inactivation is performed by treatment of the cells with mitomycin C. According to some embodiments, the lipids comprise arachidonic acid, cholesterol, DL-alpha-tocopherol acetate, linoleic acid, linolenic acid, myristic acid, oleic acid, palmitic acid, palmitoleic acid, and stearic acid. According to some embodiments, the AECs and AFCs are expanded prior to transferring to the cell culture system by passaging the AECs and AFCs one, two or three or more times. According to some embodiments, the AECs and AFCs are derived from a mammalian tissue without having been previously frozen. According to some embodiments, the mammalian tissue is a human tissue. According to some embodiments, the topical composition further comprises from about 0.1 to about 20% of a moisturizing agent. According to some embodiments, the moisturizing agent comprises one or more of panthenol, pantothenic acid derivatives, glycerin, glycerol, dimethicone, petrolatum, hyaluronic acid, or ceramides, and mixtures thereof. According to some embodiments, the topical composition further comprises a vitamin B3 compound. According to some embodiments, the vitamin B3 compound comprises tocopherol nicotinate. According to some embodiments, the topical composition further comprises an anti-oxidant. According to some embodiments, the anti-oxidant comprises one or a combination of tocopherol or esters of tocopherol. According to some embodiments, the composition is in the form of a liquid, lotion, cream, gel, foam, mousse, spray, paste, powder, or solid. According to some embodiments, regulating skin condition includes one or more of inducing increased skin integrity by cell renewal; enhancing water content or moisture of skin; reducing trans epidermal water loss, skin flaking, and scaling; improving skin thickness; enhancing skin tensile properties; reducing the appearance of dermal fine lines and wrinkles; improving skin texture; reducing skin pores size; enhancing skin smoothness; improving skin age spots; improving skin tone; or improving the appearance of scars and skin abrasions. According to some embodiments, the components are present in concentrations effective to induce epithelial cells to undergo an epithelial-to-mesenchymal transition (EMT).

According to another aspect, the disclosure features a method for regulating a human skin condition which comprises applying to human skin at least once a day over at least seven days a topical composition according to any one of the aspects and embodiments herein. According to some embodiments, the method further comprises applying the topical composition to human skin at least twice a day over at least fourteen days.

According to another aspect, the disclosure features a method for tissue repair, the method comprising one of putting on, embedding into, filling, and injecting a tissue with a composition comprising components of amniotic fluid produced by a process comprising (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the tissue is repaired by the putting on, embedding into, filling, or injecting the tissue with the composition. According to some embodiments, the tissue comprises dermal, scar, cartilage, tendon, ligament, muscle, bone, periodontal, cardiovascular, hematologic, pulmonary, urologic, ophthalmic, liver, or kidney tissue, or combinations thereof. According to some embodiments, the tissue repair is selected from one or a combination of promotion of cell/tissue homeostasis, reduction of inflammation, wounds and burns, infection treatment, sepsis treatment, repair of scarring, preventing post-operative scarring, joint repair, rheumatoid arthritis treatment, psoriatic arthritis treatment, gout treatment, bursitis treatment, joint replacement surgery, tendon repair, tendinitis treatment, rotator cuff repair, muscle repair, repair, osteoarthritis treatment, arthritis treatment, male urologic dysfunction treatment, Critical Limb Ischemia treatment, Intermittent Claudication treatment, Buerger's Disease treatment, Ischemic Heart Disease treatment, Diastolic Heart Failure treatment, bronchopulmonary dysplasia, chronic obstructive pulmonary disease, ophthalmic disorders, and reversal of aging. According to some embodiments, the composition is a dermal, cartilage, or bone gel. According to some embodiments, the AECs are attached to a surface of the culture system and the AFCs are deposited on top of the AECs. According to some embodiments, the AECs are mitotically inactivated prior to transferring to the cell culture system. According to some embodiments, mitotic inactivation is performed by treatment of the AECs with radiation. According to some embodiments, mitotic inactivation is performed by treatment of the cells with mitomycin C. According to some embodiments, lipids comprise arachidonic acid, cholesterol, DL-alpha-tocopherol acetate, linoleic acid, linolenic acid, myristic acid, oleic acid, palmitic acid, palmitoleic acid, and stearic acid. According to some embodiments, the AECs and AFCs are expanded prior to transferring to the cell culture system by passaging the AECs and AFCs one, two or three times. According to some embodiments, the AECs and AFCs are derived from a mammalian tissue without having been previously frozen. According to some embodiments, the mammalian tissue is a human tissue.

According to another aspect, the disclosure features a method of inducing a cell to undergo an epithelial-to-mesenchymal transition (EMT), the method comprising steps of (a) providing the cell; and (b) contacting the cells with the composition set forth in any of the aspects and embodiments described herein. According to some embodiments, the cell is an epithelial cell. According to some embodiments, the cell is a progenitor cell. According to some embodiments, the cell is selected from the group consisting of hepatic progenitor (HP), hepatocyte-like cell (HLC), amniotic epithelial cell (AEC), AEC-derived cell and pluripotent stem cell (PSC)-derived cell. According to some embodiments, the cell is in an in vitro culture. According to some embodiments, the cell is isolated from the in vitro culture. According to some embodiments, the cell will be used in a transplantation procedure.

According to another aspect, the disclosure features a method for preparing progenitor cells from epithelial cells, the method comprising the steps of: (a) providing a population of epithelial cells; and (b) inducing EMT in the population of epithelial cells by the method of any of the aspects and embodiments herein, whereby progenitor cells are generated in the population. According to some embodiments, the method further comprises isolating progenitor cells from the population after inducing EMT.

BRIEF DESCRIPTION OF THE DRAWINGS

FIG. 2A is an image of amniotic epithelial cells (AECs) stained with an antibody recognizing SSEA4 according to one or more embodiments of the present disclosure (scale bar denotes 100 µm).

FIG. 2B is an image of AECs stained with DAPI according to one or more embodiments of the present disclosure (scale bar denotes 100 µm).

FIG. 2C is an image of amniotic fluid cells (AFCs) stained with an antibody recognizing SSEA4 according to one or more embodiments of the present disclosure (scale bar denotes 100 µm).

FIG. 2D is an image of AFCs stained with DAPI according to one or more embodiments of the present disclosure (scale bar denotes 100 µm).

FIG. 6 is a table showing analysis by Bradford assay and LC-MS/MS of conditioned SFM1 produced according to the method illustrated in FIG. 4 according to one or more embodiments of the present disclosure. Unconditioned SFM1 (SFM1), the co-AC conditioned SFM1 (co-AC), the AEC conditioned SFM1 (AEC), and the AFC conditioned SFM1 (AFC) were measured for total protein concentration using the Bradford method or the proteome analyzed by liquid chromatography-tandem mass spectrometry (LC-MS/

MS) to determine unique proteins present in each sample and the percent of proteins per sample relative to all proteins identified in each of the 4 groups assayed.

Figure 7:
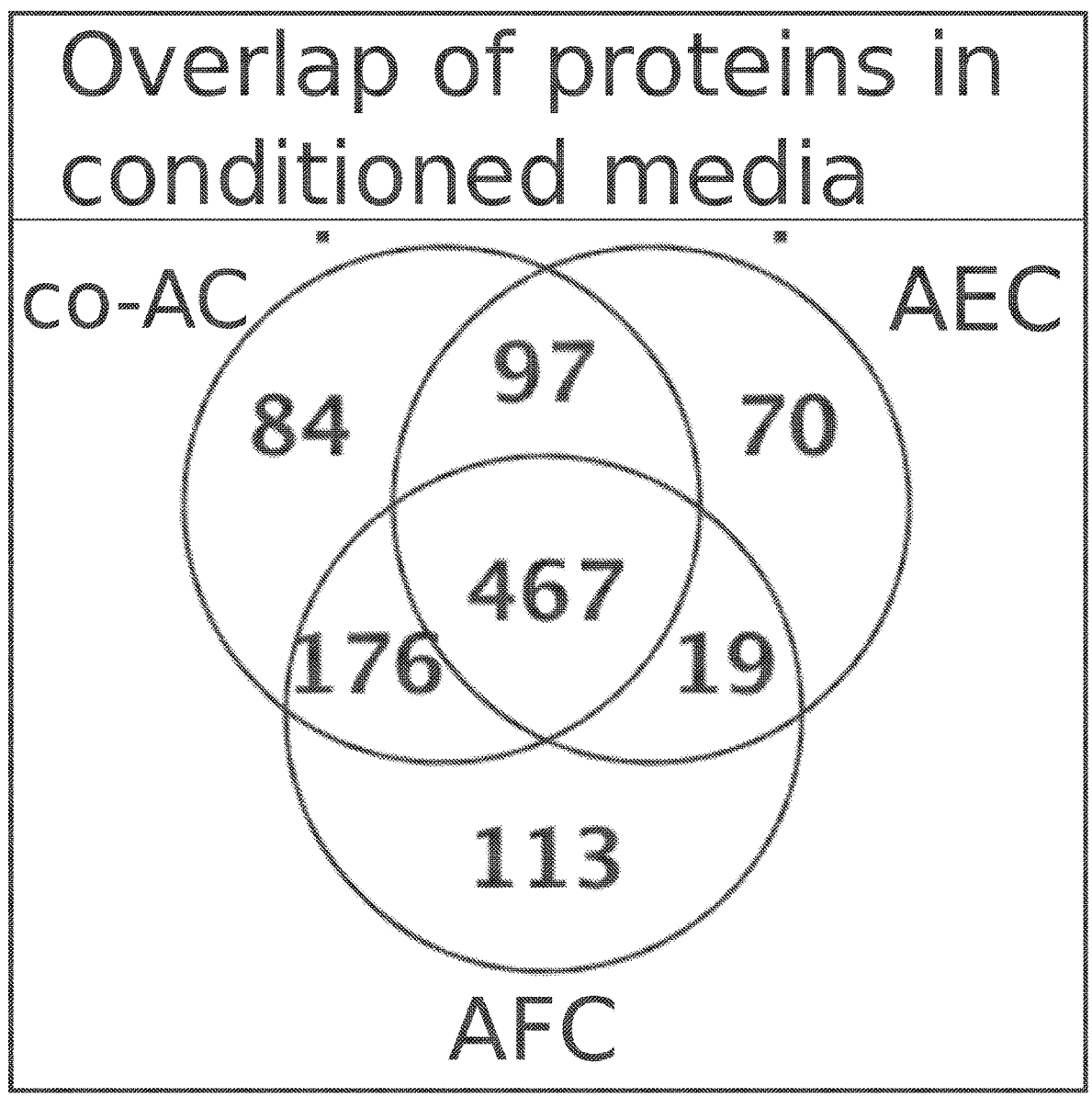

FIG. 7 is a Venn diagram of the LC-MS/MS data reported in FIG. 6 showing the overlap or distinct proteins (by identity) secreted into SFM1 using AFCs, AECs, or co-ACs cultured. The analysis indicates that the co-culture of the AECs and AFCs in the SFM1 media yields 84 unique proteins not identified in either the AEC- or AFC-alone conditioned SFM1 according to one or more embodiments of the present disclosure.

Figure 4:
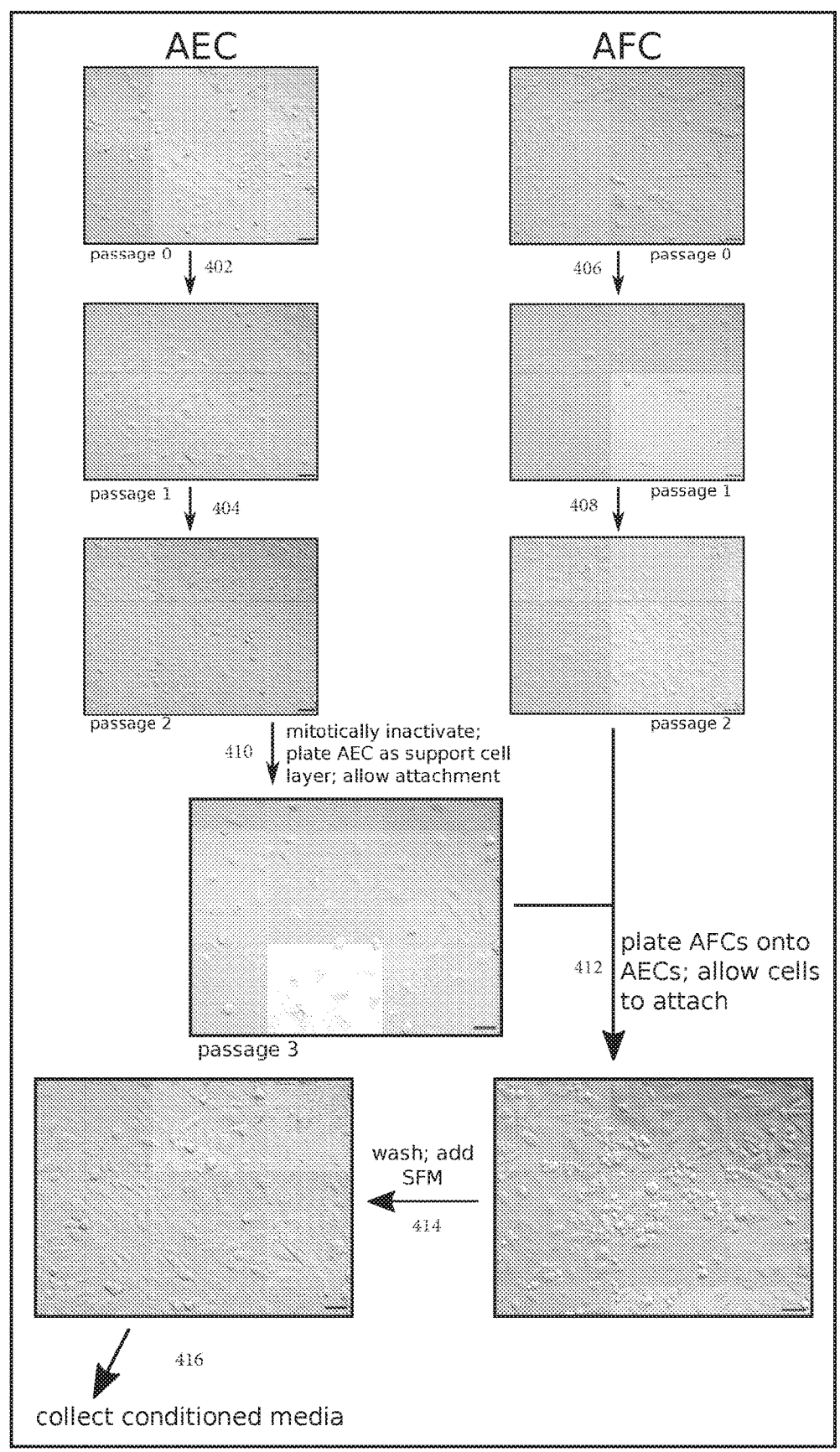
FIG. 4 is a flow diagram showing methods for making compositions comprising components of amniotic fluid according to one or more embodiments of the present disclosure (scale bar denotes 50 µm in each image).

FIG. 8 is a table showing the quantitative amounts of the numbers and percentages of proteins identified by LC-MS/MS in the conditioned SFM1 from the co-culture of the AECs and AFCs according to the method illustrated in FIG. 4 according to one or more embodiments of the present disclosure. The first row is proteins quantities measured by normalized total spectral counts for the co-culture of the AECs and AFCs in SFM1 that are greater than zero (co-AC>0); the second row is proteins detected in co-AC after subtracting the background proteins present in unconditioned SFM1 (co-AC>BG), the third row is proteins whose level measured in co-AC is higher than background proteins plus proteins identified in AEC alone-conditioned SFM1 (co-AC>(BG+AEC)), the fourth row is proteins whose level measured in co-AC is higher than background proteins plus proteins identified in AFC alone-conditioned SFM1 (co-AC>(BG+AFC)), and the fifth row is proteins whose level measured in co-AC is higher than background proteins plus proteins identified in AEC alone-conditioned SFM1 plus proteins identified in AFC alone-conditioned SFM1 (co-AC>(BG+AEC+AFC)). For all protein level analyses above, normalized spectral count values of co-AC were used to subtract normalized spectral count values from the other comparative groups (AEC only, AFC only, and AEC plus AFC).

Figure 9:
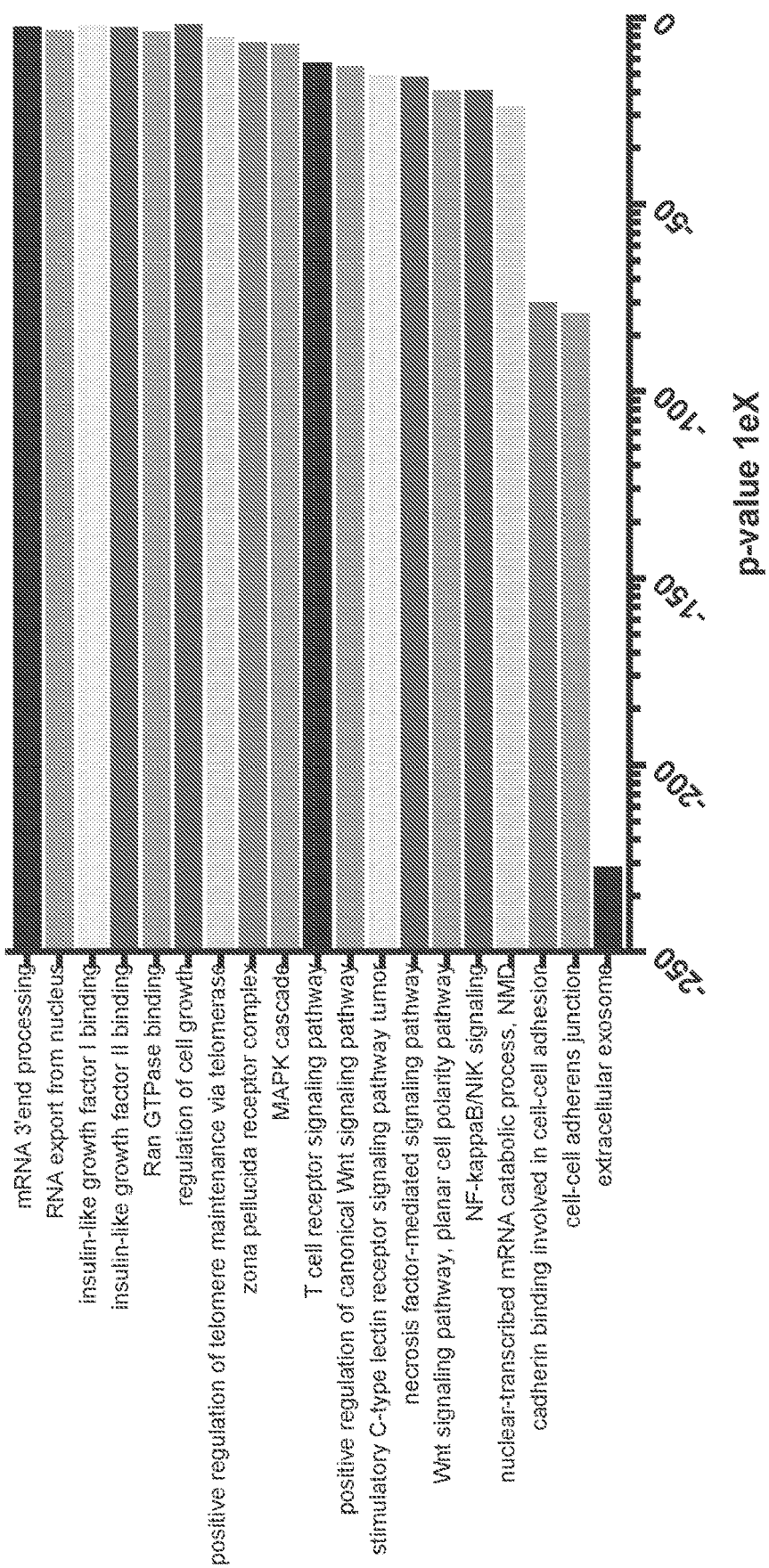

FIG. 9 is a bar graph showing the gene ontology (GO) term analysis identifying significantly enriched biological pathways from protein groups identified in the conditioned SFM1 from the co-culture of the AECs and AFCs according to the method illustrated in FIG. 4 according to one or more embodiments of the present disclosure. LC-MS/MS data from the conditioned SFM1 was compared to unconditioned SFM1 LC-MS/MS data (input as background data set) to derive significantly enriched ($p \leq 0.05$) GO terms. Selected GO terms are shown on the Y-axis and p-values are plotted on the X-axis as 1 eX with X being the value shown on the X-axis.

Figure 10:
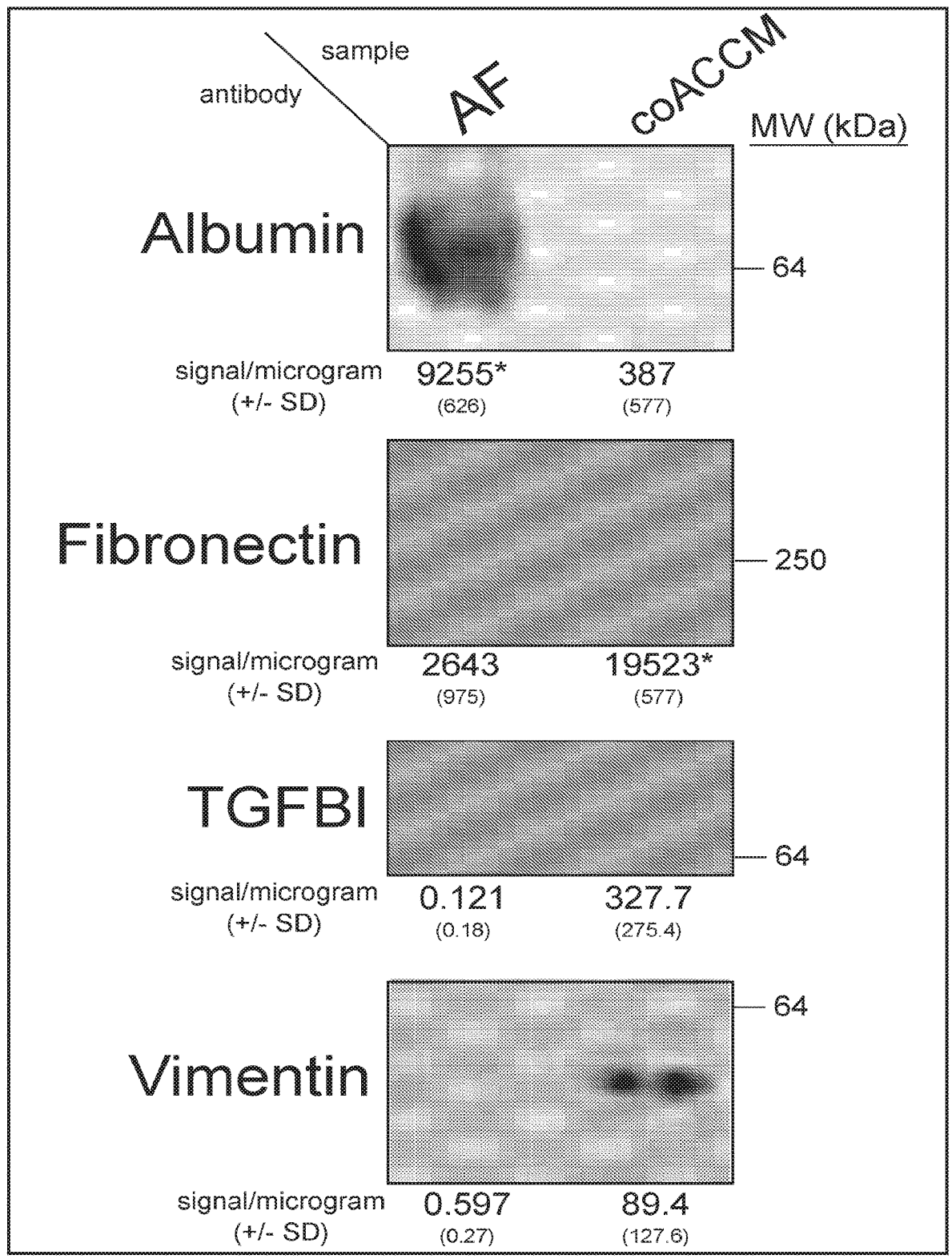
Figure 11A:
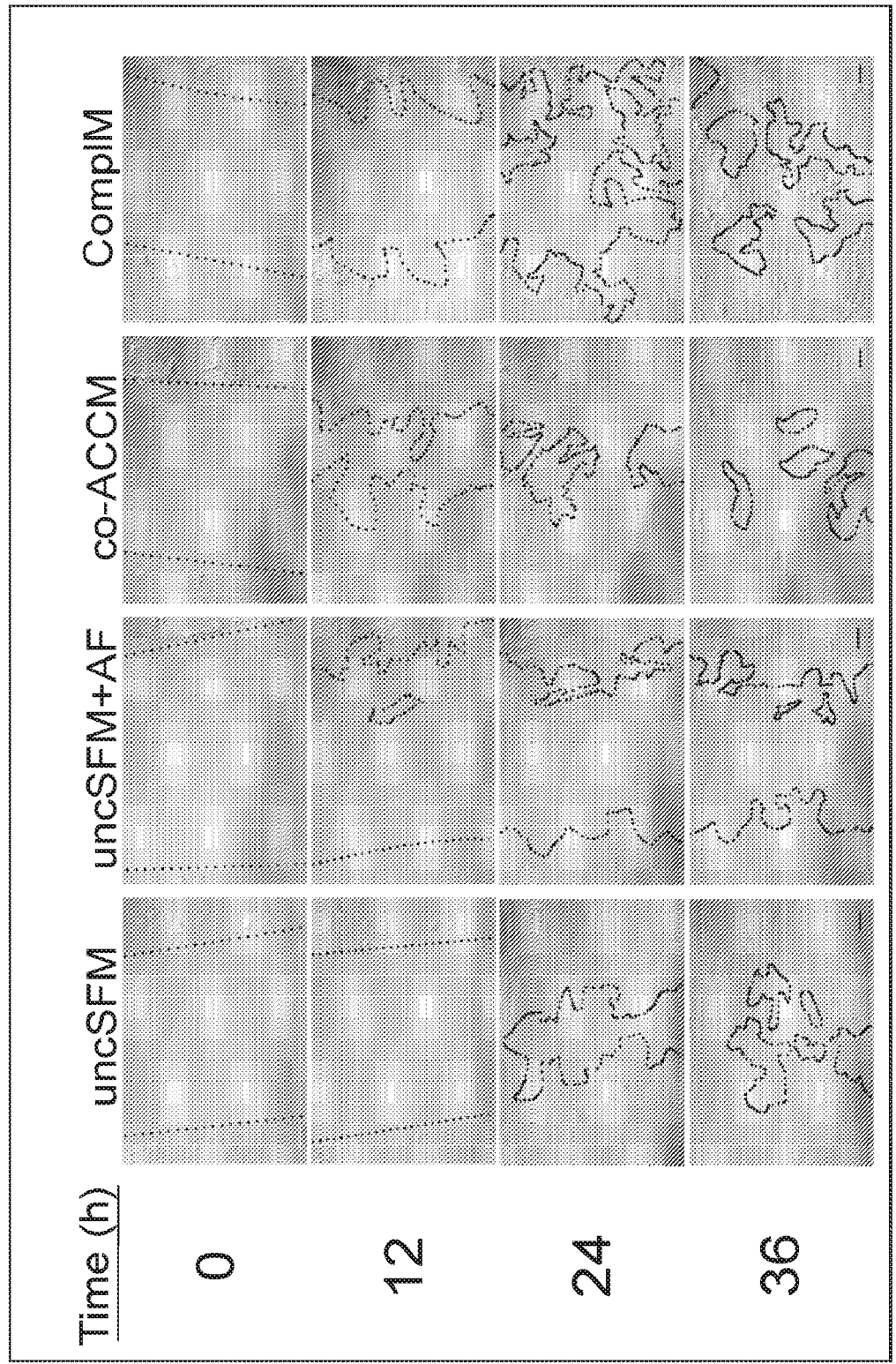

FIG. 10 shows a Western blot comparing protein presence and abundance between amniotic fluid (AF) and coACCM. Protein level was determined by Bradford method relative to bovine serum albumin and 7 micrograms total protein was loaded per well on 8% SDS-PAGE for AF and ~1 microgram total protein loaded for coACCM, each in biological triplicate. Nitrocellulose membranes were probed with the indicated primary antibody, then visualized on Odyssey CLx using infrared imaging of infrared-conjugated secondary antibodies. Mean protein signal per microgram of protein loaded is shown below, +/− standard deviation (*$P<0.01$ by student's t-test). These results demonstrate that the composition of AF vs. coACCM is markedly different FIG. 11A and FIG. 11B show the results of ScratchTest experiments. FIG. 11A shows brightfield microscopy (20× objective) showing representative images of C2C12 myoblasts during scratch test wound healing assay at time (hours) 0, 12, 24, and 36 incubated with unconditioned serum-free media (uncSFM), unconditioned serum-free media+10% amniotic fluid (uncSFM+AF), co-cultured amniotic cell conditioned media (co-ACCM), or complete media (ComplM; DMEM+10% FBS). Dotted lines outline areas not occupied by cells; scale bar denotes 50 µm. FIG. 11B shows quantitation of scratch area (in pixels) in conditions described in FIG. 11A. Area was calculated using ImageJ software and three independent replicates for each condition and timepoint were measured. Each datapoint shows the mean area value in pixels, +/−standard deviation (*$P \leq 0.05$ by student's t-test, relative to uncSFM; additionally all P for co-ACCM were $\leq 0.005$ relative to uncSFM+AF, except for 0 h timepoint, by student's t-test). These results demonstrate that coACCM elicits a significantly different biological effect/cell phenotype than the "natural product" (AF).

Figure 12A:
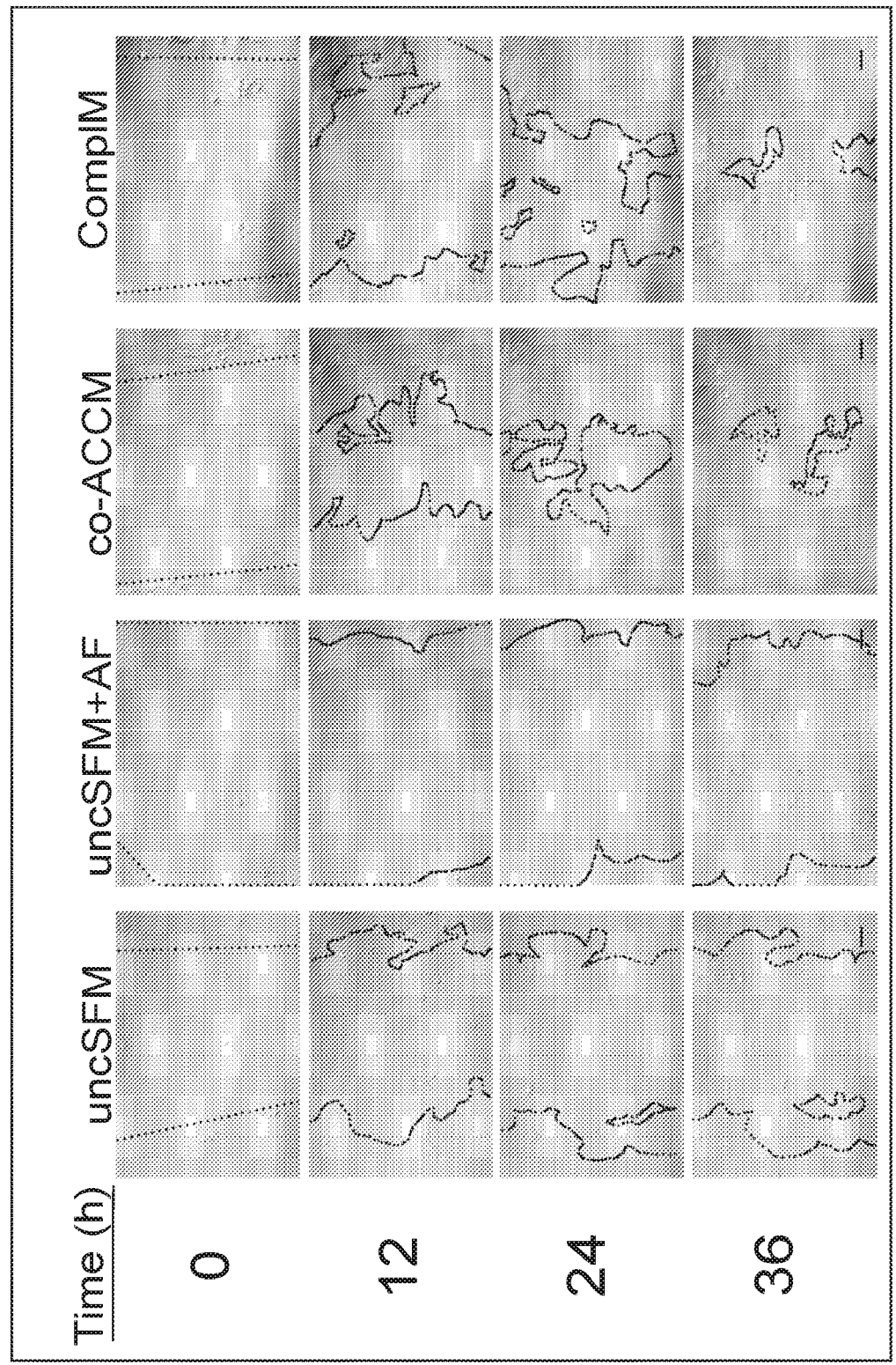
Figure 12B:
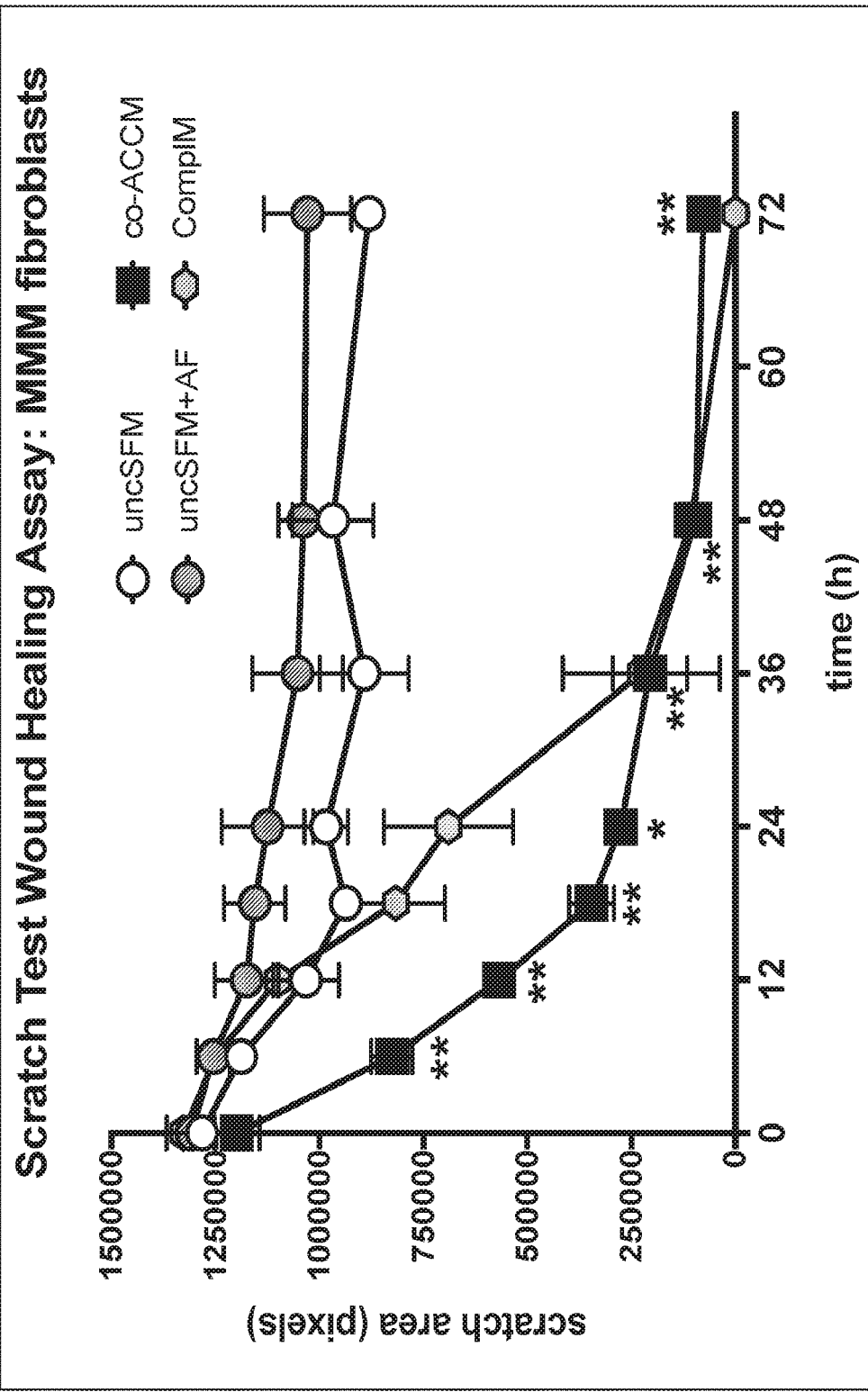

FIG. 12A shows the results of ScratchTest experiments. FIG. 12A shows brightfield microscopy (20× objective) showing representative images of MMM fibroblasts during scratch test wound healing assay at time (hours) 0, 12, 24, and 36 incubated with unconditioned serum-free media (uncSFM), unconditioned serum-free media+10% amniotic fluid (uncSFM+AF), amniotic cell co-culture conditioned media (co-ACCM), or complete media (ComplM; DMEM+10% FBS). Dotted lines outline area not occupied by cells; scale bar denotes 50 µm. FIG. 12B shows quantitation of scratch area (in pixels) in conditions described in A. Area was calculated using ImageJ software and three independent replicates for each condition and timepoint were measured. Each datapoint shows the mean area value in pixels, +/− standard deviation (*$P \leq 0.005$ or **$P \leq 0.001$ by student's t-test, relative to uncSFM; additionally all P for co-ACCM were $\leq 0.001$ relative to uncSFM+AF, except for 0 h timepoint, by student's t-test). This results indicates that coACCM elicits a significantly different biological effect/cell phenotype than the "natural product" (AF)

Figure 13A:
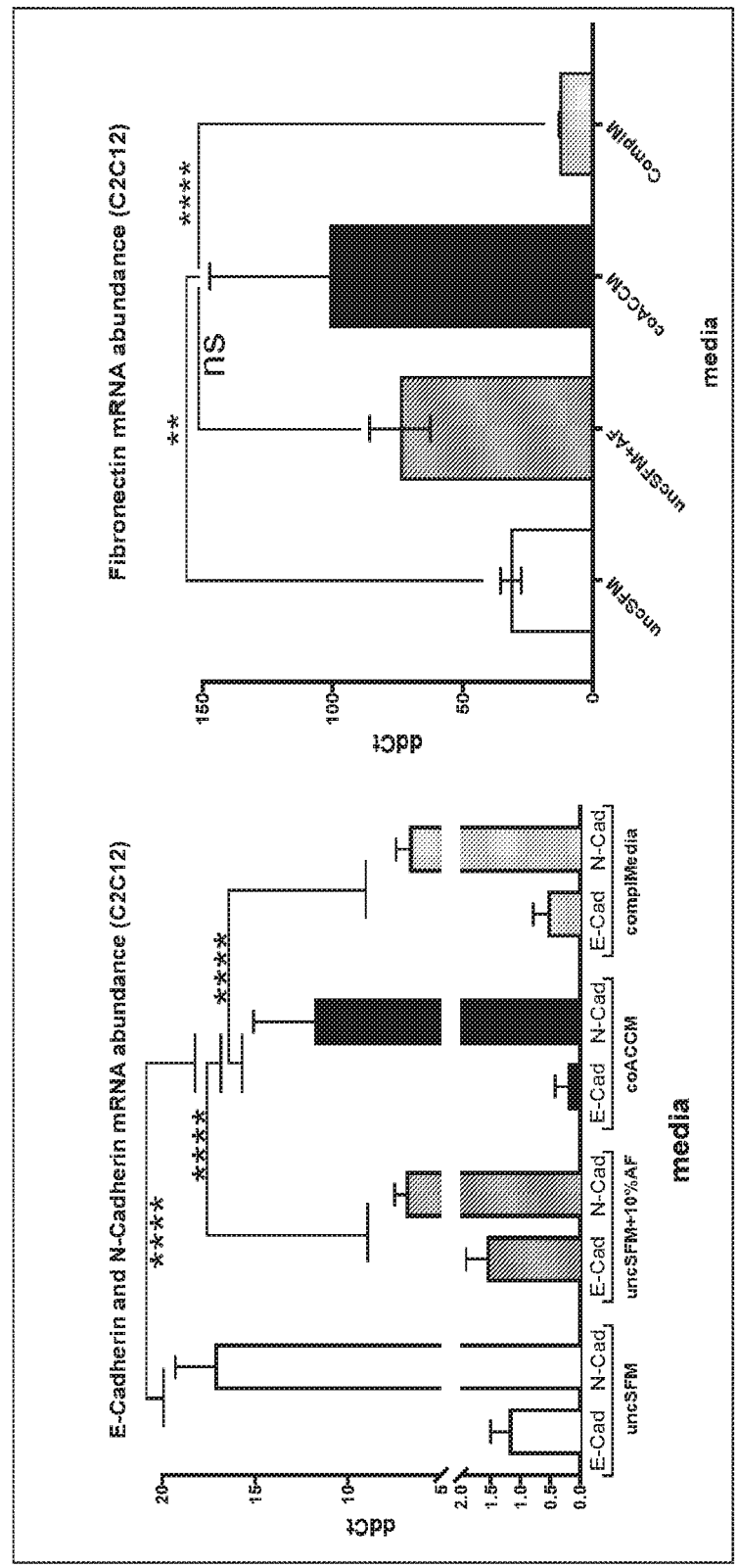
Figure 13B:
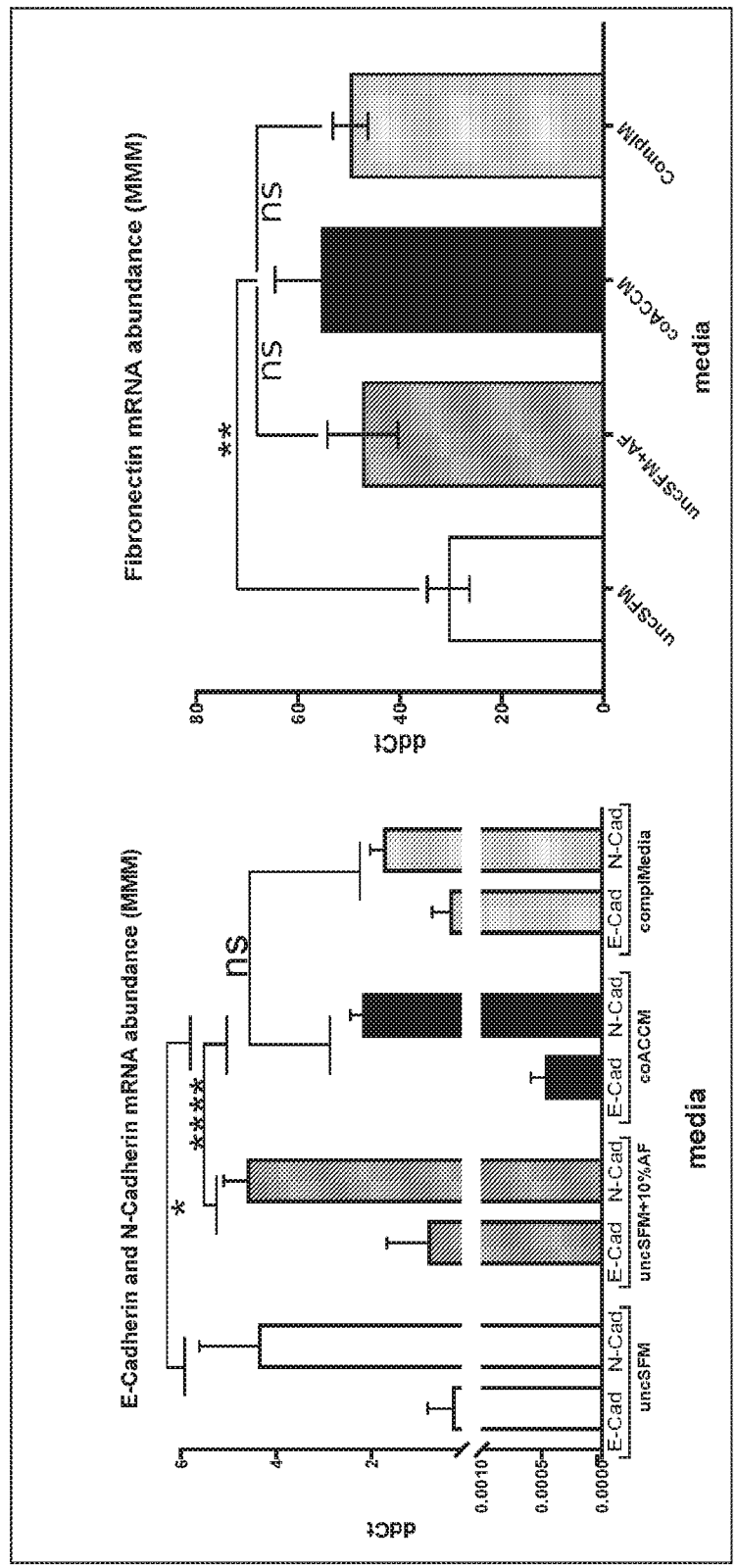

FIG. 13A shows results of qPCR for various epithelial-to-mesenchymal transition (EMT) genes. Following 72 h incubation in respective media type for scratch test assays, RNA was extracted from C2C12 myoblasts, reverse transcribed, then mRNA abundances were measured to determine level relative to hydroxymethylbilane synthase (housekeeping gene). Left panel shows the relative abundances of E-Cadherin (E-Cad) and N-Cadherin (N-Cad), and right panel shows the relative abundance of fibronectin. Ordinary one-way ANOVA was used to measure statistically significant differences, with ns=not significant, *$P \leq 0.05$, $P \leq 0.01$, *$P \leq 0.001$, ****$P \leq 0.0001$ denoting results. FIG. 13B shows results from the same experiments performed in FIG. 13A, but performed with MMM cells. EMT biomarkers are an increase in N-Cad with concomitant decrease in E-Cad, and an up-regulation of fibronectin. Mesenchymal-to-epithelial transition (MET) is measured in the opposite. Thus, these results show that coACCM appears to activate EMT, while AF activates MET. Additionally, these results indicate coACCM elicits a different biological effect/molecular phenotype than the "natural product" (AF).

Figure 14A:
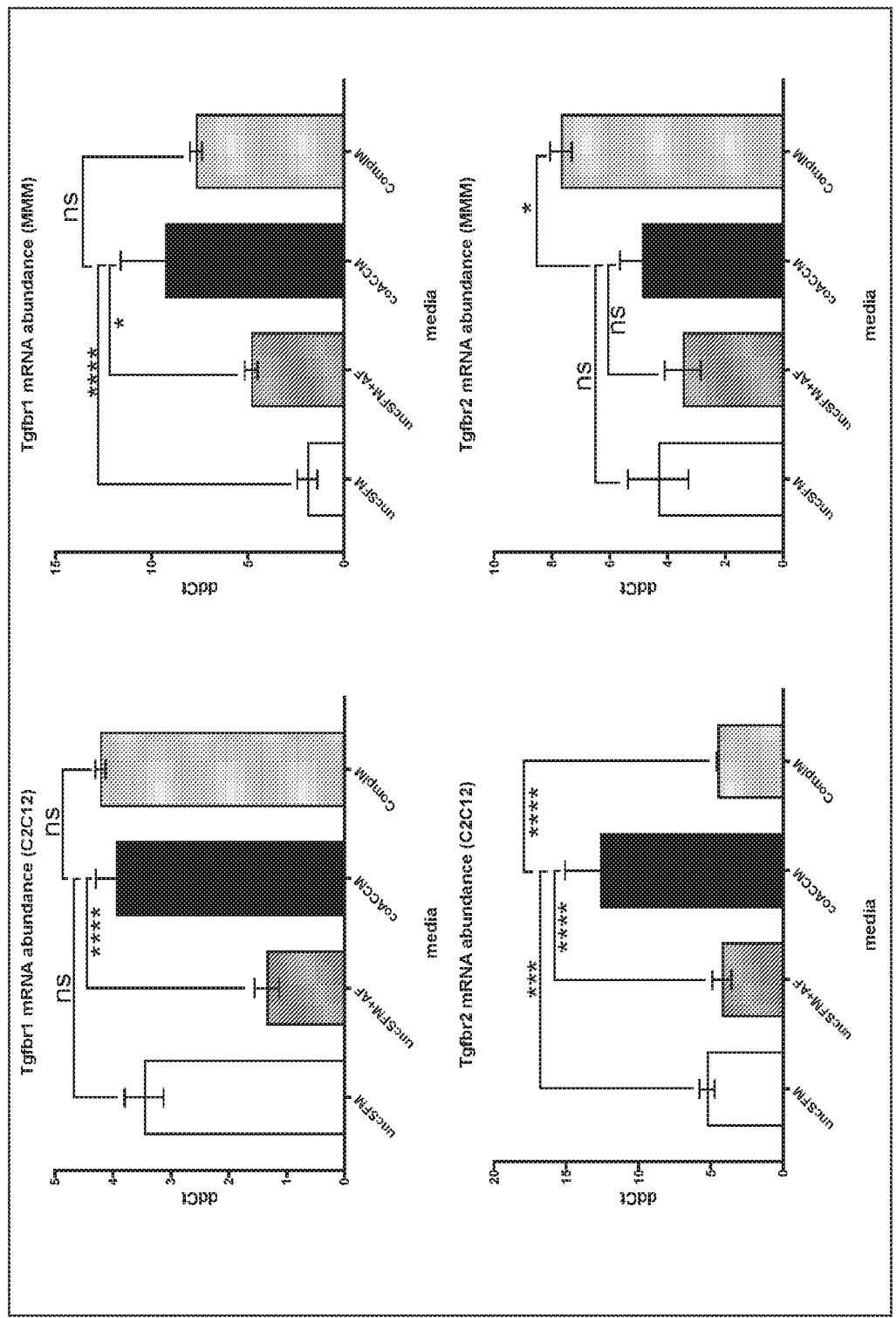
Figure 14B:
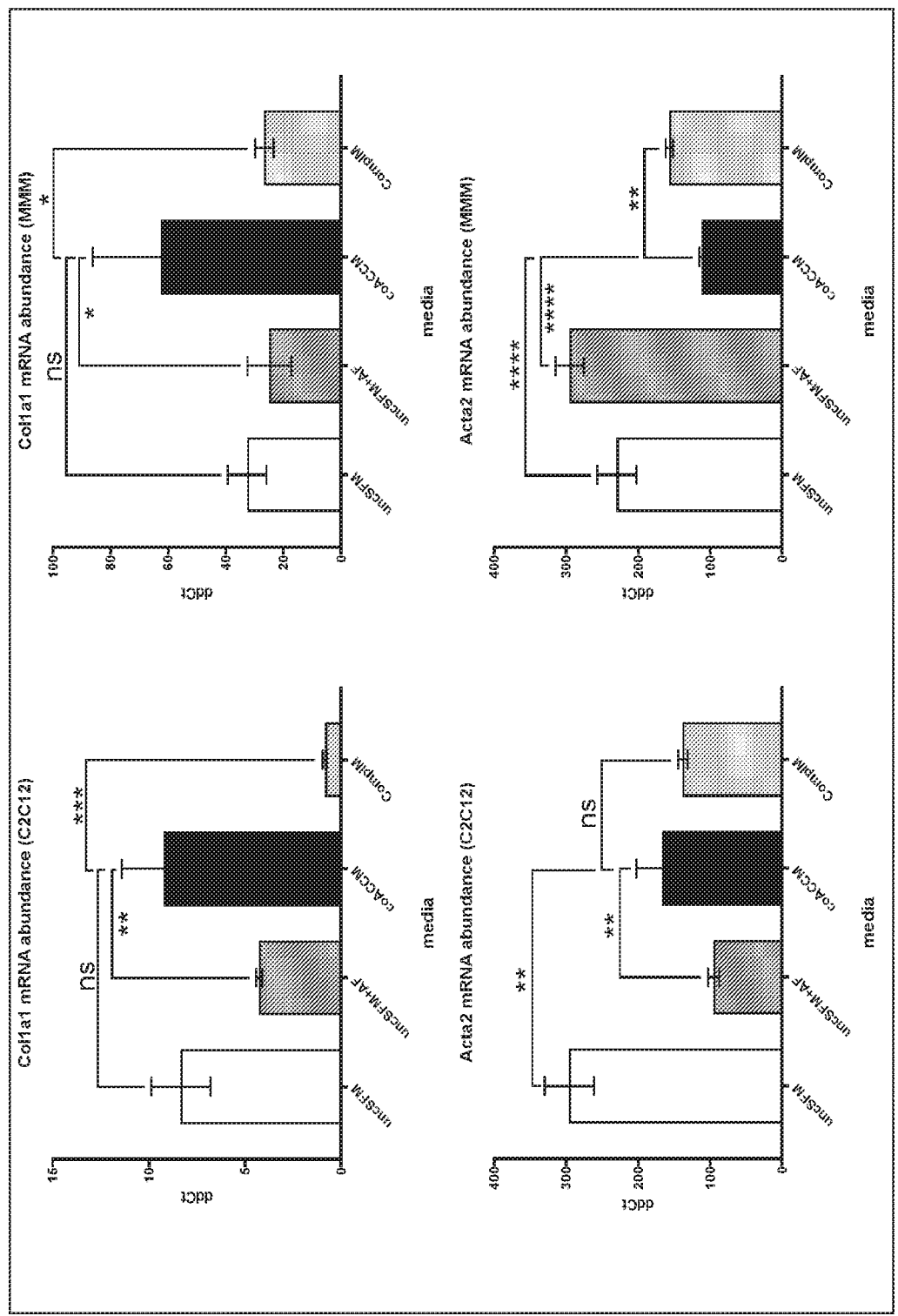

FIG. 14A shows the results of qPCR for Tgfb-Col-Acta2. Following 72 h incubation in respective media type for scratch test assays, RNA was extracted from C2C12 myoblasts (left column) or MMM fibroblasts (right column), reverse transcribed, then mRNA abundances were measured to determine level relative to hydroxymethylbilane synthase (housekeeping gene). Top row shows the relative abundances of TGF-beta receptor1 (Tgfbr1) and bottom TGF-beta receptor2 (Tgfbr2). Ordinary one-way ANOVA was used to measure statistically significant differences, with ns=not significant, *$P \leq 0.05$, $P \leq 0.01$, *$P \leq 0.001$,

****P≤0.0001 denoting results. FIG. 14B shows results from the same experiments performed in FIG. 14A, where type I collagen (Col1a1; top row) or smooth muscle actin (Acta2; bottom row) were measured. Tgf-beta signaling activity can be measured by an up-regulation of Tgfbr1 or Tgfbr2 (Kleef and Korc J B C 1998). Thus, without being bound by theory, these results suggest that EMT may be induced by coACCM through this pathway. Increase in Tgfbr1 indicates enhanced cooperative signaling, while increased Tgfbr2 direct ligand binding. Increased Acta2 indicates an increase in fibrosis, which is usually associated with poor healing outcomes and excessive scarring. Increased Col1a1 can be beneficial in cosmetic applications (increased collagen production), and can indicate ECM remodeling/cell activation in wound healing; it may be beneficial to downregulate collagen in late wound healing events, though. Additionally, this indicates coACCM elicits a different biological effect/molecular phenotype than the "natural product" (AF).

Figure 15A:
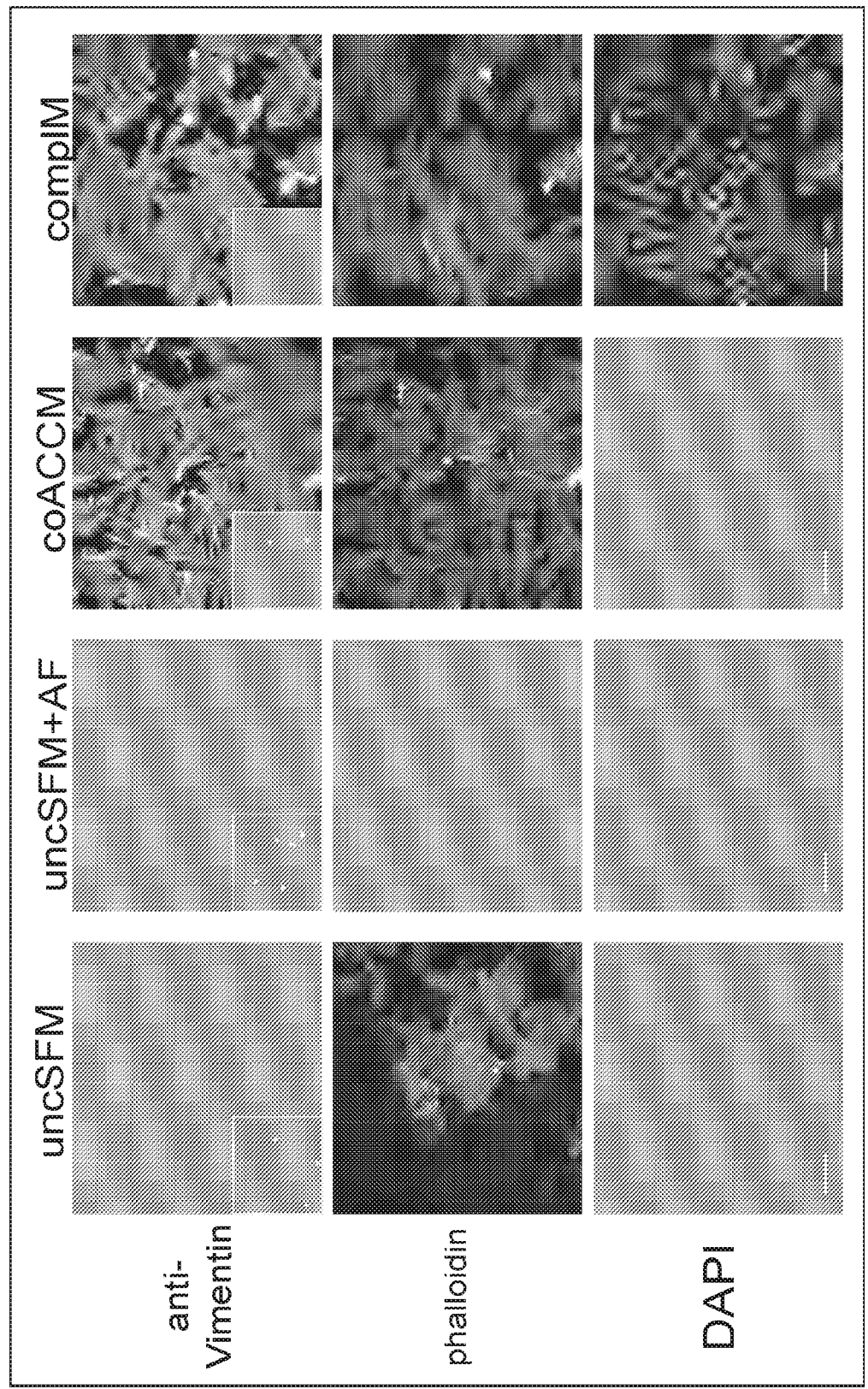
Figure 15B:
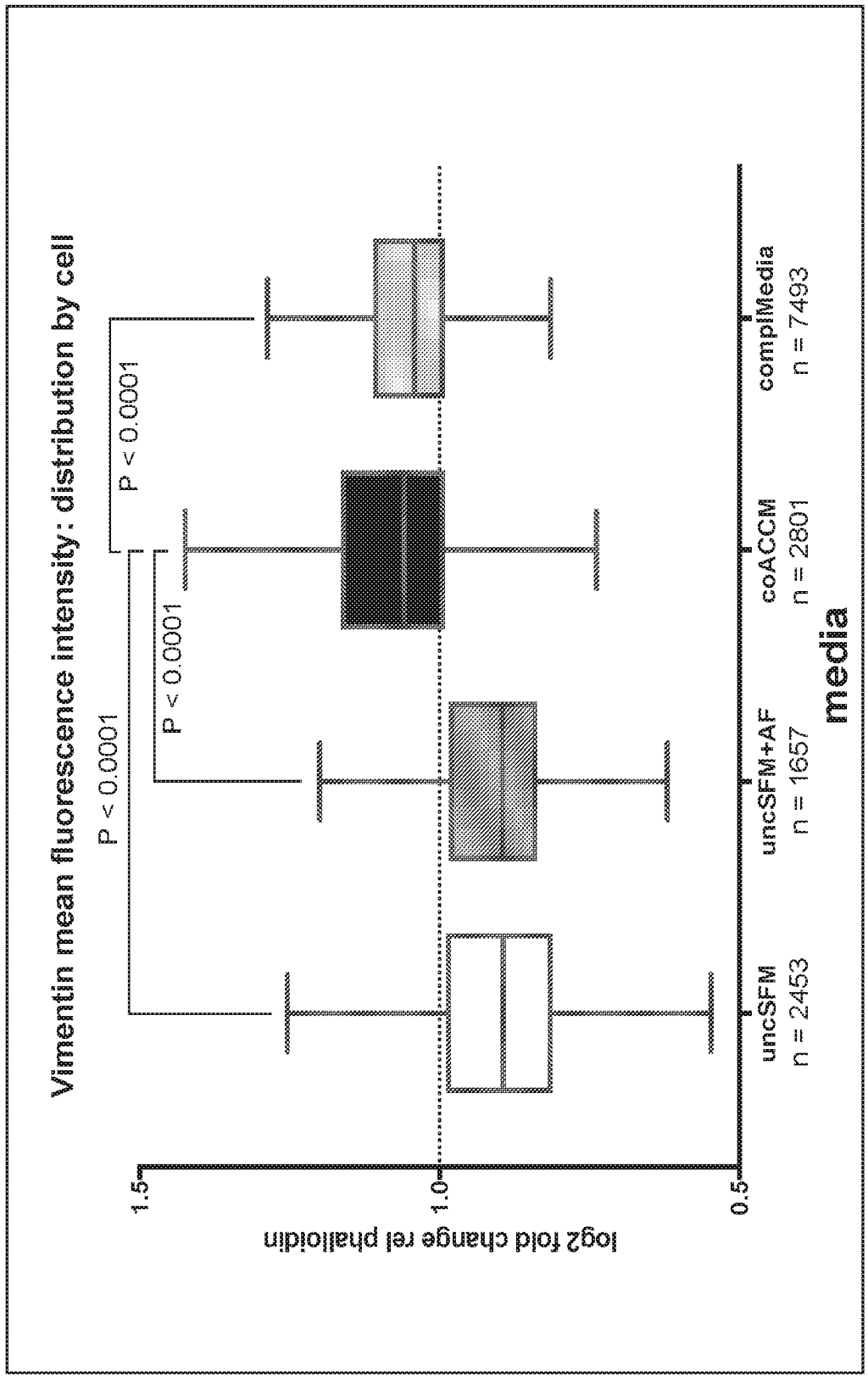

FIG. 15A shows indirect immunofluorescence imaging of C2C12 cells incubated with uncSFM, uncSFM+AF, coACCM, or complM for 24 h, and then stained with anti-Vimentin antibody, phalloidin, and DAPI. Representative images shown collected using 20× objective on Opera Phenix High Content Screening Microscope (Perkin Elmer); scale bar denotes 100 μm and inset region shows zoomed-in image with arrowheads indicating perinuclear vimentin localization. In FIG. 15B, using images collected as described above, the $\log_2$ fold-change in vimentin relative to phalloidin was calculated for each cell recorded (see cell number "n" below x-axis labels) and its distribution plotted using the Tukey box plot method. P-values were calculated using the Mann-Whitney non-parametric test for statistical significance. This is both a qualitative (A) and quantitative (B) assessment of vimentin (an EMT biomarker) protein. Increased total vimentin is a well-established indicator of EMT, and perinuclear aggregation/localization of vimentin is correlated with microtubule inhibition/inactivation (Goldman 1971), decreased cell motility (Mendez et al 2010), and reduced organelle movement (Chang et al 2009). Additionally, this indicates coACCM elicits a different biological effect/molecular phenotype than the "natural product" (AF).

Figure 16:
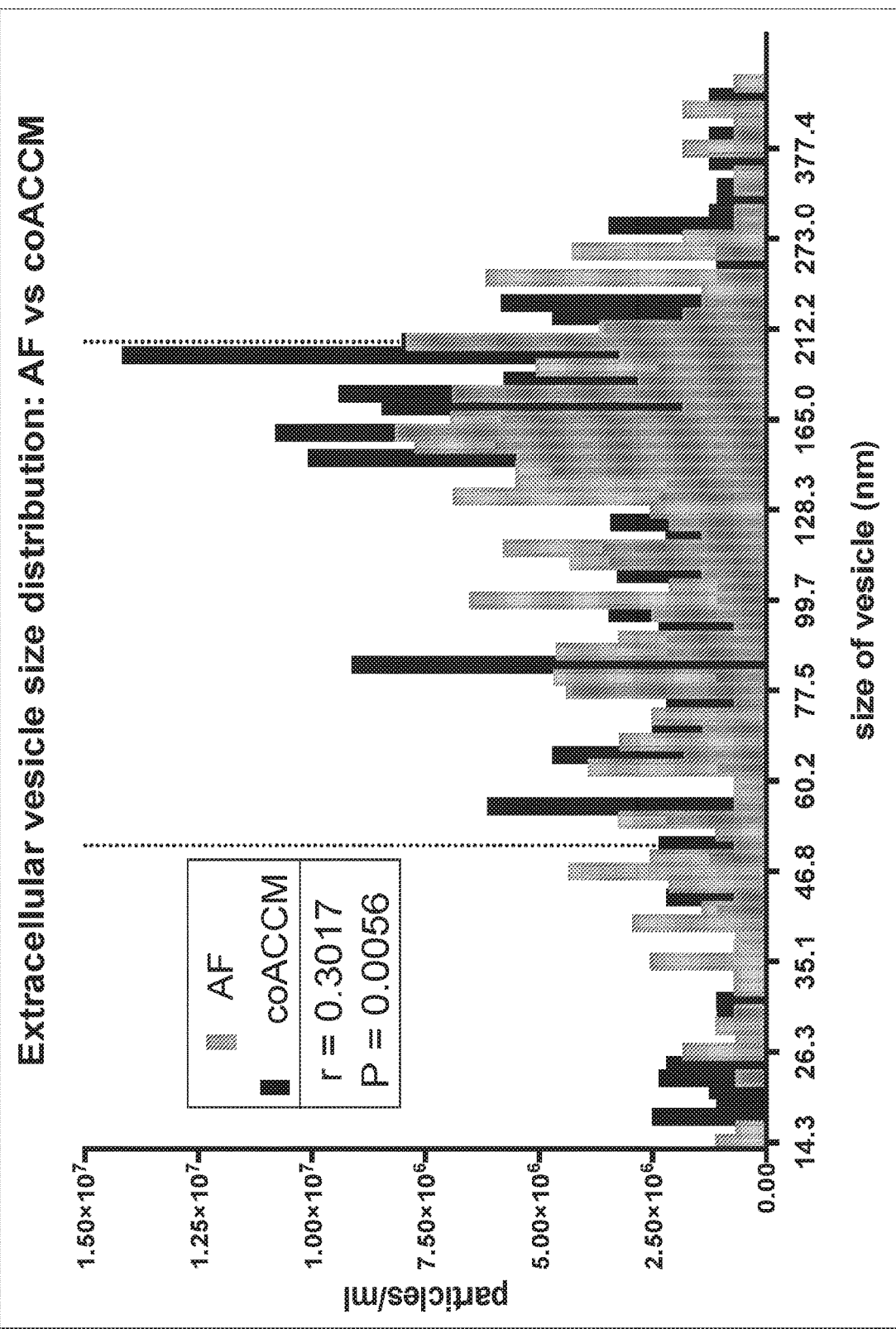

FIG. 16 shows a size distribution histogram of extracellular vesicles. The size and concentration of extracellular vesicles from coACCM and AF were measured using the ZetaSizer PMX-120 (Malvern), then the number of particles measure per milliliter (y-axis) were plotted relative to the size of the vesicles (x-axis). Dashed vertical lines demarcate sizes of 50-200 nm. Data were analyzed using the Spearman correlation and r value and P value are shown in legend. The size range of ~50-200 nm is generally recognized to be the size range of "exosomes". These results indicate coACCM is considerably different from the natural product (AF) by composition.

Figure 17:
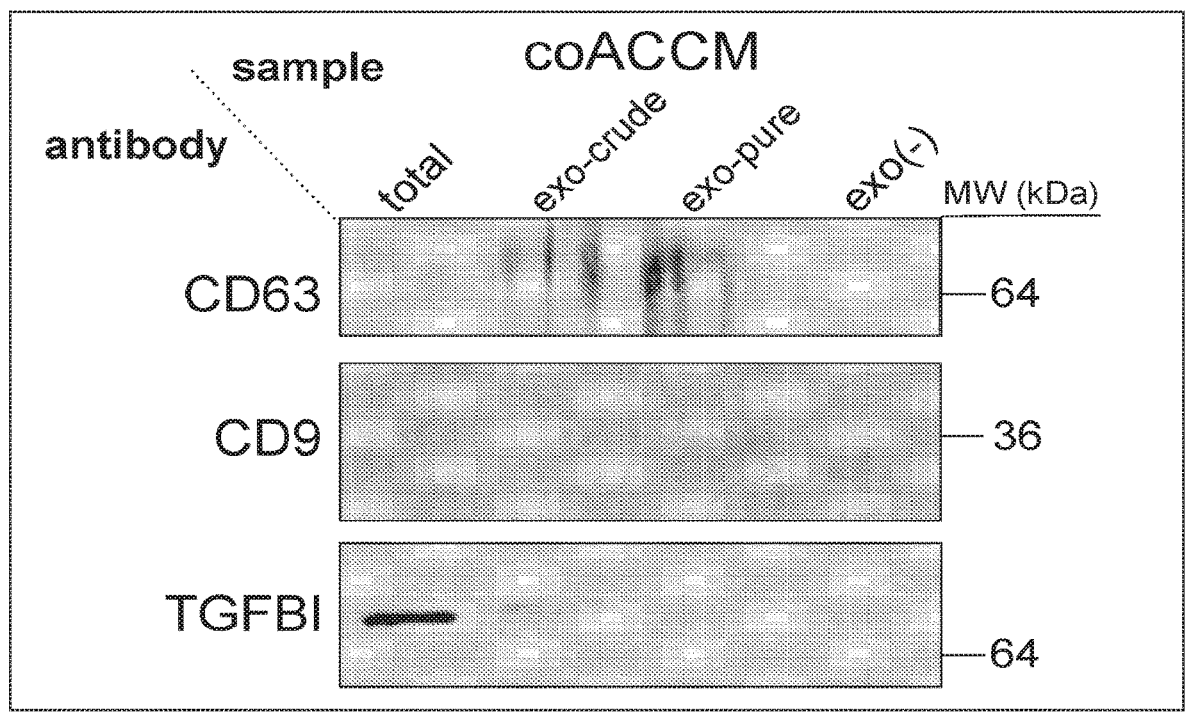

FIG. 17 shows the results of Western blot analysis of exosome markers and TGFBI in total coACCM (total), crude exosomal fraction from ExoQuick TC-ULTRA kit (SBI Biosciences) initial centrifugation step (exo-crude), purified exosomes eluted from column on final purification step from ExoQuick TC-ULTRA kit (SBI Biosciences; exo-pure), and exosome-depleted coACCM (exo(−)). Blots were probed with antibodies directed toward CD63 (top), CD9 (middle), and TGFBI (bottom), with molecular weight (MW) markers indicated in kilodaltons (kDa) at right. CD63 and CD9 are used as exosome biomarkers; TGFBI is included to show it likely is exosome-bound.

Figure 18B:
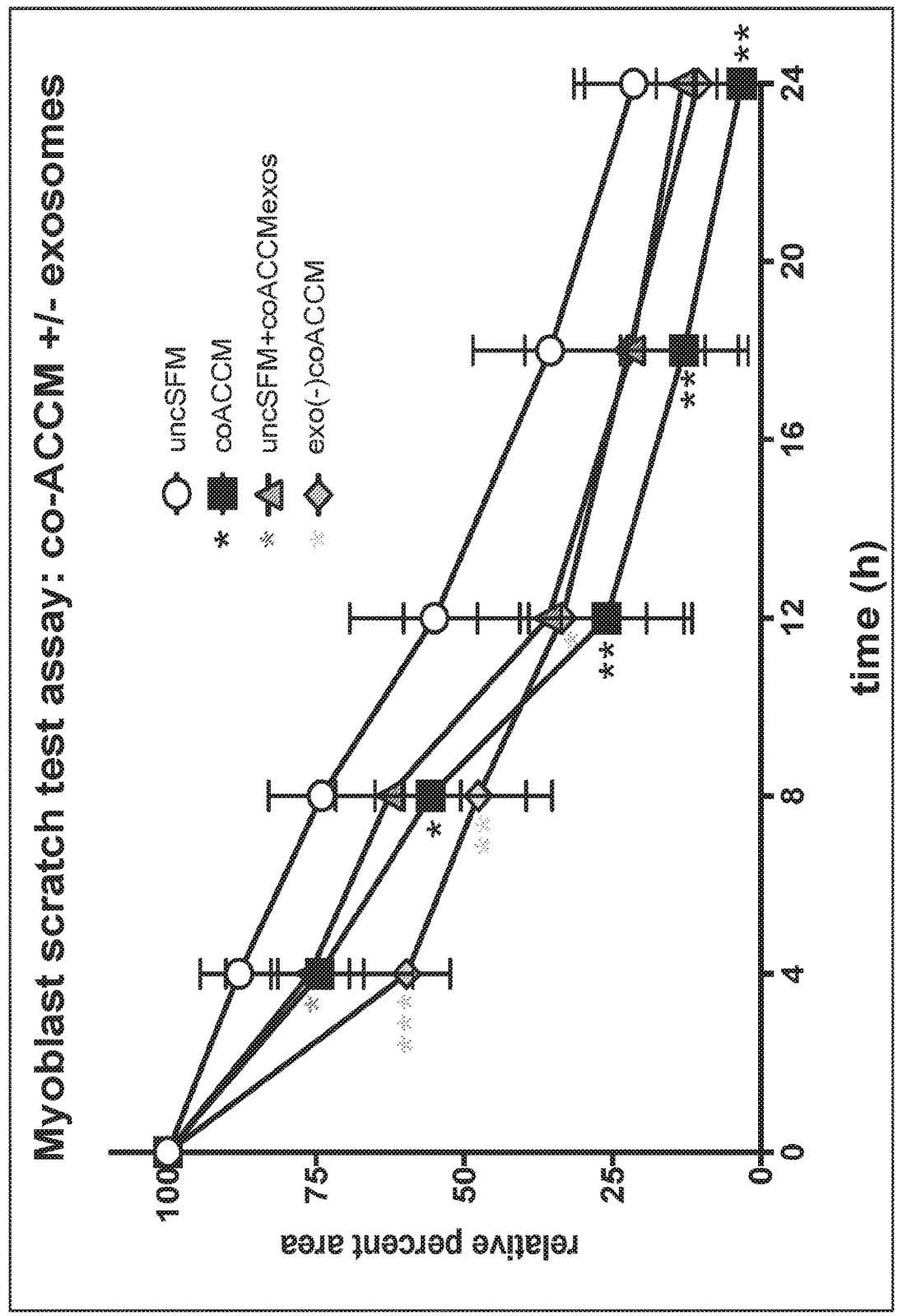

FIG. 18A shows brightfield microscopy (20× objective) showing representative images of C2C12 myoblasts during scratch test wound healing assay at time (hours) 0, 12, and 24 incubated with uncSFM, coACCM, uncSFM plus an equal quantity of exosomes derived from coACCM as in an equal volume to total coACCM (uncSFM+coACCMexos), or coACCM depleted of exosomes (exo(−) coACCM). Dotted lines outline area not occupied by cells; scale bar denotes 50 μm. FIG. 18B shows quantitation of scratch area displayed as percent area relative to measured scratch area at time zero in conditions described in A. Area was calculated using ImageJ software and three independent replicates for each condition and timepoint were measured. Each datapoint shows the mean relative percent area, +/− standard deviation (*P≤0.05 by student's t-test, P≤0.01, *P≤0.001 relative to uncSFM).

Figure 19:
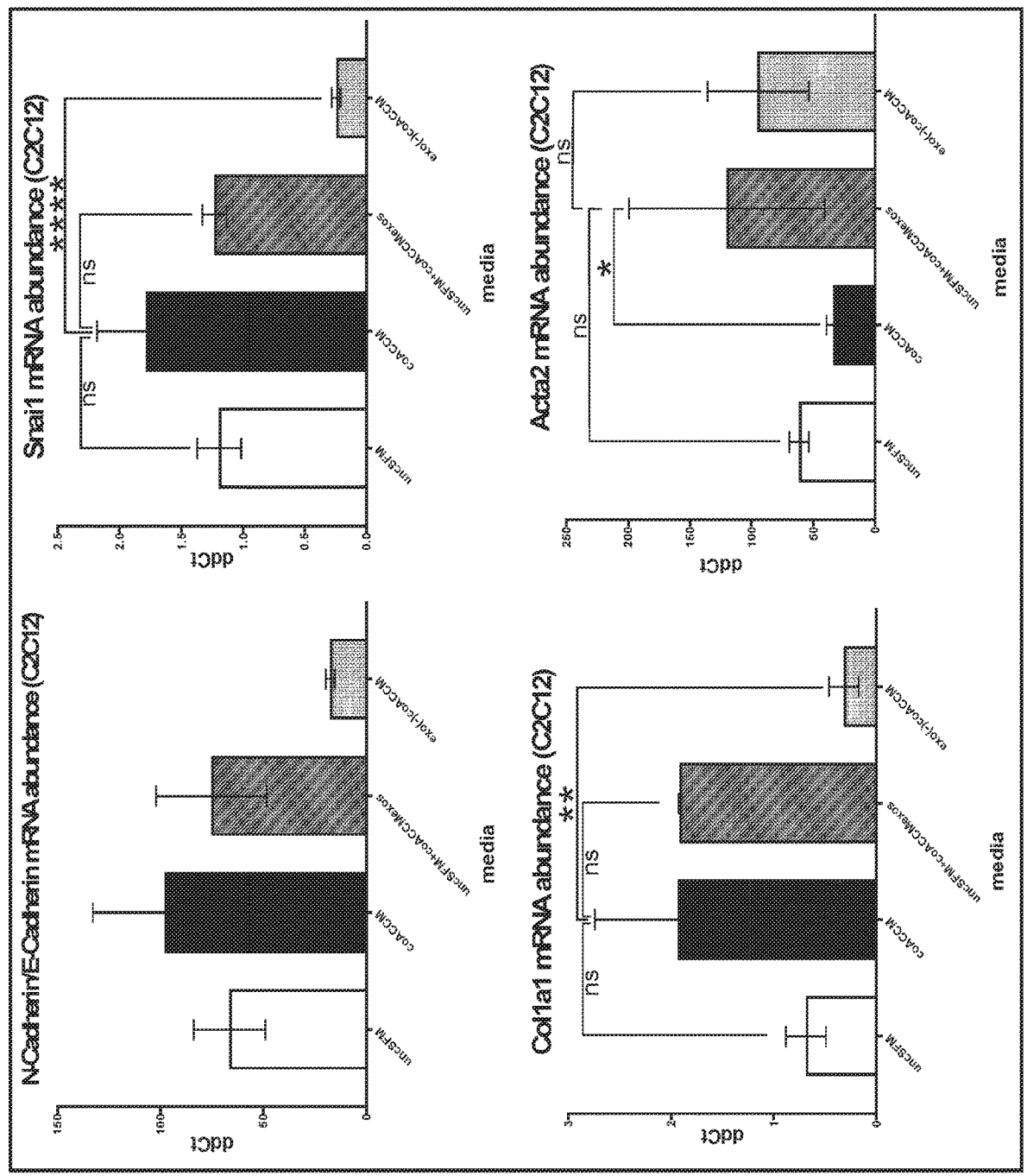

FIG. 19 shows the results of RT-qPCR analysis from RNA extracted from C2C12 myoblasts from scratch test analysis incubated for 24 h with uncSFM, coACCM, uncSFM plus an equal number of coACCM exosomes as that measure from total coACCM (uncSFM+coACCMexos), or exosome-depleted coACCM (exo(−)coACCM). N-Caherin/E-Cadherin ddCt ratio, Snail (Snail), Type I Collagen (Col1a1), and Smooth muscle actin (Acta2) abundance was measured as ddCt relative to Hydroxymethylbilane synthast (Hmbs; loading control). The N-Cad/E-Cad ratio is to measure EMT, but the ratio measurement precludes validity for measuring statistical significance, so none was reported/measured. Snail is a transcription factor that induces EMT. Col1a1 and Acta2 are "healing related" biomarkers. These results demonstrate that exosome-depleted coACCM appears to repress EMT and modulate healing-related gene expression relative to coACCM.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates. Following long-standing patent law convention, the terms "a," "an," and "the" refer to "one or more" when used in this application, including the claims. Thus, for example, reference to "a defined medium" includes a plurality of defined media, unless the context clearly is to the contrary, and so forth.

Throughout this specification and the claims, the terms "comprise," "comprises," and "comprising" are used in a non-exclusive sense, except where the context requires otherwise. Likewise, the terms "having" and "including" and their grammatical variants are intended to be non-limiting, such that recitation of items in a list is not to the exclusion of other like items that can be substituted or added to the listed items.

The term "administering" when used in conjunction with a therapeutic means to give or apply a therapeutic directly into or onto a target organ, tissue or cell, or to administer a therapeutic to a subject, whereby the therapeutic positively impacts the organ, tissue, cell, or subject to which it is targeted. Thus, as used herein, the term "administering", when used in conjunction with EVs or compositions thereof, can include, but is not limited to, providing EVs into or onto the target organ, tissue or cell; or providing EVs systemically to a patient by, e.g., intravenous injection, whereby the therapeutic reaches the target organ, tissue or cell. "Administering" may be accomplished by parenteral, oral or topical administration, by inhalation, or by such methods in combination with other known techniques.

The term "amniotic fluid" is meant to refer to the fluid inside the membrane that forms a sac around the embryo and later the fetus, which is in permanent contact with the fetus and the eye during the gestational period. The fetus and the placenta produce the amniotic fluid. In some embodiments of the invention, the AF that is used is human AF. However, those of skill in the art will recognize that AF from other mammalian species may also be successfully utilized, examples of which include but are not limited to horse, rabbit, lamb, cow sheep, primates, etc.

The term "amniotic cells" as used herein is meant to refer to cells obtained from amniotic fluid. The cells may comprise various cell types, including stem cells, adherent cells, blood cells, epithelial cells, fibroblast cells, muscle cells, or nerve cells.

As used herein, the term "adherent cells" is meant to refer to cells that attach to a surface.

Throughout this specification and the claims, the phrase "amniotic membrane (AM) cells" is used interchangeably with the phrase "amniotic epithelial cells (AEC)" and is intended to include all cell types derived from amniotic membrane of which the vast majority consists of amniotic epithelial cells.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Throughout this specification and the claims, the term "base media" is intended to mean a media that does not contain added serum (i.e., is essentially free of serum). Examples of base media include, but are not limited to, DMEM/F12, DMEM, F12, and IMDM.

The term "carrier" as used herein describes a material that does not cause significant irritation to an organism and does not abrogate the biological activity and properties of the compound of the composition of the described invention. Carriers must be of sufficiently high purity and of sufficiently low toxicity to render them suitable for administration to the mammal being treated. The carrier can be inert, or it can possess pharmaceutical benefits. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "cell culture" and "culture" as are used interchangeably throughout to refer to a process of growing cells under a controlled condition outside of their natural environment.

The term "cell line" as used herein means a permanently established cell culture developed from a single cell and therefore consisting of cells with a uniform genetic and functional makeup that will proliferate indefinitely.

The term "conditioned medium" (or plural, media), as used herein refers to spent culture medium harvested from cultured cells containing metabolites, growth factors, RNA and proteins released into the medium by the cultured cells.

The term "contact" and its various grammatical forms as used herein refers to a state or condition of touching or of immediate or local proximity.

The term "culture medium" (or plural, media), as used herein refers to a substance containing nutrients in which cells or tissues are cultivated for controlled growth.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor (TNF)-related molecules, including TNFα and lymphotoxin; immunoglobulin super-family members, including interleukin 1 (IL-1); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

As used herein, the term "derived from" is meant to encompass any method for receiving, obtaining, or modifying something from a source of origin.

As used herein, the term "enrich" is meant to refer to increasing the proportion of a desired substance, for example, to increase the relative frequency of a subtype of cell or cell component compared to its natural frequency in a cell population. Positive selection, negative selection, or both may be necessary to any enrichment scheme. Selection methods may include, without limitation, magnetic separation and fluorescence-activated cell sorting (FACS).

The term "expand" and its various grammatical forms as used herein refers to a process by which dispersed living cells propagate in vitro in a culture medium that results in an increase in the number or amount of viable cells.

The term "extracellular vesicles" or "EVs" as used herein includes exosomes and microvesicles that carry bioactive molecules, such as proteins, RNAs and microRNAs (cargo), that may be released into and influence the extracellular environment. Microvesicles are small membrane-enclosed sacs thought to be generated by the outward budding and fission of membrane vesicles from the cell surface. Exosomes originate predominantly from preformed multivesicular bodies that are released upon fusion with the plasma membrane.

The term "growth factor" as used herein refers to extracellular polypeptide molecules that bind to a cell-surface receptor triggering an intracellular signaling pathway, leading to proliferation, differentiation, or other cellular response. These pathways stimulate the accumulation of proteins and other macromolecules, e.g., by increasing their rate of synthesis, decreasing their rate of degradation, or both.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses. The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents. The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The term "ischemia" and its other grammatical forms" as used herein refers to an inadequate circulation of blood and oxygen, e.g., due to mechanical obstruction of the blood supply.

The term "perfusion" as used herein refers to a process of nutritive delivery by passage of a fluid through blood vessels or other natural channels in an organ or tissue.

The term "pharmaceutical composition" is used herein to refer to a composition that is employed to prevent, reduce in intensity, cure or otherwise treat a target condition or disease. The terms "formulation" and "composition" are used interchangeably herein to refer to a product of the described invention that comprises all active and inert ingredients.

The term "purification" and its various grammatical forms as used herein refers to the process of isolating or freeing from foreign, extraneous, or objectionable elements.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. In some embodiments "repair" includes full repair and partial repair.

The term "signaling pathways" as used herein refers to a sequential process initiated by binding of an extracellular signal to a receptor and culminating in one or more specific cellular responses. Exemplary signaling pathways include, without limitation:

Signaling Pathways

MAPK Signaling Pathway

MAPK signaling activates a three-tiered cascade with MAPK kinase kinases (MAP3K) activating MAP2K kinases (MAP2K) and finally MAPK. The major MAPK pathways involved in inflammatory diseases are extracellular regulating kinase (ERK), p38 MAPK, and c-Jun NH2-terminal kinase (JNK). Upstream kinases include TGFβ-activated kinase-1 (TAK1) and apoptosis signal-regulating kinase-1 (ASK1). Downstream of p38 MAPK is MAPK activated protein kinase 2 (MAPKAPK2 or MK2). (Barnes, P J, (2016) "Kinases as novel therapeutic targets in asthma and chronic obstructive pulmonary disease," Pharmacol. Rev. 68: 788-815).

NF-κB Signaling Pathways

NF-κB forms a family of transcription factors that participates in various biological processes, including immune response, inflammation, cell growth and survival, and development. (Shao-Cong Sun, "Non-canonical NF-kB signaling pathway, Cell Res. (2011) 21: 71-85). The mammalian NF-κB family is composed of five members, including RelA (also named p65), RelB, c-Rel, NF-κB1 p50, and NF-κB2 p52, which form various dimeric complexes that transactivate numerous target genes via binding to the κB enhancer. The NF-κB proteins are normally sequestered in the cytoplasm by a family of inhibitors, including IκBα and other related ankyrin repeat-containing proteins. NF-κB1 and NF-κB2 are translated as precursor proteins, p105 and p100, which contain an IκB-like C-terminal portion and function as NF-κB inhibitors. Proteasome-mediated processing of p105 and p100 not only produces the mature NF-κB1 and NF-κB2 proteins (p50 and p52) but also results in disruption of the IκB-like function of these precursor proteins.

The canonical NF-κB pathway of NF-κB activation relies on inducible degradation of IκBs, particularly IκBa, leading to nuclear translocation of various NF-κB complexes, predominantly the p50/RelA dimer 1, 2. The degradation of IκBα is mediated through its phosphorylation by the IκB kinase (IKK), a trimeric complex composed of two catalytic subunits, IKKα and IKKβ, and a regulatory subunit, IKKγ (also named NF-κB essential modulator or NEMO). In addition to this well-defined canonical pathway, other mechanisms exist to mediate activation of more specific NF-κB members 3. In particular, a non-canonical NF-κB pathway activates the RelB/p52 NF-κB complex using a mechanism that relies on the inducible processing of p100 instead of degradation of IκBa. Genetic evidence suggests that this NF-κB pathway regulates important biological functions, such as lymphoid organogenesis, B-cell survival and maturation, dendritic cell activation, and bone metabolism.

T Cell Receptor Pathway

The T cell receptor (TCR) recognizes self or foreign antigens presented by major histocompatibility complex (MHC) molecules. Engagement of the TCR triggers the formation of multi-molecular signalosomes that lead to the generation of second messengers and subsequent activation of multiple distal signaling cascades, such as the Ca+2-calcineurin-NFAT, RasGRP1-Ras-Erk1/2, PKCθ-IKK—NFκB, and TSC1/2-mTOR pathways, which control many aspects of T cell biology. See Gorentla, B K and Zhong, X-P, "T Cell receptor signal transduction in T Lymphocytes, J. Clin. Cell Immunol. (2012) (Suppl 12).

Tumor Necrosis Factor (TNF) Signaling Pathway 19 ligands and 29 receptors that belong to the tumour-necrosis factor (TNF) superfamily have been identified. See Aggarwal, Nature Revs. Immuno. (2003) 3:745-56. At the cellular level TNF-superfamily members promote either apoptosis (such as TNF, LT, CD95L, TRAIL, VEG1, TWEAK and LIGHT), proliferation (such as TNF, CD27L, CD30L, CD40L, OX4L, 4-1BBL, APRII, and BAFF), survival (such as RANKL and BAFF), or differentiation (such as TNF, RANKL and DR6).

The main signals transduced by the TNF-superfamily members include activation of nuclear factor-κB (NF-κB), JUN N-terminal kinase (JNK), p42/p44 mitogen-activated protein kinase (MAPK), and p38 mitogen activated protein kinase (MAPK). None of the receptors of the mammalian TANF superfamily has any enzymatic activity. Almost all of the members of the TNFR superfamily signal by binding to one or more TNFR-associated factors (TRAFs). Of the known TRAFs, only TRAF2, TRAF5 and TRAF6 have ewen shown to mediate the activation of NF-κB and JNK. TRAF2 is known to bind to almost all of the members of the TNFR superfamily; it binds to TNFR1 through the TNFR-associated death domain. Most members of the TNF superfamily activate NF-κB through ubiquitin-mediated degradation of its inhibitor IκBa. After TNF binding, TNFR1 translocates to cholesterol- and sphingolipid-enriched membrane microdomains, known as lipid rafts, in which it associates with the adaptor proteins TRADD and TRAF2, and the Ser/Thr kinase receptor-interacting protein (RIP) forming a signaling pathway. In lipid rafts, TNFR1 and RIP are ubiquitylated, which leads to their degradation by the proteasome pathway. Interfering with lipid raft organization not only abolishes ubiquitylation, but also switches TNF signaling from NF-κB activation to apoptosis.

Members of the TNF superfamily mediate haematopoiesis, immune surveillance, tumour regression and protection from infection. They also mediate inflammation, autoimmune diseases, rheumatoid arthritis, tumour metastasis, septic shock and osteoporosis.

Wnt Pathways

The Wnt signaling pathways are a group of signal transduction pathways of proteins that pass signals from outside of a cell through cell surface receptors to the inside of the cell. The variety of receptors and ligands involved in Wnt signaling lead to a multitude of diverse signal transduction cascades. See Gordon, M D and Nusse, R. J. Biol. Chem. (2006) 281 (32) 22429-22433.

The Wnt family of proteins consists of 19 known human members (Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16). These secreted lipid-modified signaling glycoproteins are 350-400 amino acids in length, share 20-85% amino acid identity, and have a conserved pattern of 23-24 cysteine residues. The type of lipid modification that occurs on these proteins is palmitoylation of cysteine in the conserved pattern of 23-24 cysteine residues. Palmitoylation initiates targeting of Wnt protein to the plasma membrane for secretion and allows the Wnt protein to bind its receptor due to the covalent attachment of fatty acids. Following their synthesis, secreted Wnt proteins are modified by glycosylation. In Wnt signaling, these secreted proteins act as ligands to activate the different Wnt pathways via paracrine and autocrine routes.

The Wnt signaling pathways are activated by the binding of a Wnt-protein ligand to a Frizzled ("Fz") family receptor, which passes the biological signal to the protein Disheveled inside the cell. To date, at least ten members of Frizzled family receptors have been identified, all of which are seven-pass transmembrane proteins characterized by an extracellular N-terminal conserved cysteine-rich domain (CRD) that interacts with Wnts. However, to facilitate Wnt signaling, co-receptors may also be required alongside the interaction between the Wnt protein and Fz receptor. Examples include low density lipoprotein receptor-related protein (Lrp5/6), receptor tyrosine kinase (Ryk), and Ror2.

Figure 5:
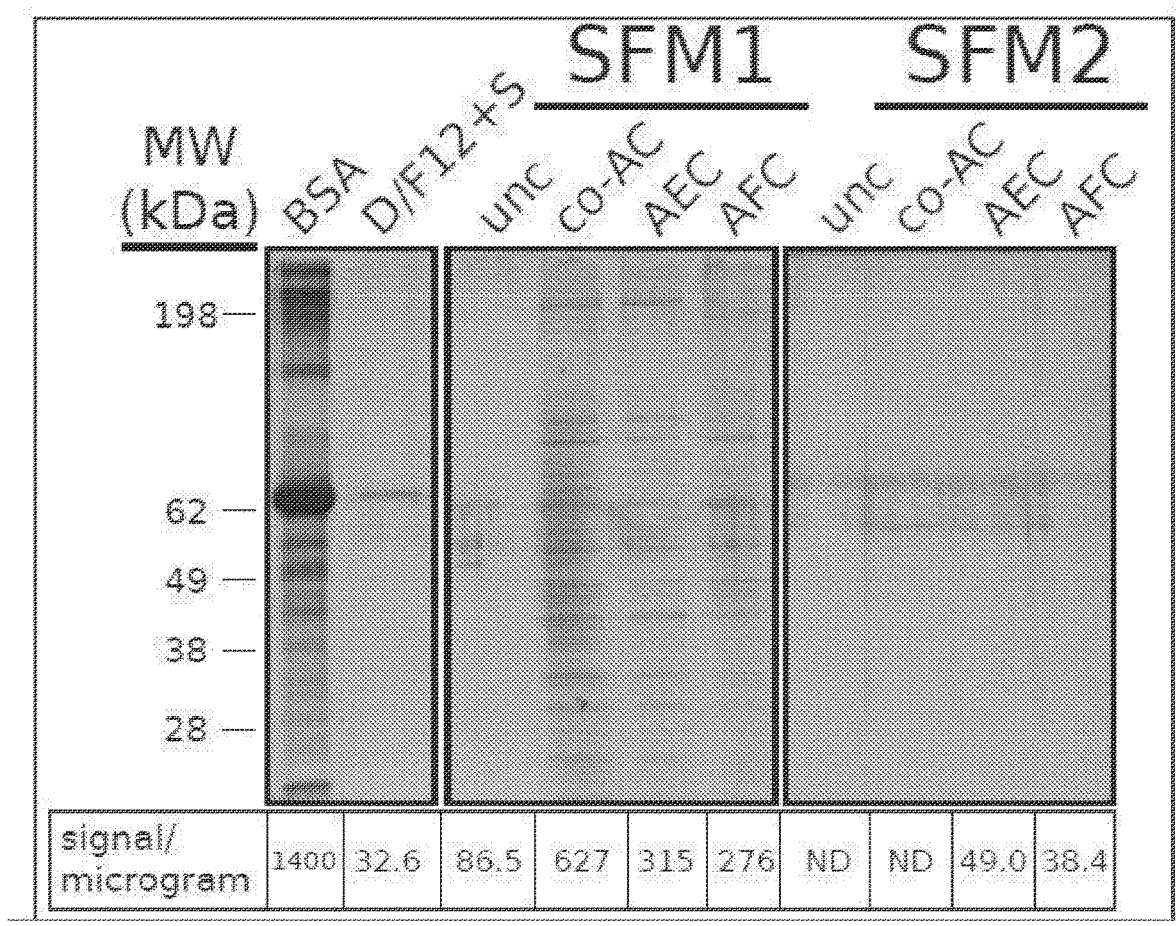
FIG. 5 is a an image of an SDS PAGE gel showing that co-culture of AECs and AFCs (co-AC) in a defined media, SFM1, according to the method illustrated in FIG. 4 results in increased total protein secretion and increased protein complexity according to one or more embodiments of the present disclosure. In contrast, co-culture in a different defined media, SFM2, resulted in no apparent increase in protein secretion as compared to unconditioned media. One microgram total protein was loaded in lanes (from left to right) consisting of bovine serum albumin (BSA), DMEM/F12+10% fetal bovine serum (D/F12+S), unconditioned serum-free media 1 (SFM1; unc), co-AC conditioned SFM1 (SFM1; co-AC), AEC conditioned SFM1 (SFM1; AEC), AFC conditioned SFM1 (SFM1; AFC), unconditioned serum-free media 2 (SFM2; unc), co-AC conditioned SFM2 (SFM2; co-AC), AEC conditioned SFM2 (SFM2; AEC), and AFC conditioned SFM2 (SFM2; AFC), and electrophoresed on 10% SDS-polyacrylamide gel then silver stained. The signal intensity calculated per lane is shown as "signal/microgram" at the bottom of the gel. The gels were scanned on a Li-Cor Odyssey CLx and signal per microgram protein determined by generating a region of interest consisting of each lane and determining signal counts using ImageStudio software program. Molecular weight in kilodaltons (kDa) is shown on the left; ND denotes no signal detected above background; all conditioned medias analyzed were generated by 24 h culture and unconditioned medias by 24 h incubation in a well of the same culture plate but minus cells.

Interaction of Wnts with their receptors and co-receptors is associated with at least three signaling pathways, namely the canonical Wnt/β-catenin pathway, the non-canonical (or heretical) planar cell polarity (PCP) pathway, and the non-canonical (or heretical) Wnt/Ca2+ pathway. FIG. 5 shows these three representative Wnt signaling pathways. The Fz receptors have the ability to discriminate between different Wnt ligands, and as such, activation of one of these three pathways is dictated by the nature of the ligand/receptor interaction. (Camilli, T. C., Biochem. 2010, Pharmacol. 80(5): 702-711). The canonical Wnt pathway leads to regulation of gene transcription, the noncanonical planar cell polarity pathway regulates the cytoskeleton that is responsible for the shape of the cell, and the noncanonical Wnt/calcium pathway regulates calcium inside the cell. Wnt signaling pathways use either nearby cell-cell communication (paracrine) or same-cell communication (autocrine).

Canonical Wnt Signaling Pathway

The canonical Wnt signaling pathway is a well-established, β-catenin-dependent signaling pathway which involves a key mediator, β-catenin. In the absence of Wnt signaling, β-catenin is phosphorylated by casein kinase 1 (CK1) and glycogen synthase kinase 3 beta (GSK3β) within a "destruction complex" formed by several proteins, including the scaffolding protein Axin and the tumor suppressor gene product APC (Adenomatous *Polyposis coli*). Phosphorylated β-catenin is then recognized by the ubiquitination machinery and sent for degradation in the proteasome. When Wnts bind to their receptors Fz and Lrp5/6, Lrp5/6 are phosphorylated and Disheveled is activated, which leads to inactivation or disassembly of the β-catenin "destruction complex" such that β-catenin phosphorylation is reduced and β-catenin is stabilized. The stabilized β-catenin then translocates to the nucleus where it regulates downstream gene expression by biding to Lef (Lymphoid enhanced transcription factor) and Tcf (T-cell factor), leading to the transcription of Wnt target genes involved in proliferation and tumor progression. Several members of the pathway can be regulated independently of Wnt signaling. For example, GSK-3β can be inhibited by ILK (Integrin Linked Kinase), and is at the intersection of numerous pathways that might regulate its expression. The Canonical Wnt proteins include Wnt1, Wnt2, Wnt3a, Wnt8a, Wnt8b, Wnt10a, Wnt10b (Jiar C H, J Oral Pathol. Med., 2012, 41(4):332-339).

The Wnt/PCP pathway has been best described in development, where it coordinates the polarization of cells along embryonic axes. This involves the activation of STAT3, and JAK/STAT signaling (Miyagi C, et al., J Cell Biol 2004, 166(7):975-981). Wnts that play a role in Wnt/PCP signaling include Wnt5A, Wnt11, and Wnt 7a (Wang Y., Mol Cancer Ther, 2009; 8(8):2103-2109). During Wnt/PCP signaling, Wnt/Fz/Ror2 interactions recruit disheveled (Dsh/Dvl) to the membrane, trigger the recruitment of yang and prickle to the membrane of adjacent cells, and the balance between these regulates polarity. Disheveled-dependent Wnt/PCP signaling then transduces signals via JNK, Jun, Daam, RhoA, Rac, Cdc42 and Profilin, and these have cytoskeletal effects that ultimately control both polarity and motility (Carreira-Barbosa F, et al., Development 2003, 130(17): 4037-4046; Takeuchi M, et al., Curr Biol 2003, 13(8):674-679; Qian D, et al., Dev Biol 2007, 306(1):121-133). Since these features (meaning polarity and motility) are critical for tumor progression, Wnt/PCP signaling has been implicated in cancer. (Camilli, T. C., Biochem. 2010, Pharmacol. 80(5): 702-711).

The Wnt/Ca2+ pathway involves the release of intracellular calcium downstream of Wnt signaling. Members of the Wnt family involved in the Wnt/Ca2+ signaling pathway include Wnt5a, Wnt11, and Wnt4, and activation of the Fz receptors by these Wnts was shown to result in the activation of calcium-dependent signaling molecules, such as calmodulin-dependent protein kinase II (CAMKII) and protein kinase C (PKC). These molecules can have a cornucopia of effects on downstream signaling that is often dependent on the cellular context. (Camilli, T. C., Biochem. 2010, Pharmacol. 80(5): 702-711).

More noncanonical Wnt cascades (pathways) have been suggested including Wnt-RAP1 signaling; Wnt-receptor tyrosine kinase-like orphan receptor 2 (Ror2) signaling; Wnt-protein kinase A signaling; Wnt-GSK-3-mirotubule signaling; Wnt-atypical protein kinase C (PKC) signaling; Wnt-receptor-like tyrosine kinase signaling; and Wnt-mammalian target of rampamycin signaling. These classifications are not rigid since the pathways overlap and intersect with one another and are evolving. (Semenov, M. V.; Cell 2007, 131: 1378).

The terms "treat," "treated," or "treating" as used herein refers to both therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

According to one aspect, the present disclosure provides compositions that contain active biological components of amniotic fluid including growth factors and other proteins, carbohydrates, lipids and metabolites. According to some embodiments, the compositions are useful for treating a range of conditions, including respiratory diseases or disorders, infections, liver diseases or disorders, kidney diseases or disorders, cancers, and metabolic disorders. According to some embodiments, the compositions are useful for treating Chronic Obstructive Pulmonary Disease (COPD). According to some embodiments, the compositions are useful for treating HIV/AIDS. According to some embodiments, the compositions are useful for treating diabetes. According to some embodiments, the compositions are useful for a range of therapeutic treatments including, for example, tissue repair such as wound healing, promotion of cell/tissue homeostasis (meaning a tendency to maintain internal stability due to the coordinated response of its parts to any situation or stimulus tending to disturb its normal condition or function), and treatment of a skin condition. In addition, the compositions of the present disclosure are useful for organ preservation, such as in organ transplant procedures. In contrast to prior art amniotic fluid compositions, the compositions of the present disclosure can be reproducibly produced, without the inherent variability of amniotic fluid from separate donors. Another advantage of the compositions of the present disclosure is that they are free of fetal waste products including, but not limited to, the high concentration of urea observed in amniotic fluid.

The compositions provided contain biologically active components of amniotic fluid. For the purpose of this specification and claims, the phrase "biologically active components of amniotic fluid" is used interchangeably with "biologically active components" and "components" and is intended to include all types of molecules secreted (meaning elaborated or produced by a cell and delivered outside the cell) from cells of amniotic tissue including, but not limited to, proteins, enzymes, hormones, growth factors, cytokines, lipids, carbohydrates, electrolytes, and extracellular vesicles containing cargo such as the foregoing listed molecules. The terms "extracellular vesicles", "microvesicles", "exosomes", "secreted microvesicles", and "secreted vesicles" are used interchangeably herein for the purposes of the specification and claims.

Collecting Amniotic Fluid

According to some embodiments, amniotic fluid may be collected from a human or other mammal. Amniotic fluid may be recovered from a human during an amniocentesis or during a C-section. Potential donor mothers may be screened for risk factors to determine whether the amniotic fluid is safe and suitable for donation or processing. In one embodiment, a donor mother is tested for one or more viruses or bacteria using serological tests, which can include without limitation antibody, nucleic acid, or culture testing.

According to some embodiments, amniotic fluid may be recovered during an elective C-section procedure performed in a sterile operating room environment. Collection may be achieved by drawing amniotic fluid from the mother into a collection container using a needle or tubing via low-level suction or gravity. See US 2014/0336600. At the time of collection, cultures of the collected amniotic fluid may be taken to determine the presence of bacteria, such as *Clostridium* or *Streptococcus*.

According to some embodiments, collected amniotic fluid may be packaged in a sterile container, labeled, and shipped on wet ice to a processing laboratory for further processing and evaluation. If the donor mother's health information, screening tests, and cultures are satisfactory (i.e., indicate no risk or acceptable level of risk to human handling or use), the amniotic fluid may be processed for human medical applications.

Figure 1:
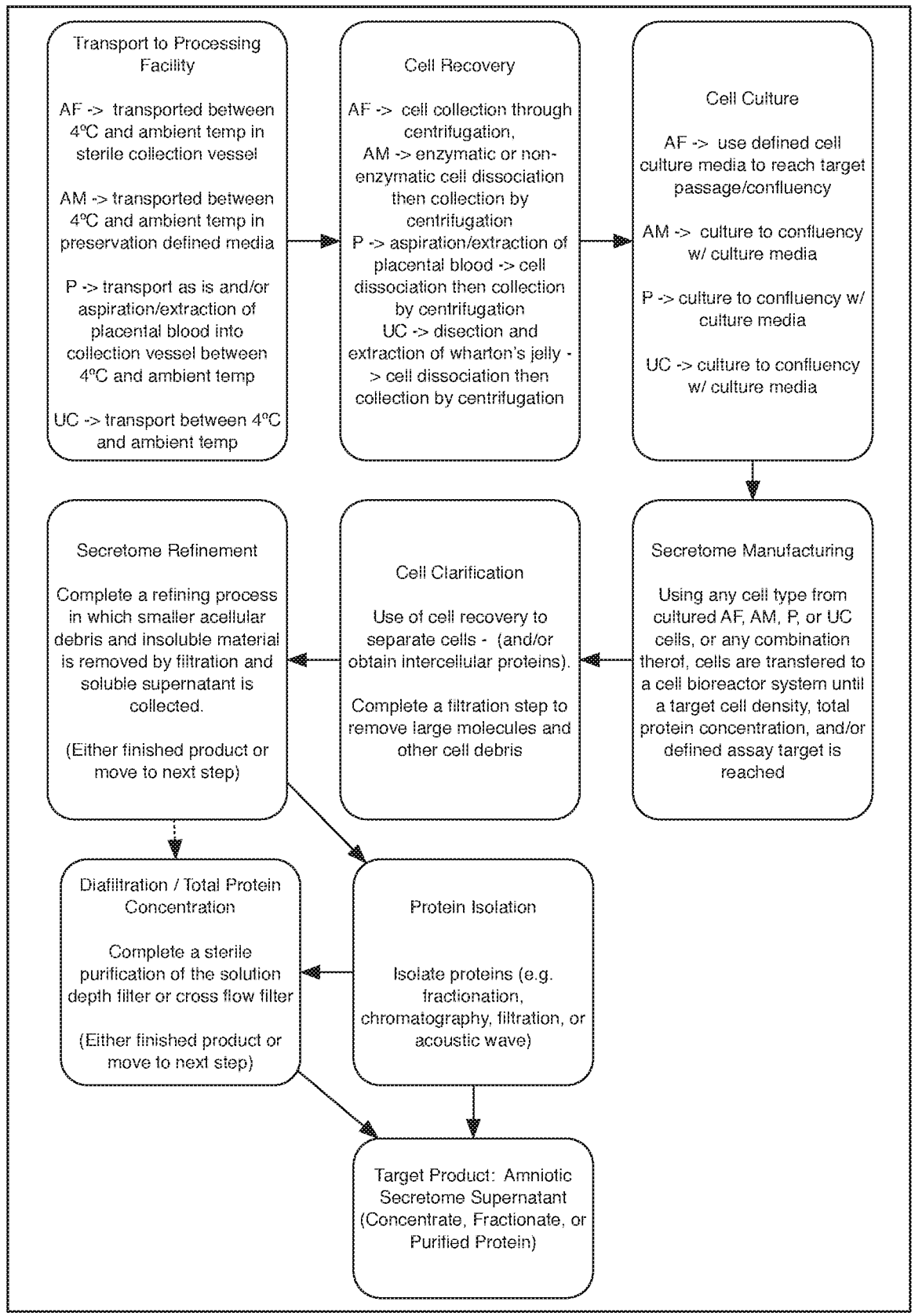
FIG. 1 is a flow diagram showing methods for making compositions comprising components of amniotic fluid according to one or more embodiments of the present disclosure.

According to some embodiments, the compositions are produced from cells derived from a donor of amniotic tissue according to a method illustrated in the flow chart of FIG. 1. Amniotic tissues including one or a combination of amniotic fluid (AF), amniotic membrane (AM), placenta (P), and umbilical cord (UC) can be obtained from a donor and processed according to standard procedures as outlined in FIG. 1. The donor can be a mammal and the cells can be processed without having been previously frozen. The mammal can be a human. The donor can be a C-section donor. Cells can be recovered from the one or a combination of tissues using standard procedures such as those outlined in FIG. 1.

One or more types of cells including, but not limited to, AF cells, AEC cells, P cells, and UC cells can be recovered from the amniotic tissue using standard procedures as outlined in FIG. 1. These cells may then be cultured (meaning to grow in or on a controlled or defined medium in vitro) to expand the cells. Whether or not the cells are expanded first, the cells may be frozen for storage and later use. According to some embodiments, the cells are transformed and converted to a cell line for use in the methods of the present disclosure.

The one or more types of recovered cells (AF cells, AEC cells, P cells, and UC cells) can be expanded or cultured to a target passage as outlined in FIG. 1. The culturing can be in acellular cytokine-rich amniotic fluid (AFCK), in media enhanced with AFCK, or in another defined cell culture media using standard cell culture procedures. According to some embodiments, the one or more types of recovered cells are cultured separately.

The one or more types of recovered cells (AF cells, AEC cells, P cells, and UC cells) are transferred to a cell culture system and cultured in a defined medium essentially free of serum until a point where a predetermined total protein concentration is present in the conditioned cell medium. The defined medium essentially free of serum can consist of a base media, one or more of monothioglycerol, lipids, or polyvinyl alcohol, and optionally one or more antibiotics. According to some embodiments, the AECs can be mitotically inactivated using radiation. According to other embodiments, the AECs can be mitotically inactivated using mitomycin C. According to still other embodiments, the AECs can be mitotically inactivated using any agent that inhibits cell proliferation including but not limited to inhibitors of cellular components necessary for mitosis such as but not limited to protein synthesis, microtubule function, spindle check point unit, cell cycle specific kinases, cyclins, and or apoptotic inducing agents, prior to transferring to the cell culture system.

In the methods of the present disclosure, the cell culture system can comprise tissue culture flasks/plates, a bioreactor, a suspension bioreactor, or an adherent bioreactor. Growth factors and other active biological components of the amniotic tissue-derived cells are secreted by the cultured living cells. At a predetermined point, the liquid medium portion of the culture system contains conditioned cell supernatant that is rich in secreted factors. The growth factors and other extracellular components including proteins and extracellular vesicles containing cargo are secreted into the nutrient medium in which they are cultured. In the methods for making the compositions of the present disclosure, the at least one cell type can be separated from the defined medium essentially free of serum once the cells reach the predetermined target total protein concentration to obtain a conditioned supernatant.

According to some embodiments, large molecules (including debris or clumps) may be removed from the conditioned supernatant by via mechanical pressure, gravity, or suction, or by low-speed centrifugation. According to some embodiments, the conditioned supernatant can be filtered to remove large molecules and other cell debris. According to some embodiments, the amniotic fluid may be filtered by gravity through a polymer filter (e.g., polypropylene, nylon, or polyester, etc.) or metal filter. The sterility of the conditioned supernatant is ensured, and in some cases one or more procedures are performed to sterilize the conditioned supernatant. According to some embodiments, the sterilization procedure can be one or more filtration procedures. In this manner, the sterile conditioned supernatant yields a composition comprising biologically active components of amniotic fluid. An advantage of the compositions of the present disclosure, in contrast to amniotic fluid derived from a single donor, is that the compositions can be reproducibly produced to avoid large deviations in the amounts of biologically active components and can be produced free of fetal waste products including but not limited to the high concentration of urea observed in amniotic fluid.

According to some embodiments, the conditioned supernatant is substantially free of one or more of blood cells, red blood cells, white blood cells, urea, electrolytes, or amino acids.

According to some embodiments, the urea or electrolyte content of the conditioned supernatant is not detectable.

According to some embodiments, the conditioned supernatant has a urea content of less than a value, of greater than a value, of at least a value, of a value, or ranging from any two values, wherein the value is selected from about 300 µg, about 250 µg, about 200 µg, about 150 µg, about 100 µg, about 90 µg, about 80 µg, about 70 µg, about 60 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, and about 0.01 µg.

Thus, according to some embodiments, a method is provided for making a composition comprising components of amniotic fluid, the method including: (a) transferring at least one of cell types selected from the group consisting of: (i) amniotic fluid cells, (ii) amniotic membrane cells, (iii) placental cells, and (iv) umbilical cord cells to a cell culture system and culturing the at least one cell type in a defined medium essentially free of serum; (b) separating the at least one cell type from the culture medium to obtain a conditioned supernatant; (c) removing large molecules and other cell debris from the conditioned supernatant; and (d) ensuring the stability of the conditioned supernatant, wherein the sterile conditioned supernatant is the composition having components of amniotic fluid. The defined medium essentially free of serum can contain a base media, one or more of monothioglycerol, lipids, or polyvinyl alcohol, and optionally one or more antibiotics.

According to some embodiments, the composition is sterilized.

According to some embodiments of the compositions and methods of the present disclosure, the cell types used in the process for producing the composition comprising the components of amniotic fluid can contain at least two of the cell types (i)-(iv). According to some embodiments, the cell types can contain at least three of the cell types (i)-(iv). According to some embodiments, the cell types can contain the four cell types (i)-(iv).

According to some embodiments, the compositions described herein may serve as a superior basal or stand-alone media to aid in many different processes during in vitro cell culture, including, but not limited to stem cell differentiation, primary cell expansion, activating EMT for basic science and/or therapeutic purposes, propagating cells procured from a donor that will be re-introduced into a patient (autologous or otherwise).

FIGS. 2A-2D are images of AECs and AFCs recovered and cultured as illustrated in FIG. 1 and stained with the stem cell marker stage-specific antigen 4 (SSEA4) and DAPI (stains all DNA/nuclei). Specifically, FIG. 2A shows AECs stained with antibody recognizing stage-specific embryonic antigen 4 (SSEA4), FIG. 2B shows AECs stained with 4',6-diamidino-2-phenylindole (DAPI), a blue-fluorescent DNA stain that binds to AT regions of ds DNA, commonly used as a nuclear counterstain, FIG. 2C shows AFCs stained with antibody recognizing SSEA4, and FIG. 2D shows AFCs stained with DAPI. The results show that the majority of propagated cells are amniotic stem cells rather than amniotic fibroblast, myoblast, or other non-stem cell types.

Figure 3A:
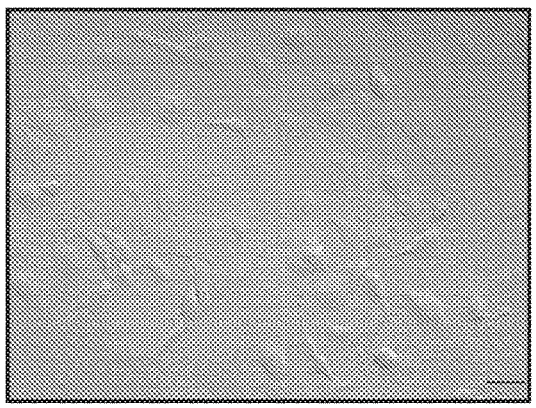
FIG. 3A is an image of AECs plated in DMEM basal media at 0 h according to one or more embodiments of the present disclosure (scale bar denotes 50 µm).
Figure 3B:
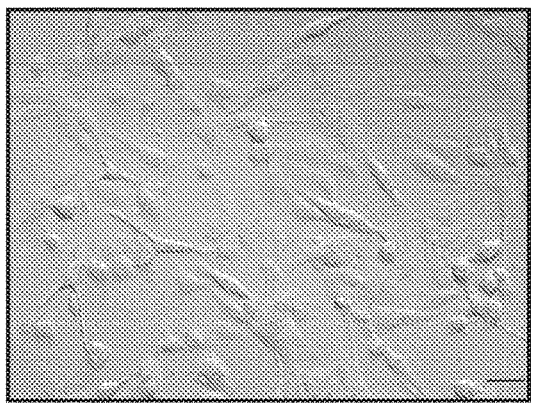
FIG. 3B is an image of AECs plated in DMEM basal media at 24 h according to one or more embodiments of the present disclosure (scale bar denotes 50 µm).
Figure 3C:
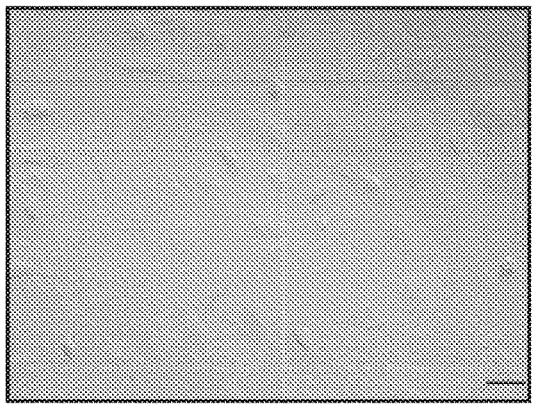
FIG. 3C is an image of AECs plated in SFM2 media at 0 h according to one or more embodiments of the present disclosure (scale bar denotes 50 µm).
Figure 3D:
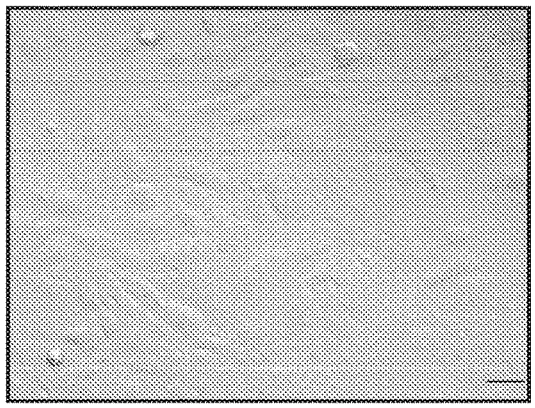
FIG. 3D is an image of AECs plated in SFM2 media at 24 h according to one or more embodiments of the present disclosure (scale bar denotes 50 µm).
Figure 3E:
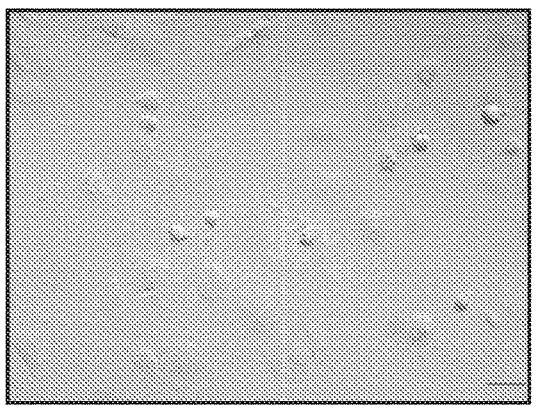
FIG. 3E is an image of AECs plated in SFM1 media at 0 h according to one or more embodiments of the present disclosure (scale bar denotes 50 µm).
Figure 3F:
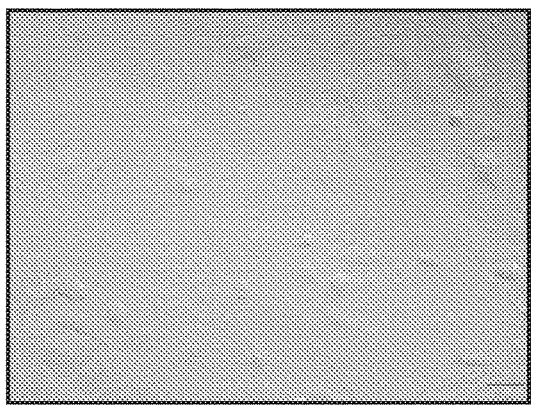
FIG. 3F is an image of AECs plated in SFM1 media at 24 h according to one or more embodiments of the present disclosure (scale bar denotes 50 µm).

FIGS. 3A-3F are images of AECs comparing incubation in 3 different types of serum free media for 24 hours. Specifically, FIGS. 3A and 3B show the results with DMEM, FIGS. 3C and 3D show the results with SFM2, and FIGS. 3E and 3F show the results with SFM1. The cells in FIG. 3B appear relatively more spindly, having taken on more of a fibroblast-like morphology, in the DMEM media, whereas the cells incubated for 24 h in both SFM1 and SFM2 maintained their epithelial morphology. The SFM2 consists of DMEM/F12 and 1% penicillin/streptomycin. The SFM1 consists of 50% IMDM, 50% F12, 1 mg/ml polyvinyl alcohol, 1% chemically-defined lipid concentrate, 450 µM monothioglycerol, and 1% penicillin/streptomycin.

According to some embodiments, a method for making a composition having components of amniotic fluid is provided and is illustrated in FIG. 4. The method comprises transferring AECs and AFCs to a cell culture system and culturing the AECs and AFCs in a defined medium essentially free of serum, separating the AECs and AFCs from the culture medium to obtain a conditioned supernatant, removing large molecules and other cell debris from the conditioned supernatant, and ensuring the sterility of the conditioned supernatant, wherein the conditioned supernatant is the composition having components of amniotic fluid. As is illustrated in steps 402, 404, 406, and 408 of FIG. 4, each of the AECs and AFCs can be expanded in culture prior to transferring the cells to the cell culture system by passaging the cells one, two, three or more times. According to some embodiments, the AECs can be attached to a surface of the culture system and the AFCs can be deposited on top of the AECs, as is illustrated in steps 410 and 412 of FIG. 4. The AECs can be mitotically inactivated prior to transferring to the cell culture system as illustrated in step 410 of FIG. 4. Step 414 of FIG. 4 illustrates culturing the AECs and AFCs in a defined medium essentially free of serum. According to some embodiments, the AECs and AFCs are cultured in a suspension culture rather than by attachment to a surface as shown in FIG. 4. The AECs and AFCs can be cultured until a predetermined target total protein concentration in the conditioned supernatant. The step of separating the AECs and AFCs from the culture medium to obtain a conditioned supernatant is illustrated by step 416 of FIG. 4. The terms "conditioned supernatant" and "amniotic cell conditioned media (ACCM)" or co-cultured ACCM (co-ACCM) are herein used interchangeably and refer to the composition having components of amniotic fluid.

FIG. 5 shows analysis by SDS-PAGE and silver staining of the amniotic cell conditioned media produced using two different types of serum free media (SFM1 and SFM2) at step 414 in the method. As can be seen in FIG. 5, the co-culture of the AECs and AFCs (co-AC) in the defined media, SFM1, resulted in increased total protein secretion and increased protein complexity (i.e., the same amount of total protein (1 µg) is added in each lane, but the co-AC conditioned media shows both different bands present and an increased signal intensity relative to AECs or AFCs alone). Surprisingly, the co-culture of the AECs and AFCs in the SFM2 media shows no apparent protein secretion at all compared to unconditioned media. These data illustrate a synergistic effect of the co-culture of the AECs and AFCs in the SFM1 media that can yield a conditioned media having both increased protein concentration and increased protein complexity.

FIG. 6 shows analysis by Bradford assay and LC-MS/MS of the amniotic cell conditioned medium (ACCM) from the co-culture of the AECs and AFCs in the SFM1. As can be seen in FIG. 6, the co-culture of the AECs and AFCs in the SFM1 media according to the method described above resulted in the highest total protein concentration by Bradford assay. Using the LC-MS/MS method a higher number of proteins (by identity) is observed in ACCM compared to AECs or AFCs alone. The viable cell results from the trypan blue exclusion assay show that the AFC alone cell count is the same as the co-AC cell count, indicating that the higher protein concentration and increased number of distinct protein identities results from the same number of cells per well. These data show the synergistic effect of the co-culture of the AECs and AFCs in the SFM1 media that can yield a conditioned media having both increased protein concentration and complexity.

FIG. 7 is a Venn diagram of the LC-MS/MS data shown in FIG. 6 showing that the co-culture of the AECs and AFCs in the SFM1 media yields 84 unique proteins by identity not observed in either the AEC- or AFC alone conditioned SFM1. This result illustrates the synergistic effect of the co-culture of the AECs and AFCs in the SFM1 media that can yield a conditioned media with increased protein complexity.

FIG. 8 shows, by quantitative analysis, the number and percentage of proteins identified by LC-MS/MS in the conditioned SFM1 from the co-culture of the AECs and AFCs. The data in FIG. 8 show that the co-culture of the AECs and AFCs yielded quantitatively higher levels of proteins than in either AECs only, AFCs only, or the sum of AECs and AFCs only. The results in FIG. 8 show that the quantity of 225 of the identified proteins (27.3% of the total) are present at a higher level in the conditioned media from co-culture of AECs and AFCs than the additive level of AEC alone-conditioned SFM1 plus AFC alone-conditioned SFM1. These data illustrate, using a quantitative analysis of the proteome, the synergistic effect of the co-culture of the AECs and AFCs in the SFM1 media that can yield a conditioned media with increased protein concentration and complexity, and rule-out a simply additive effect of AFC and AEC conditioning alone.

FIG. 9 shows the results of Gene ontology (GO) term analysis identifying significantly enriched biological pathways represented within the proteome of conditioned SFM1 from the co-culture of the AECs and AFCs according to the methods of the present disclosure. LC-MS/MS data from the conditioned SFM1 was compared to unconditioned SFM1 LC-MS/MS data to derive enriched ($p \leq 0.05$) GO terms. The GO result showing enrichment of various types of RNA metabolism (meaning any events in the life cycle of ribonucleic acid (RNA) molecules, including their synthesis, folding/unfolding, modification, processing and degradation). indicates that the amniotic cell conditioned media of the present disclosure can promote overall cell homeostasis by promoting proper RNA stability, localization, translation, and decay.

Without being limited by any particular theory, the identification of proteins enriched in NF-kappa B/NIK signaling pathway, T cell receptor signaling pathway, tumor necrosis factor-mediated signaling pathway, and MAPK cascade indicates that ACCM can function as an anti-inflammatory and protect against cell death in a variety of pathological conditions.

Without being limited by any particular theory, the identification of proteins significantly enriched in Wnt signaling pathway, planar cell polarity pathway, positive regulation of canonical Wnt signaling pathway, and positive regulation of telomere maintenance via telomerase indicates that ACCM can function to regulate stem cell self-renewal/differentiation to specific target cell types. Without being limited by any particular theory, the identification of proteins enriched in MAPK cascade, positive regulation of telomere maintenance via telomerase, regulation of cell growth, insulin-like growth factor I and II binding indicate that ACCM can function to promote cell growth/homeostasis and/or support metabolic activity. Without being limited by any particular theory, the identification of proteins enriched in cell-cell adherens junction and cadherin binding involved in cell-cell adhesion indicate ACCM can promote cell attachment to a substrate. Without being limited by any particular theory, the identification of proteins enriched in extracellular exosomes indicates ACCM can mediate vesicular transport of cargo (proteins, nucleic acid, lipids and other biomolecules) to cells/tissues. Additionally, these findings indicate that ACCM is enriched in the types of proteins present in amniotic fluid.

In the methods for making a composition having components of amniotic fluid of the present disclosure, the defined medium essentially free of serum can comprise a base media one or more of monothioglycerol, lipids, or polyvinyl alcohol and, optionally, one or more antibiotics. The lipids can comprise arachidonic acid, cholesterol, DL-alpha-tocopherol acetate, linoleic acid, linolenic acid, myristic acid, oleic acid, palmitic acid, palmitoleic acid, and stearic acid.

The methods of the present disclosure can further include concentrating (meaning to make denser, stronger or purer by the removal or reduction of liquid) the sterile conditioned supernatant.

According to some embodiments, the sterile conditioned supernatant is cryopreserved, partially dehydrated, dehydrated, lyophilized, refrigerated, or frozen.

According to some embodiments, the sterile conditioned supernatant is lyophilized and stored or administered as a powder.

According to some embodiments, the compositions are not diluted with any additional solution for storage. According to some embodiments, the compositions are diluted prior to administration or application. According to some embodiments, the compositions are not concentrated relative to the raw fluid.

According to some embodiments, the compositions can be stored for long periods of time, allowing for a broad range of application methods, including distribution and storage as aerosols, solutions, powders, etc. In some embodiments, the compositions are refrigerated at about 1° C. to about 10° C. for long-term storage. In a further embodiment, the compositions are refrigerated at 4° C. for up to 12 months and more. In some embodiments, the compositions are stored at −20° C. or at −80° C. for long-term storage. Preferably, the long-term storage does not reduce the quantity of the total soluble proteins or factors present in the compositions. For some embodiments, the total soluble proteins retained after long-term storage is about 10%, 20%, 30%, 40%, 50%, 60%, 70%, 80%, or 90% or more of the fresh composition.

The methods of the present disclosure can further include isolating (meaning to render substantially or essentially free (95%, 96%, 97%, 98%, 99% or more) from components that normally accompany or interact with as found in its naturally occurring environment) one or more of the proteins, microvesicles/exosomes, nucleic acids, or lipids present in the sterile conditioned supernatant. The isolation of one or more of the proteins, microvesicles/exosomes, nucleic acids, or lipids can be through fractionation, filtration, chromatography or combinations thereof.

The cell types of the present disclosure can be derived from mammalian tissue without having been previously frozen. The mammalian tissue can be a human tissue.

According to some embodiments, a method is provided for preservation of an organ, the method including surrounding the organ in a composition having components of amniotic fluid produced according to any of the methods described herein, wherein the organ is preserved in the composition. According to some embodiments, a method is provided for preservation of an organ, the method including perfusing the organ in a composition having components of amniotic fluid produced according to any of the methods described herein. A perfusion device can be used for the perfusing. According to some embodiments, the preserved organ can be used in a transplant procedure.

According to some embodiments, the process for producing a composition comprising components of amniotic fluid comprises (a) transferring at least one of cell types selected from the group consisting of: (i) amniotic fluid cells, (ii) amniotic membrane cells, (iii) placental cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; (d) ensuring the sterility of the conditioned supernatant; and (e) one or both of concentrating the sterile conditioned supernatant and isolating one or more proteins, microvesicles/exosomes, nucleic acids, or lipids present in the total protein, wherein the one or both of concentrated conditioned supernatant and isolated proteins, microvesicles/exosomes, nucleic acids, or lipids are the composition having components of amniotic fluid. The defined medium essentially free of serum can consist of a base media, one or more of monothioglycerol, lipids, or polyvinyl alcohol, and optionally one or more antibiotics.

According to some embodiments, the process for producing a composition comprising components of amniotic fluid comprises (a) transferring amniotic epithelial cells (AECs) and amniotic fluid cells (AFCs) to a cell culture system and culturing the AECs and AFCs in a defined medium essentially free of serum comprising a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition comprising components of amniotic fluid.

Also provided is a product (e.g. a composition comprising components of amniotic fluid as described herein) prepared according to a method of preparation disclosed herein.

Pharmaceutical Compositions

Also provided is a composition comprising components of amniotic fluid as described herein that may be combined with one or more pharmaceutically acceptable carriers or excipients, to produce an appropriate pharmaceutical composition suitable for administration to a subject. Such pharmaceutically acceptable compositions are an aspect of the invention. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds is well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types. which are incorporated herein by reference in their entirety). Furthermore, compounds and compositions of the invention may be used in combination with any compound or composition used in the art for treatment of a particular disease or condition of interest.

A pharmaceutical composition is typically formulated to be compatible with its intended route of administration. According to some embodiments, the pharmaceutical composition is in the form of a cream, lotion, emulsion, gel, liposome, nanoparticle, spray, or ointment. According to some embodiments, the pharmaceutical composition is formulated for administration by injection. According to some embodiments, when the pharmaceutical composition is used for topical administration, the pharmaceutically acceptable carrier comprises hyaluronic acid. According to some embodiments, when the pharmaceutical composition is used for topical administration, the pharmaceutically acceptable carrier comprises a bulking agent, protein carrier, a polysaccharide, or a polymer. According to some embodiments, the protein carrier comprises collagen, fibronectin, elastin, or laminin. According to some embodiments, the polysaccharide is a carboxymethylcellulose a carboxyethylcellulose, a hydroxypropylcellulose, a hydroxyethylcellulose, or chitosan. In some embodiments, the pharmaceutically acceptable carrier comprises polyoxyethylene oxide.

Pharmaceutical compositions, when administered to a subject, are preferably administered for a time and in an amount sufficient to treat the disease or condition for which they are administered. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the art. The dose used may be the maximum tolerated dose or a lower dose. A therapeutically effective dose of an active agent in a pharmaceutical composition may be within a range of about 0.001 to about 100 mg/kg body weight, about 0.01 to about 25 mg/kg body weight, about 0.1 to about 20 mg/kg body weight, about 1 to about 10 mg/kg. Other exemplary doses include, for example, about 1 pg/kg to about 500 mg/kg, about 100 pg/kg to about 5 mg/kg). In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, the particular disease or condition and its severity, the age, body weight, general health of the subject, etc.

According to some embodiments, a topical composition is provided for regulating a skin condition, the topical composition including: i) a safe and effective amount of a composition comprising components of amniotic fluid; and ii) one or more carriers. The one or more carriers can include one or more active or inactive agents. The term "active" as used herein refers to the ingredient, component or constituent of the compositions of the present invention responsible for the intended effect. The active or inactive agents can include, but are not limited to, moisturizing agents, vitamins, and anti-oxidants. The composition comprising components of amniotic fluid is produced by a process as described herein.

According to some embodiments, the pharmaceutical composition described herein enhances collagen production in vitro. According to some embodiments, the pharmaceutical composition described herein enhances collagen production in vivo. Accordingly, in certain embodiments, the pharmaceutical compositions described herein are used to enhance collagen production in cosmetic/beauty applications. According to some embodiments, the pharmaceutical compositions described herein are used to enhance collagen production at a wound site. The pharmaceutical compositions for use in enhancing collagen production may be administered, for example as injections for intracutaneous, subcutaneous and intravascular administrations; intraperitoneal perfusates and washes; dialysates for peritoneal dialysis; solutions for washing and disinfecting wounds; ophthalmics; nebulas; external preparations.

According to some embodiments, the topical composition can include from about 0.1 to about 20% (i.e., 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, 10%, 10.1%, 10.2%, 10.3%, 10.4%, 10.5%, 10.6%, 10.7%, 10.8%, 10.9%, 11%, 11.1%, 11.2%, 11.3%, 11.4%, 11.5%, 11.6%, 11.7%, 11.8%, 11.9%, 12%, 12.1%, 12.2%, 12.3%, 12.4%, 12.5%, 12.6%, 12.7%, 12.8%, 12.9%, 13%, 13.1%, 13.2%, 13.3%, 13.4%, 13.5%, 13.6%, 13.7%, 13.8%, 13.9%, 14%, 14.1%, 14.2%, 14.3%, 14.4%, 14.5%, 14.6%, 14.7%, 14.8%, 14.9%, 15%, 15.1%, 15.2%, 15.3%, 15.4%, 15.5%, 15.6%, 15.7%, 15.8%, 15.9%, 16%, 16.1%, 16.2%, 16.3%, 16.4%, 16.5%, 16.6%, 16.7%, 16.8%, 16.9%, 17%, 17.1%, 17.2%, 17.3%, 17.4%, 17.5%, 17.6%, 17.7%, 17.8%, 17.9%, 18%, 18.1%, 18.2%, 18.3%, 18.4%, 18.5%, 18.6%, 18.7%, 18.8%, 18.9%, 19%, 19.1%, 19.2%, 19.3%, 19.4%, 19.5%, 19.6%, 19.7%, 19.8%, 19.9% or 20%) of a moisturizing agent. The moisturizing agent can include, but is not limited to, one or more of panthenol, pantothenic acid derivatives, glycerin, glycerol, dimethicone, petrolatum, hyaluronic acid, or ceramides, and mixtures thereof.

According to some embodiments, the topical composition can include a vitamin $B_3$ compound. The vitamin B3 compound can be tocopherol nicotinate.

According to some embodiments, the topical composition can include an anti-oxidant. The anti-oxidant can be one or a combination of tocopherol or esters of tocopherol.

According to some embodiments, the topical composition can be in the form of a liquid, lotion, cream, gel, foam, mousse, spray, paste, powder, or solid.

According to some embodiments, a method is provided for regulating a human skin condition which includes applying to human skin at least once a day over at least seven days the topical composition described above. The method can include applying the topical composition to human skin at least twice a day over at least fourteen days.

The term "regulating a skin condition" includes one or more of inducing increased skin integrity by cell renewal; enhancing water content or moisture of skin; reducing trans epidermal water loss, skin flaking, and scaling; improving skin thickness; enhancing skin tensile properties; reducing the appearance of dermal fine lines and wrinkles; improving skin texture; reducing skin pores size; enhancing skin smoothness; improving skin age spots; improving skin tone; or improving the appearance of scars and skin abrasions.

According to some embodiments, a method is provided for tissue repair, the method including one of putting on, embedding into, filling, and injecting a tissue with a composition comprising components of amniotic fluid produced by a process described herein. According to some embodiments, the process for producing a composition comprising components of amniotic fluid comprises: (a) transferring at least one of cell types selected from the group consisting of: (i) amniotic fluid cells, (ii) amniotic membrane cells, (iii) placenta cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; and (d) ensuring the sterility of the conditioned supernatant. The defined medium essentially free of serum can consist of a base media, one or more of monothioglycerol, lipids, or polyvinyl alcohol, and optionally one or more antibiotics.

According to some embodiments, the process for producing a composition comprising components of amniotic fluid, comprises: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition comprising components of amniotic fluid.

According to some embodiments, the tissue can be repaired by the putting on, embedding into, filling, or injecting of the tissue with the composition comprising the active components of amniotic fluid, without the significant variability associated with amniotic fluid derived from a single donor.

According to some embodiments, the tissue repair can include, but is not limited to, repair of dermal, scar, cartilage, tendon, ligament, muscle, bone, periodontal, cardiovascular, hematologic, pulmonary, urologic, ophthalmic, liver, or kidney tissue, or combinations thereof.

According to some embodiments, the term "tissue repair" can include, but is not limited to, promotion of cell/tissue homeostasis, reducing inflammation, repair of wounds and burns, infection treatment, sepsis treatment, repair of scarring, preventing post-operative scarring, joint repair, rheumatoid arthritis treatment, psoriatic arthritis treatment, gout treatment, bursitis treatment, joint replacement surgery, tendon repair, tendinitis treatment, rotator cuff repair, muscle repair, repair, osteoarthritis treatment, arthritis treatment, male urologic dysfunction treatment, Critical Limb Ischemia treatment, Intermittent Claudication treatment, Buerger's Disease treatment, Ischemic Heart Disease treatment, Diastolic Heart Failure treatment, bronchopulmonary dysplasia, chronic obstructive pulmonary disease, ophthalmic disorders, and reversal of aging. According to some embodiments, the composition produced according to the process described herein containing active components of amniotic fluid is a dermal, cartilage, or bone gel.

Wound Healing

A wound results from damage or disruption to normal anatomical structure and function (Robson M C et al., Curr Probl Surg 2001; 38: 72-140; Velnar T et al., The Journal of International Medical Research 2009; 37: 1528-1542). This can range from a simple break in the epithelial integrity of the skin to deeper, subcutaneous tissue with damage to to other structures such as tendons, muscles, vessels, nerves, parenchymal organs and even bone (Alonso J E et al., Surg Clin North Am 1996; 76: 879-903). Irrespective of the cause and form, wounding damages and disrupts the local tissue environment.

Wound healing is a dynamic, interactive process involving soluble mediators, blood cells, extracellular matrix, and parenchymal cells. The wound repair process can be divided into four (4) temporally and spatially overlapping phases: (1) a coagulation phase; (2) an inflammatory phase, (3) a proliferative phase, and (4) a remodeling phase. Much of what is known is based on wound healing of human skin.

Coagulation Phase

Immediately after injury, platelets adhere to damaged blood vessels, initiate a release reaction, and begin a hemostatic reaction, giving rise to a blood-clotting cascade that prevents excessive bleeding and provides provisional protection for the wounded area. Blood platelets release well over a dozen growth factors, cytokines, and other survival or apoptosis-inducing agents (Weyrich A S and Zimmerman G A, Trends Immunol 2004 September; 25(9): 489-495). Key components of the platelet release reaction include platelet-derived growth factor (PDGF) and transforming growth factors A1 and 2 (TGF-A1 and TGF-2), which attract inflammatory cells, such as leukocytes, neutrophils, and macrophages (Singer A F and Clark R A, N Engl J Med 1999 Sep. 2; 341(10): 738-746).

Inflammatory Phase

The inflammatory phase is triggered by capillary damage, which leads to the formation of a blood clot/provisional matrix composed of fibrin and fibronectin. This provisional matrix fills the tissue defect and enables effector cell influx. Platelets present in the clot release multiple cytokines that participate in the recruitment of inflammatory cells (such as neutrophils, monocytes, and macrophages, amongst others), fibroblasts, and endothelial cells (ECs).

Proliferative Phase

The inflammatory phase is followed by a proliferative phase, in which active angiogenesis creates new capillaries, allowing nutrient delivery to the wound site, notably to support fibroblast proliferation. Fibroblasts present in granulation tissue are activated and acquire a smooth muscle cell-like phenotype, then being referred to as myofibroblasts. Myofibroblasts synthesize and deposit extracellular matrix (ECM) components that replace the provisional matrix. They also have contractile properties mediated by a-smooth muscle actin organized in microfilament bundles or stress fibers. Myofibroblastic differentiation of fibroblastic cells begins with the appearance of the protomyofibroblast, whose stress fibers contain only β- and γ-cytoplasmic actins. Protomyofibroblasts can evolve into differentiated myofibroblasts whose stress fibers contain α-smooth muscle actin.

Remodeling Phase

The fourth healing phase involves gradual remodeling of the granulation tissue and reepithelialization. This remodeling process is mediated largely by proteolytic enzymes, especially matrix metalloproteinases (MMPs) and their inhibitors (TIMPs, tissue inhibitors of metalloproteinases). During the reepithelialization, Type III collagen, the main component of granulation tissue, is replaced gradually by type I collagen, the main structural component of the dermis. Elastin, which contributes to skin elasticity and is absent from granulation tissue, also reappears. Cell density normalizes through apoptosis of vascular cells and myofibroblasts (resolution).

Inflammation

Tissue injury causes the disruption of blood vessels and extravasation of blood constituents. The blood clot re-establishes hemostasis and provides a provisional extracellular matrix for cell migration. Platelets not only facilitate the formation of a hemostatic plug but also secrete several mediators of wound healing, such as platelet-derived growth factor, which attract and activate macrophages and fibroblasts (Heldin, C. and Westermark B., In: Clark R., ed. The molecular and cellular biology of wound repair, 2nd Ed. New York, Plenum Press, pp. 249-273, (1996)). It was suggested, however, that, in the absence of hemorrhage, platelets are not essential to wound healing; numerous vasoactive mediators and chemotactic factors are generated by the coagulation and activated-complement pathways and by injured or activated parenchymal cells that were shown to recruit inflammatory leukocytes to the site of injury (Id.).

Ingress of cells into a wound and activation of local cells are initiated by mediators that are either released de novo by resident cells or from reserves stored in the granules of platelets and basophils. Sephel, G. C. and Woodward, S. C., 3. Repair, Regeneration and Fibrosis," in Rubin's Pathology, Rubin, R. and Strayer, D. S. Eds; 5th Ed., Wolters Kluwyer Health, /Lippincott Williams & Wilkins, Philadelphia, Pa. (2008), at 71. Cell migration uses the response of cells to cytokines and insoluble substrates of the extracellular matrix. Id. At 72.

Infiltrating neutrophils cleanse the wounded area of foreign particles and bacteria and then are extruded with the eschar (a dead tissue that falls off (sheds) from healthy skin or is phagocytosed by macrophages). In response to specific chemoattractants, such as fragments of extracellular-matrix protein, transforming growth factor 3 (TGF-β), and monocyte chemoattractant protein-1 (MCP-1), monocytes also infiltrate the wound site and become activated macrophages that release growth factors (such as platelet-derived growth factor and vascular endothelial growth factor), which initiate the formation of granulation tissue. Macrophages bind to specific proteins of the extracellular matrix by their integrin receptors, an action that stimulates phagocytosis of microorganisms and fragments of extracellular matrix by the macrophages (Brown, E. Phagocytosis, Bioessays, 17:109-117 (1995)). Studies have reported that adherence to the extracellular matrix also stimulates monocytes to undergo metamorphosis into inflammatory or reparative macrophages. These macrophages play an important role in the transition between inflammation and repair (Riches, D., In Clark R., Ed. The molecular and cellular biology of wound repair, 2nd Ed. New York, Plenum Press, pp. 95-141). For example, adherence induces monocytes and macrophages to express Colony-Stimulating Factor-1 (CSF-1), a cytokine necessary for the survival of monocytes and macrophages; Tumor Necrosis Factor-α (TNF-α), a potent inflammatory cytokine; and Platelet-Derived Growth Factor (PDGF), a potent chemoattractant and mitogen for fibroblasts. Other cytokines shown to be expressed by monocytes and macrophages include Transforming Growth Factor (TGF-α), Interleukin-1 (IL-1), Transforming Growth Factor β (TGF-β), and Insulin-like Growth Factor-I (IGF-I) (Rappolee, D. et al., Science, 241, pp. 708-712 (1988)). The monocyte- and macrophage-derived growth factors have been suggested to be necessary for the initiation and propagation of new tissue formation in wounds, because macrophage depleted animals have defective wound repair (Leibovich, S, and Ross, R., Am J Pathol, 78, pp 1-100 (1975)).

Epithelialization

Reepithelialization of wounds begins within hours after injury. Epidermal cells from skin appendages, such as hair follicles, quickly remove clotted blood and damaged stroma from the wound space. At the same time, the cells undergo phenotypic alteration that includes retraction of intracellular tonofilaments (Paladini, R. et al., J. Cell Biol, 132, pp. 381-397 (1996)); dissolution of most inter-cellular desmosomes, which provide physical connections between the cells; and formation of peripheral cytoplasmic actin filaments, which allow cell movement and migration (Goliger, J. and Paul, D. Mol Biol Cell, 6, pp. 1491-1501 (1995); Gabbiani, G. et al., J Cell Biol, 76, PP. 561-568 (1978)). Furthermore, epidermal and dermal cells no longer adhere to one another, because of the dissolution of hemidesmosomal links between the epidermis and the basement membrane, which allows the lateral movement of epidermal cells. The expression of integrin receptors on epidermal cells allows them to interact with a variety of extracellular-matrix proteins (e.g., fibronectin and vitronectin) that are interspersed with stromal type I collagen at the margin of the wound and interwoven with the fibrin clot in the wound space (Clark, R., J Invest Dermatol, 94, Suppl, pp. 128S-134S (1990)). The migrating epidermal cells dissect the wound, separating desiccated eschar (a dead tissue that falls off (sheds) from healthy skin) from viable tissue. The path of dissection appears to be determined by the array of integrins that the migrating epidermal cells express on their cell membranes.

The degradation of the extracellular matrix, which is required if the epidermal cells are to migrate between the collagenous dermis and the fibrin eschar, depends on the production of collagenase by epidermal cells (Pilcher, B. et al., J Cell Biol, 137, pp. 1445-1457 (1997)), as well as the activation of plasmin by plasminogen activator produced by the epidermal cells (Bugge, T. et al., Cell, 87, 709-719 (1996)). Plasminogen activator also activates collagenase (matrix metalloproteinase-1) (Mignatti, P. et al., Proteinases and Tissue Remodeling. In Clark, R. Ed. The molecular and cellular biology of wound repair. 2nd Ed. New York, Plenum Press, 427-474 (1996)) and facilitates the degradation of collagen and extracellular-matrix proteins.

One to two days after injury, epidermal cells at the wound margin begin to proliferate behind the actively migrating cells. The stimuli for the migration and proliferation of epidermal cells during reepithelialization have not been determined, but several possibilities have been suggested. The absence of neighbor cells at the margin of the wound (the "free edge" effect) may signal both migration and proliferation of epidermal cells. Local release of growth factors and increased expression of growth-factor receptors may also stimulate these processes. Leading contenders include Epidermal Growth Factor (EGF), Transforming Growth Factor-α (TGF-α), and Keratinocyte Growth Factor (KGF) (Nanney, L. and King, L. Epidermal Growth Factor and Transforming Growth Factor-α. In Clark, R. Ed. The molecular and cellular biology of wound repair. 2nd Ed. New York, Plenum Press, pp. 171-194 (1996); Werner, S. et al., Science, 266, pp. 819-822 (1994); Abraham, J. and Klagsburn, M. Modulation of Wound Repair by Members of the Fiborblast Growth Factor family. In Clark, R. Ed. The molecular and cellular biology of wound repair. 2nd Ed.

New York, Plenum Press, pp. 195-248 (1996)). As re-epithelialization ensues, basement-membrane proteins reappear in a very ordered sequence from the margin of the wound inward, in a zipper-like fashion (Clark R. et al., J. Invest Dermatol, 79, pp. 264-269 (1982)). Epidermal cells revert to their normal phenotype, once again firmly attaching to the reestablished basement membrane and underlying dermis.

Formation of Granulation Tissue

New stroma, often called granulation tissue, begins to invade the wound space approximately four days after injury. Numerous new capillaries endow the new stroma with its granular appearance. Macrophages, fibroblasts, and blood vessels move into the wound space at the same time (Hunt, T. ed. Wound Healing and Wound Infection: Theory and Surgical Practice. New York, Appleton-Century-Crofts (1980)). The macrophages provide a continuing source of growth factors necessary to stimulate fibroplasia and angiogenesis; the fibroblasts produce the new extracellular matrix necessary to support cell ingrowth; and blood vessels carry oxygen and nutrients necessary to sustain cell metabolism.

Growth factors, especially Platelet-Derived Growth Factor-4 (PDGF-4) and Transforming Growth Factor β-1 (TGF-β1) (Roberts, A. and Sporn, M, Transforming Growth Factor-1, In Clark, R. ed. The molecular and cellular biology of wound repair. 2nd Ed. New York, Plenum Press, pp. 275-308 (1996)) in concert with the extracellular-matrix molecules (Gray, A. et al., J Cell Sci, 104, pp. 409-413 (1993); Xu, J. and Clark, R., J Cell Biol, 132, pp. 239-149 (1996)), were shown to stimulate fibroblasts of the tissue around the wound to proliferate, express appropriate integrin receptors, and migrate into the wound space. It was reported that platelet-derived growth factor accelerates the healing of chronic pressure sores (Robson, M. et al., Lancet, 339, pp. 23-25 (1992) and diabetic ulcers (Steed, D., J Vasc Surg, 21, pp. 71-78 (1995)). In some other cases, basic Fibroblast Growth Factor (bFGF) was effective for treating chronic pressure sores (Robson, M. et al., Ann Surg, 216, pp. 401-406 (1992).

The structural molecules of newly formed extracellular matrix, termed the provisional matrix (Clark, R. et al., J. Invest Dermatol, 79, pp. 264-269, 1982), contribute to the formation of granulation tissue by providing a scaffold or conduit for cell migration. These molecules include fibrin, fibronectin, and hyaluronic acid (Greiling, D. and Clark R., J. Cell Sci, 110, pp. 861-870 (1997)). The appearance of fibronectin and the appropriate integrin receptors that bind fibronectin, fibrin, or both on fibroblasts was suggested to be the rate-limiting step in the formation of granulation tissue. While the fibroblasts are responsible for the synthesis, deposition, and remodeling of the extracellular matrix, the extracellular matrix itself can have a positive or negative effect on the ability of fibroblasts to perform these tasks, and to generally interact with their environment (Xu, J. and Clark, R., J Cell Sci, 132, pp. 239-249 (1996); Clark, R. et al., J Cell Sci, 108, pp. 1251-1261).

Cell movement into a blood clot of cross-linked fibrin or into tightly woven extracellular matrix requires an active proteolytic system that can cleave a path for cell migration. A variety of fibroblast-derived enzymes, in addition to serum-derived plasmin, are suggested to be potential candidates for this task, including plasminogen activator, collagenases, gelatinase A, and stromelysin (Mignatti, P. et al., Proteinases and Tissue Remodeling. In Clark, R. Ed. The molecular and cellular biology of wound repair. 2nd Ed. New York, Plenum Press, 427-474 (1996); Vaalamo, M. et al., J Invest Dermatol, 109, pp. 96-101 (1997)). After migrating into wounds, fibroblasts commence the synthesis of extracellular matrix. The provisional extracellular matrix is replaced gradually with a collagenous matrix, perhaps in response to Transforming Growth Factor-131 (TGF-β1) signaling (Clark, R. et al., J Cell Sci, 108, pp. 1251-1261 (1995); Welch, M. et al., J. Cell Biol, 110, pp. 133-145 (1990))

Once an abundant collagen matrix has been deposited in the wound, the fibroblasts stop producing collagen, and the fibroblast-rich granulation tissue is replaced by a relatively acellular scar. Cells in the wound undergo apoptosis triggered by unknown signals. It was reported that dysregulation of these processes occurs in fibrotic disorders, such as keloid formation, hypertrophic scars, morphea, and scleroderma.

Neovascularization

The formation of new blood vessels (neovascularization) is necessary to sustain the newly formed granulation tissue. Angiogenesis is a complex process that relies on extracellular matrix in the wound bed as well as migration and mitogenic stimulation of endothelial cells (Madri, J. et al., Angiogenesis in Clark, R. Ed. The molecular and cellular biology of wound repair. 2nd Ed. New York, Plenum Press, pp. 355-371 (1996)). The induction of angiogenesis was initially attributed to acidic or basic Fibroblast Growth Factor. Subsequently, many other molecules have also been found to have angiogenic activity, including vascular endothelial growth factor (VEGF), Transforming Growth Factor-β (TGF-β), angiogenin, angiotropin, angiopoietin-1, and thrombospondin (Folkman, J. and D'Amore, P, Cell, 87, pp. 1153-1155 (1996)).

Low oxygen tension and elevated lactic acid were suggested also to stimulate angiogenesis. These molecules induce angiogenesis by stimulating the production of basic Fibroblast Growth Factor (FGF) and Vascular Endothelial Growth Factor (VEGF) by macrophages and endothelial cells. For example, it was reported that activated epidermal cells of the wound secrete large quantities of Vascular Endothelial cell Growth Factor (VEGF) (Brown, L. et al., J Exp Med, 176, 1375-1379 (1992)).

Basic fibroblast growth factor was hypothesized to set the stage for angiogenesis during the first three days of wound repair, whereas vascular endothelial-cell growth factor is critical for angiogenesis during the formation of granulation tissue on days 4 through 7 (Nissen, N. et al., Am J Pathol, 152, 1445-1552 (1998)).

In addition to angiogenesis factors, it was shown that appropriate extracellular matrix and endothelial receptors for the provisional matrix are necessary for angiogenesis. Proliferating microvascular endothelial cells adjacent to and within wounds transiently deposit increased amounts of fibronectin within the vessel wall (Clark, R. et al., J. Exp Med, 156, 646-651 (1982)). Since angiogenesis requires the expression of functional fibronectin receptors by endothelial cells (Brooks, P. et al., Science, 264, 569-571 (1994)), it was suggested that perivascular fibronectin acts as a conduit for the movement of endothelial cells into the wound. In addition, protease expression and activity were shown to also be necessary for angiogenesis (Pintucci, G. et al., Semin Thromb Hemost, 22, 517-524 (1996)).

The series of events leading to angiogenesis has been proposed as follows. Injury causes destruction of tissue and hypoxia. Angiogenesis factors, such as acidic and basic Fibroblast Growth Factor (FGF), are released immediately from macrophages after cell disruption, and the production of vascular endothelial-cell growth factor by epidermal cells is stimulated by hypoxia. Proteolytic enzymes released into the connective tissue degrade extracellular-matrix proteins. Fragments of these proteins recruit peripheral-blood monocytes to the site of injury, where they become activated macrophages and release angiogenesis factors. Certain macrophage angiogenesis factors, such as basic fibroblast growth factor (bFGF), stimulate endothelial cells to release plasminogen activator and procollagenase. Plasminogen activator converts plasminogen to plasmin and procollagenase to active collagenase, and in concert these two proteases digest basement membranes. The fragmentation of the basement membrane allows endothelial cells stimulated by angiogenesis factors to migrate and form new blood vessels at the injured site. Once the wound is filled with new granulation tissue, angiogenesis ceases and many of the new blood vessels disintegrate as a result of apoptosis (Ilan, N. et al., J Cell Sci, 111, 3621-3631 (1998)). This programmed cell death has been suggested to be regulated by a variety of matrix molecules, such as thrombospondins 1 and 2, and anti-angiogenesis factors, such as angiostatin, endostatin, and angiopoietin 2 (Folkman, J., Angiogenesis and angiogenesis inhibition: an overview, EXS, 79, 1-8, (1997)).

Wound Contraction and Extracellular Matrix Reorganization

Wound contraction involves a complex and orchestrated interaction of cells, extracellular matrix, and cytokines During the second week of healing, fibroblasts assume a myofibroblast phenotype characterized by large bundles of actin-containing microfilaments disposed along the cytoplasmic face of the plasma membrane of the cells and by cell-cell and cell-matrix linkages (Welch, M. et al., J Cell Biol, 110, 133-145 (1990); Desmouliere, A. and Gabbiani, G. The role of the myofibroblast in wound healing and fibrocontractive diseases. In Clark, R. Ed. The molecular and cellular biology of wound repair. 2nd Ed. New York, Plenum Press, pp. 391-423 (1996)). The appearance of the myofibroblasts corresponds to the commencement of connective-tissue compaction and the contraction of the wound. This contraction was suggested to require stimulation by Transforming Growth Factor (TGF)-$\beta$1 or $\beta$2 and Platelet-Derived Growth Factor (PDGF), attachment of fibroblasts to the collagen matrix through integrin receptors, and cross-links between individual bundles of collagen. (Montesano, R. and Orci, Proc Natl Acad Sci USA, 85, 4894-4897 (1988); Clark, R. et al., J Clin Invest, 84, 1036-1040 (1989); Schiro, J. et al., Cell, 67, 403-410 (1991); Woodley, D. et al., J Invest Dermatol, 97, 580-585 (1991)).

Collagen remodeling during the transition from granulation tissue to scar is dependent on continued synthesis and catabolism of collagen at a low rate. The degradation of collagen in the wound is controlled by several proteolytic enzymes, termed matrix metalloproteinases (MMP), which are secreted by macrophages, epidermal cells, and endothelial cells, as well as fibroblasts (Mignatti, P. et al., Proteinases and Tissue Remodeling. In Clark, R. Ed. The molecular and cellular biology of wound repair. 2nd Ed. New York, Plenum Press, 427-474 (1996)). Various phases of wound repair have been suggested to rely on distinct combinations of matrix metalloproteinases and tissue inhibitors of metalloproteinases (Madlener, M. et al, Exp Cell Res, 242, 201-210 (1998)).

Wounds gain only about 20 percent of their final strength in the first three weeks, during which fibrillar collagen has accumulated relatively rapidly and has been remodeled by contraction of the wound. Thereafter, the rate at which wounds gain tensile strength is slow, reflecting a much slower rate of accumulation of collagen and collagen remodeling with the formation of larger collagen bundles and an increase in the number of intermolecular cross-links.

According to certain aspects, a method is provided for wound healing, the method including one of topically administering, putting on, embedding into, filling, and injecting a wound with a composition comprising components of amniotic fluid produced by a process described herein. According to some embodiments, the process for producing a composition comprising components of amniotic fluid comprises: (a) transferring at least one of cell types selected from the group consisting of: (i) amniotic fluid cells, (ii) amniotic membrane cells, (iii) placenta cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; and (d) ensuring the sterility of the conditioned supernatant. The defined medium essentially free of serum can consist of a base media, one or more of monothioglycerol, lipids, or polyvinyl alcohol, and optionally one or more antibiotics.

According to some embodiments, the process for producing a composition comprising components of amniotic fluid, comprises: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition comprising components of amniotic fluid.

According to some embodiments, the present invention also contemplates methods of enhancing the rate of wound healing with the administration of the pharmaceutical compositions describe herein to a wounded animal. Such an enhancement will frequently also involve an increase in the collagen content of a wounded area.

Collagen production is vital for the wound healing process. Collagen is the most prevalent protein in animals. It is an obligatory constituent of connective tissues and extra cellular matrices. Collagen networks in the tissues are responsible for establishing and maintaining the physical integrity of diverse extra cellular structures. Collagen, at molecular level, is defined as a protein comprised of lengthy domains of triple-helical confirmation. Collagenous scaffolding of extra cellular matrix comprises of 13 genetically distinct types of collagen. During the normal wound repair, collagen neosynthesis and deposition of type III collagen is demonstrated in the earliest phase, i.e. 24 hr to 48 hr, period. From that point, a significant increase in type I collagen is associated with the mature wound fibroblasts and subsequent healing events. Because of its important role in the wound healing process, collagen production is a measure of the rate and quality of wound healing. As such, assays that measure collagen production are useful in experimental models to study wound healing.

Collagenase plays a significant role in wound healing. In the wound repair process, collagen synthesis and accumulation is important. Careful and appropriate degradation of collagen is very important in wound healing repair and tissue formation. The collagen fibril, formed as required by aggregation of collagen monomers, is extremely effective structural element for maintaining the integrity of the newly formed connective tissue. These fibrils are physically stable up to 50° C. and are chemically resistant. Fibrillar collagen is essentially insoluble under normal physiological conditions. It is resistant to degradation action of a wide range of naturally occurring proteolytic enzymes. However, host cells have the ability for endogenous production of specific enzymes-collagenases-which act primarily on collagen. These enzymes, by proteolytic cleavage denature each of collagen fibers. Thus for appropriate wound healing and formation of repair-tissue its structural integrity endogenous production of collagenase is essential. The measurement of collagenase in wound tissue is an indicator of wound healing strength. For this assay, one can use a collagenase assay system such as the one available from New England Nuclear (NEN-cat #NEK016), employing 3H-collagen. Collagenolytic activity is monitored with a high specific activity substrate by quantitating the production of soluble radioactive fragments, which are readily separated from undigested collagen fibrils by centrifugation.

Studies can be conducted to determine whether the pharmaceutical compositions described herein improve wound bursting (tensile) strength. The reparative collagen and its fibers deposition attributes to the strength of the tissue which is measured by the model described by Nelsen and Anders (1966), referred in the reference section and specifically incorporated herein in pertinent part. This method involves testing the bursting strength of the wound by distention with either air or water. The traction method of testing bursting strength can also be employed.

According to some embodiments, the pharmaceutical compositions described herein may be administered before, during, immediately following wounding, for example, or within about 180, about 120, about 90, about 60, or about 30 days, but preferably within about 10, about 9, about 8, about 7, about 6, about 5, about 4, about 3, or about 2 days or less, and most preferably within about 24, about 12, about 10, about 9, about 8, about 7, about 6, about 5, about 4, about 3, about 2 hours or within about 60, about 45, about 30, about 15, about 10, about 5, about 4, about 3, about 2, about 1 minute following wounding, for example.

According to some aspects, methods of the disclosure also encompass a pretreatment regimen for enhancing the rate of wound healing in an animal that is to undergo surgery. The pretreatment period can be, e.g., between about 1 week to about 4 weeks, between about 1 week to about 3 weeks, between about 1 week to about 2 weeks. In some embodiments, the pretreatment period can be more than 4 weeks, for example about 4 or more, 5 or more, 6 or more, 7 or more or 8 or more weeks.

According to some embodiments, the pharmaceutical compositions as described herein are provided in combination with a wound dressing or wound healing promoting matrix. The term "dressing" refers to a dressing for topical application to a wound and excludes compositions suitable for systemic administration. For example, the pharmaceutical compositions described herein may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In certain embodiments the pharmaceutical compositions described herein are dispersed in or on a biodegradable sheet material that provides sustained release of the active ingredients into the wound, for example a sheet of freeze-dried collagen, freeze-dried collagen/alginate mixtures or freeze-dried collagen/oxidized regenerated cellulose (Johnson & Johnson). As used herein, "matrix" includes for example, matrices such as collagen, acellular matrix, crosslinked biological scaffold molecules, tissue based bioengineered structural framework, biomanufactured bioprostheses, and other implanted structures such as for example, vascular grafts suitable for cell infiltration and proliferation useful in the promotion of wound healing. Additional suitable biomatrix material may include chemically modified collagenous tissue to reduce antigenicity and immunogenicity. Other suitable examples include collagen sheets for wound dressings, antigen-free or antigen reduced acellular matrix (Wilson et al., Trans Am Soc Artif Intern 1990; 36:340-343) or other biomatrix which have been engineered to reduce the antigenic response to the xenograft material. Other matrix useful in promotion of wound healing may include for example, processed bovine pericardium proteins comprising insoluble collagen and elastin (Courtman et al., J Biomed Mater Res 1994; 28:655-666) and other acellular tissue which may be useful for providing a natural microenvironment for host cell migration to accelerate tissue regeneration (Malone et al., J Vase Surg 1984; 1:181-91). In certain embodiments, the matrix material may be supplemented with agents useful for wound healing such as growth factors or other wound healing promoting agents for site specific release, therapeutic agents, and/or gap junction modifying agents.

According to some embodiments, the compositions described herein may reduce aging-associated muscle/muscle stem cell degeneration; may promote muscle stem cell differentiation, viability, proliferation.

Organ Preservation

Organ transplantation remains the final solution for patients with end-stage organ failure. However, the limited number of physiologically functional donor organs causes a continuous increase in the number of patients on waiting lists for transplantation. Adequate preservation of organs intended for transplantation is critical to the proper functioning of the organ following implantation.

Different organ perfusion systems have been developed and implemented in clinical practice in order to maintain the viability of organs ex vivo. (See, e.g., Van Raemdonck, D. et al., Curr. Opin. Organ Transplant. (2013) 18: 24-33). The development of such perfusion systems in which biomechanical and biophysiological conditions can be adjusted to mimic the physiological environment, allows safe ex vivo organ preservation for longer periods of time and reduces ischemic time. See Ciubotaru, A., Haverrich, A., Eur. Surg. Res. (2015) 54: 64-74). Ex vivo organ perfusion providing oxygen and nutrients under physiological conditions and removing toxic metabolic products permits improvement of organ function and organ reconditioning, which allows the recovery of organs which otherwise have been rejected for transplant. Id. Many different organ preservation solutions have been designed, as investigators have sought to lengthen the time that an organ may remain extra-corporeally, as well as to maximize function of the organ following implantation. Several of the key solutions that have been used over the years include: 1) the Stanford University solution [see, e.g., Swanson, D. K., et al., Journal of Heart Transplantation, (1988), vol. 7, No. 6, pages 456-467 (mentions composition of the Stanford University solution)]; 2) a modified Collins solution [see, e.g., Maurer, E. J., et al., Transplantation Proceedings, (1990), vol. 22, No. 2, pages 548-550; Swanson, D. K., et al., supra (mention composition of modified Collins solution)]; and 3) the University of Wisconsin solution (Belzer, et al., U.S. Pat. No. 4,798,824, issued Jan. 17, 1989).

Organ preservation is the supply line for organ transplantation. Preservation by cooling is believed necessary to reduce cellular metabolism and the requirements for oxygen to prevent tissue injury. The physiopathological processes responsible for transplant injuries are defined as ischaemia/reperfusion injury (IRI) in organ transplantation. Guibert, E. E. et al, Transfus. Med. Hemother. (2011) 38(2): 125-142). Although the chilling of organs has harmful repercussions on the tissues due to oxidative stress (production of reactive oxygen species) and inflammation (cytokine production), which may be responsible for the exacerbation and, above all, persistence of this condition, it is one of the most widespread methods to preserve organs for transplant. Id.

There are two approaches for preservation of most transplantable organs static preservation, e.g., cold storage (SCS), which relies on the effects of cooling alone, supplemented by the use of preservation solutions aimed at modifying cellular molecular changes, and dynamic preservation (e.g., machine perfusion-based methods), which depends on activating residual metabolism, which is largely dependent on a need for oxygen supply for aerobic metabolism delivered by vascular perfusion. Id.

Hypothermic storage is the most common method for whole organs using one of the two methods described above For example, Collins introduced artificial preservation solutions based on a combination of high potassium ion content and osmotic barrier supported by glucose, which was associated with a shorting of storage time. (Id. Citing Collins, et al, Br. J. Surg. (1972) 59: 187-89). Collins solutions permitted successful renal preservation for 24-36 h, which was long enough to allow tissue matching and sharing of organs between transplant centers.

Preservation of liver, pancreas and kidney is possible for up to two days by flushing the organs with the University of Wisconsin (UW) organ preservation solution and storing them at 0-5 degrees C. Southard, James H. and Belzer, Folkert O., Ann. Rev. Med. (1995) 46: 235-47). The UW solution, which is the g old standard for preservation of liver grafts, uses a number of cell impermeant agents (lactobionic acid, raffinose, hydroxyethyl starch) that prevent the cells from swelling during cold ischemic storage, and contains glutathione and adenosine, that may stimulate recovery of normal metabolism upon reperfusion by augmenting the antioxidant capacity of the organs (glutathione) or by stimulating high-energy phosphate generation (adenosine upon reperfusion. Although this method of organ preservation is effective, some organs (5-15% of livers and 20-30% of kidneys) do not function well upon transplant. Injury may be preservation related but may also result from donor and recipient factors that render the organs more susceptible to preservation damage. Id. Results with continuous perfusion of kidneys in the clinics, however, show a reduction in preservation/reperfusion damage. Id.

Histidine-tryptophane-ketoglutarate (HTK) solution was introduced by H J. Bretschneider initially for cardiac surgery. Guibert, E. E. et al, Transfus. Med. Hemother. (2011) 38(2): 125-142). It was shown to be effective in both liver and kidney preservation. Major components are a strong buffer (histidine), osmotic barrier(mannitol), and low-permeable amino acids (tryptophan and alpha-ketoglutaric acid) which help to stabilize cell membranes and may be substrates for anaerobic metabolism. Id.

Celsior solution is an extracellular-type solution (high Na+) that adopted many of the principles of UW solution (lactobionate and mannitol) and the strong buffer from Bretschneider's HTK solution (histidine). Guibert, E. E. et al, Transfus. Med. Hemother. (2011) 38(2): 125-142). In contrast to UW solution, reduced glutathione is the only antioxidant available in this solution. Initially designed for heart transplantation, it is now being clinically tested in other abdominal organs. The solution provides excellent lung preservation and proved to be effective in experiments with pancreas preservation and kidney storage. Id.

According to some embodiments a method is provided for preservation of an organ, the method comprising surrounding the organ in a composition comprising components of amniotic fluid wherein the composition is produced by a process comprising: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (e) ensuring sterility of the conditioned supernatant, wherein the sterile conditioned supernatant is the composition comprising components of amniotic fluid, wherein the organ is preserved in the composition.

According to some embodiments, the organ is the heart, liver, pancreas, kidney, or lungs.

According to some embodiments, the compositions described herein enhance engraftment by its use as basal media incubation prior to cell transplantation to relevant compartments.

According to some embodiments, the composition comprising components of amniotic fluid may also comprise nitroglycerin. According to one embodiment, the concentration of nitroglycerin ranges from about 0.05 g/l to about 0.2 g/l. According to some embodiments, the composition comprising components of amniotic fluid may also comprise adenosine. According to one embodiment, the concentration of adenosine ranges from about 3 mM to about 20 mM. According to some embodiments, the composition comprising components of amniotic fluid may also comprise D-glucose in an amount sufficient to support intracellular function and maintenance of cellular bioenergetics. According to one embodiment, the concentration of D-glucose ranges from about 50 mM to about 80 mM. According to some embodiments, the composition comprising components of amniotic fluid may also comprise magnesium ions in an amount sufficient to support intracellular function and maintenance of cellular bioenergetics. According to one embodiment, the concentration of magnesium ions ranges from about 2 mM to about 10 mM. According to some embodiments, the composition comprising components of amniotic fluid may also comprise potassium ions in an amount sufficient to support intracellular function and maintenance of cellular bioenergetics. According to one embodiment, the concentration of potassium ions is greater than 110 mM. According to one embodiment, the concentration of potassium ions is between about 110 mM to about 140 mM. According to some embodiments, the composition comprising components of amniotic fluid may also comprise an anticoagulant in an amount sufficient to help prevent clotting of blood within the capillary bed of the organ. The anticoagulant is selected from the group consisting of heparin or hirudin. Other suitable anticoagulants may be used. In a preferred embodiment, the concentration of heparin ranges from about 1000 units/l to about 100,000 units/l. According to some embodiments, the composition comprising components of amniotic fluid may also comprise an antioxidant in an amount sufficient to help decrease reperfusion injury secondary to oxygen free radicals. The antioxidant is selected from the group consisting of butylated hydroxyanisole (BHA), butylated hydroxytoluene (BHT), Vitamin C, Vitamin E, or suitable combinations thereof. Other suitable antioxidants may be used.

The osmolarity of the composition is also a factor in helping to prevent cellular swelling and rupture. The osmolarity of the composition must be greater than the cellular osmolarity. Cellular osmolarity is about 290 mOSm/l. In a preferred embodiment, the osmolarity ranges from about 315 mOSm/l to about 340 mOSm/l.

In a preferred embodiment, the initial pH of the composition is adjusted to the alkaline side of normal physiologic pH because then the average pH during storage of the organ in the organ preservation or maintenance solution remains physiologic. Normal physiologic pH is about 7.4. A preferred embodiment of the composition has a pH range of about 7.4 to about 7.6. The pH may be adjusted to the desired value with the addition of a suitable base, such as potassium hydroxide (KOH). Hence, during the period of organ preservation, the pH of the compositions starts on the alkaline side of physiologic pH, and may drift slowly down to the acidic side of physiologic pH. But the average pH of the composition during the period of organ preservation is about the physiologic value.

The amount of the composition comprising components of amniotic fluid required in an organ transplantation or surgical procedure (such as a cardioplegic agent during cardiac surgery) would be obvious to one who is skilled in such organ transplantation or surgical procedures. The composition comprising components of amniotic fluid is suitable for use at the low temperatures that may be required during an organ transplantation or other surgical procedure. For instance, temperatures of about zero to about four degrees Centigrade may be required during an organ transplantation or surgical procedure.

According to some embodiments, the compositions described herein may enhance cell viability and/or proliferation and/or homeostasis as a read-out for enhancement of organ transplantation, as an organ transplant media or addition to organ transplant media solution.

According to some embodiments, a heterotopic rat heart transplant model is used to examine the comparative effectiveness of the composition comprising components of amniotic fluid described herein. The heterotopic rat heart transplant model involves harvesting a heart following cold cardioplegic arrest, and then flushing the aortic root with preservation solution until the coronary arteries become visibly clear. Following a period of preservation, the heart is then transplanted into a recipient rat's abdomen with the aortic root being anastomosed to the recipient's abdominal aorta, and the pulmonary artery being anastomosed to the recipient's inferior vena cava. This permits normal coronary artery perfusion of the transplanted heart following implantation. A heterotopic rat heart transplant model is described, for example, in U.S. Pat. No. 5,552,267, incorporated by reference in its entirety herein.

According to some embodiments, the compositions described herein may serve as a superior basal or stand-alone media to aid in many different processes during in vitro cell culture, including, but not limited to stem cell differentiation, primary cell expansion, activating EMT for basic science and/or therapeutic purposes, propagating cells procured from a donor that will be re-introduced into a patient (autologous or otherwise).

Liver Cell Engraftment

The body depends on the liver to perform a number of vital functions, including regulation, synthesis, and secretion of many substances important in maintaining the body's normal state; storage of important nutrients such as glycogen (glucose), vitamins, and minerals; and purification, transformation, and clearance of waste products, drugs, and toxins. However, its distinctive characteristics and activities render it susceptible to damage from a variety of sources, and such damage can have enormous impact on a person's health.

The most abundant and metabolically active cells in the liver are the hepatocytes. The lobules of the liver are hexagonal in shape, with six portal triads at the periphery, each containing a branch of the portal vein, a branch of the hepatic artery, and a bile duct, all held tightly together by a layer of hepatocytes. Hepatocytes rarely divide, but they have a unique capacity to reproduce in response to an appropriate stimulus, such as the removal of a portion of liver. This process involves controlled hyperplasia, that usually restores the liver to within 5 to 10% of its original weight.

The liver has a unique capacity to regenerate after injury. The process begins with proliferation of "mature" hepatocytes; other cell lineages including biliary epithelial cells (BEC) and sinusoidal cells proliferate somewhat later. Liver regeneration plays an important role after partial hepatectomy and after injuries that destroy portions of the liver, such as viral, toxic, or ischemic damage. However, excessive damage can reach a "point of no return", and normal tissue is then replaced with scar tissue. The liver's ability to regenerate is also compromised by pre-existing or repeated liver damage or disease.

As used herein, the term "liver engrafting cells" refers to a progenitor cell population that, when transplanted into an animal, gives rise to mature hepatocytes. The developmental potential of liver progenitor cells can be assessed by functional and phenotypic criteria. Functionally, hepatocytes are characterized by their ability to complement FAH deficiency, and by the expression of liver specific proteins, including albumin, alpha-1-antitrypsin, alpha fetoprotein, etc. Hepatocytes are also functionally characterized by their ability to be infected by hepatitis viruses, e.g. Hepatitis A (HAV); Hepatitis B (HBV), hepatitis C (HCV); Hepatitis D (HDV); Hepatitis E (HEV); etc. According to some embodiments, liver engrafting cells can be characterized by their expression of cell surface markers. The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

According to some embodiments, the compositions described herein may enhance engraftment by using as basal media for EP/eEP/HP/HLC/AEC/AEC-derived cell/PSC-derived cell incubation. Without being bound by theory, it is thought that the compositions described herein may enhance engraftment by inducing epithelial-to-mesenchymal transition (or another cell state) prior to cell transplantation to the liver, thereby enhancing and/or quantitatively increasing the overall engraftment into the liver.

According to some embodiments, liver engrafting cells are separated from a complex mixture of cells by techniques that enrich for cells having certain characteristics as described herein. For example, a population of cells may be selected from anR2 population, for expression of one or more of 5E12, e-cadherin, ep-cam and CD49f. The cells are optionally selected for low or negative expression of HLA Class I antigens (herein termed HLA low). CD54 and CD38 may be used interchangeably with HLA.

For isolation of cells from tissue, an appropriate solution may be used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The subject cells are large, blast cells, therefore an initial separation may select for large cells by various methods known in the art, including elutriation, Ficoll-Hypaque or flow cytometry using the parameters of forward and obtuse scatter to gate for blast cells Separation of the subject cell population may then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. The details of the preparation of antibodies and their suitability for use as specific binding members are well known to those skilled in the art.

According to some embodiments, the compositions described herein enhance engraftment by using as basal media for MSC/BMSC/AMSC, etc incubation prior to cell transplantation to relevant compartments.

According to some embodiments, cell populations enriched for liver engrafting activity are achieved in this manner. The subject population will be at or about 50% or more of the cell composition, and usually at or about 90% or more of the cell composition, and may be as much as about 95% or more of the live cell population. The-enriched cell population may be used immediately, or may be frozen at liquid nitrogen temperatures and stored for long periods of time, being thawed and capable of being reused. Once thawed, the cells may be expanded by use of growth factors and/or stromal cells for proliferation and differentiation.

According to some embodiments, the liver engrafting cells are positive for expression of 5E12 antigen. According to some embodiments, the liver engrafting cells are positive for expression of EpCam. According to some embodiments, the liver engrafting cells are positive for expression of E-Cadherin. According to some embodiments, the liver engrafting cells are positive for expression of CD49f. According to some embodiments, the liver engrafting cells are positive for expression of HLA Class I.

Functional assays may be performed using in vitro cultured cells. For example, cultured cells may be assessed for their ability to express liver specific proteins, including albumin and alpha-1 antitrypsin. Expression may utilize any convenient format, including RT-PCR, ELISA for presence of the protein in culture supernatants, etc. Cultured cells may also be assessed for their ability to express bile duct proteins, e.g. CK19.

Hepatic failure involves the systemic complications associated with severe liver injury and dysfunction. It may occur in a patient without pre-existing liver disease or may be superimposed on chronic liver injury. The diagnosis of acute liver failure requires the presence of symptoms, including jaundice and encephalopathy. Fulminant hepatic failure impairs all liver functions, causing decreased bilirubin metabolism, decreased clearance of ammonia and gut-derived proteins, and decreased clotting factor production. It may also cause kidney failure, shock, and sepsis. Without a liver transplant, more than 50% of patients will die, usually from a combination of the above conditions. Mortality exceeds 50%, even in the best circumstances. Management involves general supportive measures until the liver can regenerate and resume function. In acute liver failure without pre-existing disease, liver transplant can be life-saving.

According to some embodiments, the subject cells may be used for reconstitution of liver function in a recipient.

Treatment of Respiratory Disorders

Chronic obstructive airway disease (COPD) is a pulmonary (lung) disease characterized by chronic obstruction of the airways. COPD encompasses emphysema and chronic bronchitis. Chronic bronchitis is diagnosed where a patient suffers from chronic cough, mucus production, or both, for at least three months in at least two successive years where other causes of chronic cough have been excluded. In chronic bronchitis, airway obstruction is caused by chronic and excessive secretion of abnormal airway mucus, inflammation, and bronchospasm. Often chronic bronchitis is exacerbated by frequent or chronic infection. Emphysema involves the destruction of elastin in terminal bronchioles, which leads to remodeling, destruction and ultimate collapse of the airway walls. Patients with emphysema gradually lose the ability to exhale, causing a rise in blood waste gasses (such as carbon dioxide), a drop in blood oxygen, and a general degradation of patient stamina and overall health. A characteristic of emphysema is permanent loss of alveoli. Remodeling leads to permanent enlargement of the air spaces distal to the terminal bronchioles, and destruction of terminal bronchiole walls, though without fibrosis.

According to some embodiments, the disclosure relates to methods for the use of inhalation solutions (e.g. compositions comprising components of amniotic fluid) in an inhalation device for the treatment or prophylaxis of a respiratory condition in a patient, such as COPD, chronic bronchitis, or emphysema. In some embodiments, the methods comprise administering to the patient a nominal dose of one or more API, for example compositions comprising components of amniotic fluid as described herein, in an aqueous inhalation solution with an inhalation device, e.g. a high efficiency nebulizer or a conventional nebulizer a high efficiency nebulizer, conventional nebulizer, and optionally a conventional inhalation device.

According to some embodiments, the compositions described herein may be used to treat COPD. According to some embodiments, the compositions described herein are lyophilized, and stored as a powder.

Inhalation Therapy

An inhalation device, as used herein, refers to any device that is capable of administering a solution (e.g. compositions comprising components of amniotic fluid) to the respiratory airways of a patient. Inhalation devices include conventional inhalation devices, such as metered dose inhalers (MDIs), conventional nebulizers, such as jet nebulizers, and high efficiency nebulizers, such as vibrating membrane nebulizers.

Inhalation nebulizers, or atomizers, are also commonly used for the treatment of COPD and other respiratory diseases. Inhalation nebulizers deliver therapeutically effective amounts of pharmaceuticals by forming an aerosol which includes droplet sizes that can easily be inhaled. The aerosol can be used, for example, by a patient within the bounds of an inhalation therapy, whereby the therapeutically effective pharmaceutical or drug reaches the patient's respiratory tract upon inhalation. Some embodiments described herein provide for administration of a composition described herein, in powder form, with an inhalation device.

High Efficiency Nebulizer Inhalation Devices

High efficiency nebulizers are inhalation devices that are adapted to deliver a large fraction of a loaded dose to a patient. Some high efficiency nebulizers utilize microperforated membranes. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. In some embodiments, the high efficiency nebulizer contains a pulsating membrane. In some embodiments, the high efficiency nebulizer is continuously operating. In some embodiments the high efficiency nebulizer is breath activated. In some embodiments, the high efficiency nebulizer contains a vibrating microperforated membrane of tapered nozzles against a bulk liquid, and will generate a plume of droplets without the need for compressed gas. In these embodiments, a solution in the microperforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments of high efficiency nebulizers use passive nozzle membranes and separate piezoelectric transducers that are in contact with the solution. Another type of high efficiency nebulizer employs an active nozzle membrane, which uses the acoustic pressure in the nebulizer to generate very fine droplets of solution via the high frequency vibration of the nozzle membrane.

Some high efficiency nebulizers contain a resonant system. In some such high efficiency nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the high efficiency nebulizer may be made of a nickel-palladium alloy by electroforming. In some embodiments, the high efficiency nebulizer achieves lung deposition of at least about 30%, at least about 35%, at least about 40%, at least about 45%, at least about 50%, at least about 55%, at least about 60%, about 30% to about 60%, about 30% to about 55%, about 30% to about 50%, about 30% to about 40%, about 30% to about 90%, about 40% to about 80%, about 50% to about 60%, or about 60% to about 70%, based on the nominal dose of the compositions described herein administered to the patient.

Additional features of a high efficiency nebulizer with perforated membranes are disclosed in U.S. Pat. Nos. 6,962,151, 5,152,456, 5,261,601, and 5,518,179, each of which is hereby incorporated by reference in its entirety. Some embodiments of the high efficiency nebulizer contain oscillating membranes. Features of these high efficiency nebulizers are disclosed in 7,252,085; 7,059, 320; 6,983,747, each of which is hereby incorporated by reference in its entirety.

Commercial high efficiency nebulizers are available from: PARI (Germany) under the trade name eFlow®; Nektar Therapeutics (San Carlos, Calif.) (now Aerogen, Ltd.) under the trade names AeroNeb Go and AeroNebR Pro, and AeroNebR Solo, Respironics (Murrysville, Calif.) under the trade names I-NebR, Omron (Bannockburn, Ill.) under the trade name Micro-Air®, and Activaero (Germany) under the trade name Akita®. Commercial high efficiency nebulizers are also available from Aerogen (Galaway, Ireland) utilizing the OnQ K nebulizer technology.

Conventional Nebulizers

In some embodiments, compositions of the present invention may be administered with a conventional nebulizer. Conventional nebulizers include, for example jet nebulizers or ultrasonic nebulizers. Conventional nebulizers generally utilize compressors to generate compressed air, which breaks the liquid medication into small breathable droplets, which form an aerosolized (atomized) mist. In some of these embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap. In general, conventional nebulizers are characterized by relatively low efficiency in delivery of a API to lung tissue. Thus, a conventional nebulizer, such as a jet nebulizer, will be generally characterized by a respirable dose of less than 20% of the nominal dose. In some cases, the respirable dose is also referred to as the inhaled mass, which in any case is less than 20% of the nominal dose. Some conventional nebulizers are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety.

Commercial conventional nebulizers are available from: PARI (Germany) under the trade names PARI LC® and PARI-Jet®; A & H Products, Inc. (Tulsa, Okla.) under the trade name AquaTower®; Hudson RCI (Temecula, Calif.)

under the trade name AVA-NEB®; Intersurgical, Inc. (Liverpool, N.Y.) under the trade name Cirrus"; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®. Active Ingredient(s).

The efficiency of a particular inhalation device can be measured by many different ways, including an analysis of pharmacokinetic properties, measurement of lung deposition percentage, measurement of respirable dose delivery rates (RDDR), a determination of output rates, respirable fraction (RF), geometric standard deviation values (GSD), and mass median aerodynamic diameter values (MMAD) among others.

A person skilled in the art is knowledgeable of methods and systems for examining a particular inhalation device. One such system consists of a computer and a hollow cylinder in a pump with a connecting piece to which an inhalation device is to be connected. In the pump there is a piston rod, which extends out of the hollow cylinder. A linear drive unit can be activated in such a manner that one or more breathing patterns will be simulated on the connecting piece of the pump. In order to be able to carry out the evaluation of the inhalation device, the computer is connected in an advantageous configuration with a data transmitter. With the aid of the data transmitter, the computer can be connected with another computer with specific data banks, in order to exchange the data of breathing patterns. In this manner, a breathing pattern library which is as representative as possible can be very rapidly formed. U.S. Pat. No. 6,106,479 discloses this method for examining an inhalation device in more detail, and is hereby incorporated by reference in its entirety.

The assessment of therapeutic effect is known to those skilled in the art, such as pulmono legists trained to recognized the distinctions between various types of respiratory illnesses, including chronic obstructive pulmonary disease ("COPD") and asthma. Assessment of efficacy may be carried out by various methods known to the person skilled in the art, and may include both objective and subjective (patient-generated) measures of efficacy. Objective measures of efficacy can be obtained inter alia by spirometry; and subjective measures of efficacy can be obtained for example by employing one or more patient symptom questionnaires or surveys. In some embodiments, the methods and systems herein are for treatment of COPD, and thus such embodiments are discussed in further detail below. It is considered that embodiments of the methods and symptoms described herein will provide superior efficacy in treatment of COPD as compared to treatment with conventional methods.

COPD Efficacy Assessment

COPD is a progressive, chronic disease of the airways, characterized by chronic inflammation and destruction of the airways and lung parenchyma, resulting in airflow obstruction. Thus, efficacy in the treatment of COPD refers to the ability to restore airflow to the patient. In some cases, especially in older and immune-compromised patients, COPD can be further characterized by exacerbations, acute, often pathogen, or allergen-induced, degradation of airflow. There are several indicators (endpoints) of efficacy in the treatment of COPD. Some efficacy endpoints that are used in COPD studies are set forth below. It is considered that a composition comprising components of amniotic fluid as described herein will demonstrate efficacy in one or more of these tests.

Pulmonary function testing by spirometry is a useful way to assess airflow obstruction and, therefore, is a useful way to assess the efficacy of COPD treatment as well as to compare the relative merits of different COPD treatments—e.g. administration of different dosages of active pharmaceutical ingredient ("API"), administration of substantially the same dosages of API with different delivery devices, or administration of different dosages of API with different delivery devices. Forced expiratory volume in one second (FEVi) obtained from typical spirometry is commonly used as an efficacy endpoint because FEVi is a reflection of the extent of airway obstruction. Spirometry is also well-standardized, is easy to perform and provides consistent, reproducible results across different pulmonary function laboratories. Air-trapping and hyperinflation are common features in COPD, particularly in emphysematous-type, and are reflected in parameters of lung function testing, such as an elevation in the residual volume to total lung capacity ratio (RV/TLC). Hyperinflation is believed to be responsible, at least in part, for the sense of dyspnea.

Reduced capacity for exercise is a typical consequence of airflow obstruction in COPD patients, particularly because of dynamic hyperinflation occurring during exercise. Assessment of exercise capacity by treadmill or cycle ergometry combined with lung volume assessment is in some cases a tool to assess efficacy of a COPD drug. Alternative assessments of exercise capacity, such as the Six Minute Walk or Shuttle Walk, can also be used in some cases. The characteristics, including the limitations, of these tests will be known to those skilled in the art.

Outcome Measures can also be used, alone or preferably in combination with one or more objective tests, to determine efficacy of COPD therapy.

Symptom scores determined by asking patients to evaluate specific symptoms on a categorical, visual or numerical scale can be a simple way to assess efficacy of a drug based on the patient's own assessment of health status. Symptom scores can be valuable for assessing efficacy of a drug specifically aimed at relieving a symptom. In clinical programs aimed at other aspects of COPD, patient-reported symptom scores can be useful in assessing secondary effects of the therapy and may provide important additional evidence of efficacy. The characteristics, including the limitations, of these tests will be known to those skilled in the art.

Activity scales such as the Medical Research Council dyspnea score, the Borg Scale, and the Mahler Baseline Dyspnea Index/Transitional Dyspnea Index, can be used in some cases as supportive evidence of efficacy. These scales are relatively simple to administer. The characteristics, including the limitations, of these tests will be known to those skilled in the art. Health-related, quality-of-life instruments: Health-related quality-of-life instruments, such as the St. George's Respiratory Questionnaire and the Chronic Respiratory Questionnaires are designed to systematically assess many different aspects of the effect of COPD on a patient's life. These instruments can be used to assess efficacy of a drug. These instruments are multidimensional and assess various effects of the disease on a patient's life and health status. The characteristics, including the limitations, of these tests will be known to those skilled in the art.

Further information regarding testing drugs for efficacy in the treatment of COPD can be found in the United States Food and Drug Administration's guidance document entitled: "Guidance for Industry: Chronic Obstructive Pulmonary Disease: Developing Drugs for Treatment," November, 2007, which is available on the world wide web at fda.gov/cder/guidance/index.htm, incorporated by reference in its entirety herein.

According to some embodiments, a composition described herein is said to have a therapeutic effect in the treatment of COPD when it causes an increase in one or more measures of pulmonary function to a predetermined percentage above baseline. In some embodiments, the predetermined percentage above baseline is about 5%, about 10%, about 15%, about 20%, or about 25%.

Epithelial-to Mesencymal Transition (EMT)

According to some embodiments, the disclosure provides compositions and methods useful for inducing epithelial cells to undergo an EMT or useful for maintaining cells in a mesenchymal state.

According to another aspect, the disclosure features a method of inducing a cell to undergo an epithelial-to-mesenchymal transition (EMT), the method comprising steps of (a) providing the cell; and (b) contacting the cells with the composition comprising components of amniotic fluid. According to some embodiments, the cell is an epithelial cell. According to some embodiments, the cell is a progenitor cell. According to some embodiments, the cell is selected from the group consisting of hepatic progenitor (HP), hepatocyte-like cell (HLC), amniotic epithelial cell (AEC), AEC-derived cell and pluripotent stem cell (PSC)-derived cell. According to some embodiments, the cell is in an in vitro culture. According to some embodiments, the cell is isolated from the in vitro culture. According to some embodiments, the cell will be used in a transplantation procedure.

Cell-based therapies in which progenitor cells generated according to the inventive methods may be employed include the treatment of a wide variety of diseases and conditions. Examples include neurological diseases or other conditions affecting the nervous system such as Parkinson's disease, Alzheimer's disease, spinal cord injury, traumatic brain injury, and stroke. Traumatic injuries (e.g., tissue injuries, fractures), burns, heart disease (e.g., cardiomyopathy due to any of a variety of different causes), diabetes (e.g., type I diabetes involving, loss os insulin-producing beta cells), baldness, vision loss and blindness, tooth loss, osteoarthritis, tendon and ligament damage, osteochondrosis, and muscular dystrophy are other conditions that may benefit through cell-based therapies.

As known in the art, epithelial cells have are closely attached by intercellular adhesion complexes (e.g., tight junctions, adherens junctions, desmosomes, gap junctions) in their lateral membranes, typically tend to grow in clusters or sheets, express characteristic markers such as E-cadherin, a-catenin, β-catenin, and γ-catenin, and have low or absent expression of mesenchymal markers such as N-cadherin, fibronectin, and vimentin. In contrast to epithelial cells, mesenchymal cells (e.g., cells that have undergone an EMT) lack intercellular junctions and frequently exhibit an elongated shape and a greater tendency to be present as single cells rather than in clusters. They express characteristic markers such as vimentin, fibronectin, N-cadherin, and a-smooth muscle actin, typically have low or absent expression of epithelial markers such as E-cadherin, a-catenin, β-catenin, and γ-catenin, and frequently have an increased ability to migrate as compared with epithelial cells. According to some embodiments, the cells contacted with the composition comprising components of amniotic fluid have decreased expression of epithelial markers such as E-cadherin, a-catenin, β-catenin, or γ-catenin, compared to control cells not contacted with the composition comprising components of amniotic fluid, and an increased expression of vimentin, fibronectin, N-cadherin, or a-smooth muscle actin, compared to control cells not contacted with the composition comprising components of amniotic fluid. In some embodiments of the invention, epithelial cells are CD44low and CD24high while cells that have undergone an EMT are CD44high and CD24low. It will be appreciated that marker patterns of cells can be readily determined by techniques, such as cell fluorescence-activated cell sorting and immunohistochemistry, etc. As will be understood, with respect to cell markers and their expression levels, "neg" (−) refers to the absence or negligible or low level of expression of the marker, and "pos" (+) refers to robust expression. A transition of expression of a cellular marker from "neg" to "pos" represents a change from the lack of expression or low levels of expression to a high level or much higher level of expression. Thus "low" refers to a low level, "high" refers to an easily detectable and high level of expression, and the distinction between low and high expression and/or the transition from low to high expression levels, or from high to low expression levels, would be readily apparent to the practitioner. According to some embodiments, the cells contacted with the composition comprising components of amniotic fluid have an increased ability to migrate compared to control cells not contacted with the composition comprising components of amniotic fluid. e.g., in vitro, as assessed a migration assay. In some embodiments, migration is increased by at least 2, 3, 4, 5, 10, 20, 50, 100-fold or more. Cells that exhibit the characteristic properties of mesenchymal cells may be referred herein to as being in a mesenchymal state or as exhibiting a mesenchymal phenotype. In some embodiments, EMT can be assessed using histological examination.

According to another aspect, the disclosure features a method for preparing progenitor cells from epithelial cells, the method comprising the steps of: (a) providing a population of epithelial cells; and (b) inducing EMT in the population of epithelial cells by the method of any of the aspects and embodiments herein, whereby progenitor cells are generated in the population. According to some embodiments, the method further comprises isolating progenitor cells from the population after inducing EMT.

Epithelial cells (or other cells) for use in compositions and methods of the invention and/or to which methods of the invention may be applied, can be obtained from any of a wide variety of sources or, in the case of certain in vivo applications, may be present in a variety of tissues or organs. The cells may be primary cells, cells of a cell line, untransformed cells, transformed cells, genetically modified cells, or non-genetically modified cells, in various embodiments. For example, cells can be obtained from a human or other mammalian subject who may be the intended recipient of cell-based therapy, or a relative thereof, or an unrelated donor, may be obtained from discarded surgical or cellular samples from a subject, or from a propagated cell line.

According to some embodiments, an inventive method of the present disclosure is performed in vitro (i.e., outside the body of an organism, e.g., in a cell culture vessel). According to other embodiments, an inventive method is performed in vivo, e.g., by administering one or more compounds or compositions to a subject. According to some embodiments, an inventive method is performed at least in part in vitro, e.g., cells are contacted with a composition in vitro, and cells are subsequently introduced into a subject, e.g., for experimental or therapeutic purposes. Thus it should be understood that unless otherwise indicated or otherwise evident from the context, any method of the invention comprises in vitro and in vivo embodiments, and any composition of the invention can be employed in vitro or in vivo.

Kits

The invention provides a variety of kits. According to some embodiments, a kit comprises composition comprising components of amniotic fluid, alone or in combination with other agents. The composition may be packaged in individual vessels, e.g., tubes. Other agents may be packaged together in the same vessel if desired. In some embodiments, cells are provided as part of or in conjunction with the kit. Any of the kits can comprise instructions for use.

All publications and patent applications cited in this specification are herein incorporated by reference in their entirety for all purposes as if each individual publication or patent application were specifically and individually indicated to be incorporated by reference for all purposes. The publications discussed herein are provided solely for their disclosure prior to the filing date of the present application. Nothing herein is to be construed as an admission that the inventors described herein are not entitled to antedate such disclosure by virtue of prior disclosure or for any other reason.

EXAMPLES

Example 1. Optimization of Media for Cell Growth

The AECs were obtained from fresh Caesarean birth placental tissue by removing the amnion, thoroughly and repeatedly washing the tissue with phosphate-buffered saline (PBS), detaching (with 0.25% trypsin/1 mM EDTA) through 3 incubations and wash-outs, and collecting the AECs by centrifugation, or purchased from commercial vendor. The AECs were either immediately plated onto collagen-coated tissue culture dishes/flasks in propagation media (see below) or cryopreserved in knockout serum replacement containing 10% DMSO for later expansion. The AFCs were freshly obtained from full-term elective Caesarean birth donor amniotic fluid. The amniotic fluid was immediately processed by first passing through 100 m cell strainer to remove vernix/larger debris then collected by centrifugation. The resulting cell pellet was resuspended and plated for an initial expansion in AFC propagation media (see below), then subsequently expanded or cryopreserved in propagation media containing 10% DMSO for later expansion. All cell culture expansion and experiments were performed in standard 37C, 5% CO2 tissue culture incubator.

Both the AECs and AFCs were propagated in media (AEC Propagation media: DMEM/F12, 10% FBS, 1.05 mM $Ca^{2+}$, 10 ng/ml EGF, 1% penicillin/streptomycin and AFC propagation media: DMEM, 10% FBS, 30% amniotic fluid, 1% penicillin/streptomycin) and stained with the stem cell marker stage-specific antigen 4 (SSEA4) and DAPI (stains all DNA/nuclei). The images are shown in FIG. 2. Specifically, panel 2A shows AECs stained with antibody recognizing SSEA4, panel 2B shows AECs stained with DAPI, panel 2C shows AFCs stained with antibody recognizing SSEA4, and panel 2D shows AFCs stained with DAPI. The results show that the majority of propagated cells are amniotic stem cells rather than amniotic fibroblast, myoblast, or other non-stem cell types.

An experiment was performed in which maintenance of AECs' epithelial morphology was tested in three types of serum free media, as a read-out for cell homeostasis. For the experiment to test serum-free media types' effect on cell morphology, mitotically inactivated AECs were plated on collagen-coated tissue culture treated plates and allowed to attach overnight in propagation media; the following day propagation media was removed, cells were washed 3× in PBS then serum-free medias were added to each well containing AECs. The 3 different types of serum free media that were tested are listed below:

DMEM

Dulbecco's Modified Eagle's Media (DMEM; Thermo/Fisher Scientific, Waltham, Mass., USA) 1% penicillin/streptomycin (Thermo/Fisher Scientific, Waltham, Mass., USA)

SFM2:

Dulbecco's Modified Eagle's Media/F12 (DMEM/F12; Thermo/Fisher Scientific, Waltham, Mass., USA)

1% penicillin/streptomycin (Thermo/Fisher Scientific, Waltham, Mass., USA)

SFM1:

50% Iscove's Modified Dulbecco's Media (IMDM; Thermo/Fisher Scientific, Waltham, Mass., USA)

50% F12 (Thermo/Fisher Scientific, Waltham, Mass., USA)

1 mg/ml polyvinyl alcohol (Sigma-Aldrich, St. Louis, Mo., USA)

1% chemically-defined lipid concentrate (Thermo/Fisher Scientific, Waltham, Mass., USA)

450 uM monothioglycerol (Sigma-Aldrich, St. Louis, Mo., USA)

1% penicillin/streptomycin (Thermo/Fisher Scientific, Waltham, Mass., USA)

The chemically-defined lipid concentrate contains lipids arachidonic acid 2.0 mg/L, cholesterol 220 mg/L, DL-alpha-tocopherol acetate 70 mg/L, linoleic acid 10 mg/L, linolenic acid 10 mg/L, myristic acid 10 mg/L, oleic acid 10 mg/L, palmitic acid 10 mg/L, palmitoleic acid 10 mg/L, and stearic acid 10 mg/L.

FIG. 3 shows images obtained of the AECs after 0 h (propagation media removed, washed and SFM added and immediately imaged) and 24 h in each of the three types of media. Specifically, panels 3A and 3B show the results with DMEM, panels 3C and 3D show the results with SFM2, and panels 3E and 3F show the results with SFM1. A comparison of panel 3B with panels 3D and 3F shows that the cells appeared relatively more spindly, taken on more of a fibroblast-like morphology, in the DMEM media (FIG. 3B), whereas the cells incubated for 24 h in both SFM1 and SFM2 maintained their epithelial morphology. Based on these results, serum-free DMEM media was not used for the future culture of AEC cells.

Example 2. Production of Amniotic Cell Conditioned Media

Amniotic cell conditioned media (ACCM) was produced as described below.

Materials. The AECs used to produce ACCM were derived from placental tissue and propagated as described above in Example 1. The AFCs used to produce ACCM were derived from amniotic fluid and propagated as described above in Example 1.

Methods. ACCM was produced as illustrated in the flow diagram FIG. 4. Each of the AECs and AFCs were cultured for expansion using standard procedures in AEC Propagation media or AFC propagation media, respectively. Each of the two cell types were passaged twice as shown in steps 402, 404, 406, and 408. At this point, the AECs were mitotically inactivated to arrest cell division by treating with mitomycin C dissolved in propagation media at 4 ug/ml for 2 h as shown in step 410. The AECs were then immediately trypsinized, counted, and plated and the AECs were allowed to attach to the collagen-coated culture dish overnight in propagation media (step 410). The AFCs were detached, counted and plated on top of the AEC feeder layer and allowed to attach for 6 h in AEC propagation media (step 412). Following attachment, the co-culture of the AFCs and AECs ("co-AC") was thoroughly washed with PBS and serum free media (SFM) was added (step 414). The co-AC cells were cultured for 24 h, at which point the conditioned media was collected (step 416).

The amniotic cell conditioned medium (ACCM) from the co-AC cells in the method described above was analyzed as follows. FIG. 5 shows analysis of the ACCM by SDS-PAGE in which the two different types of serum free media described in Example 1 above (SFM1 and SFM2) were tested in the method at step 414. In the SDS-PAGE gel shown in FIG. 5, lg total protein was loaded in lanes (from left to right) consisting of bovine serum albumin (BSA; control to identify albumin), DMEM/F12+10% fetal bovine serum (D/F12+S), unconditioned serum-free media 1 (SFM1; unc), co-AC conditioned SFM1(SFM1; co-AC), AEC conditioned SFM1 (SFM1; AEC), AFC conditioned SFM1 (SFM1; AFC), unconditioned serum-free media 2 (SFM2; unc), co-AC conditioned SFM2 (SFM2; co-AC), AEC conditioned SFM2 (SFM2; AEC), and AFC conditioned SFM2 (SFM2; AFC), and electrophoresed on 10% SDS-polyacrylamide gel then silver stained and scanned on a Li-Cor Odyssey CLx. The signal intensity calculated per lane is shown as "signal/microgram" at the bottom of the gel determined by generating a region of interest consisting of each lane and determining signal counts within using ImageStudio software program. Molecular weight in kilodaltons (kDa) is shown on the left; ND denotes no signal detected above background; all conditioned medias analyzed were generated by 24 h culture and unconditioned medias by 24 h incubation in a well of the same culture plate but minus cells.

As can be seen in FIG. 5, the co-culture of the AECs and AFCs (co-AC) in the defined media, SFM1, resulted in increased total protein secretion and increased protein complexity (e.g., the same amount of total protein (1 ag) is added in each lane, but the co-AC conditioned media shows both different bands present and an increased signal intensity relative to AECs or AFCs alone). Surprisingly, the co-culture of the AECs and AFCs in the SFM2 media shows no apparent protein secretion at all compared to unconditioned media. These data illustrate a synergistic effect of the co-culture of the AECs and AFCs in the SFM1 media that can yield a conditioned media comprising both increased protein concentration and complexity.

The amniotic cell conditioned medium (ACCM) from the co-culture of the AECs and AFCs in the SFM1 media in the method described above was further analyzed by Bradford assay and LC-MS/MS and the data are shown in FIG. 6. Unconditioned SFM1 media (SFM1), the co-AC conditioned SFM1 (co-AC), the AEC conditioned SFM1 (AEC), and the AFC conditioned SFM1 (AFC) were measured for total protein concentration using the Bradford method or the proteome analyzed by liquid chromatography-tandem mass spectrometry (LC-MS/MS) to determine unique proteins present in each sample and the percent of proteins per sample relative to all proteins identified in each of the 4 groups assayed. As can be seen in FIG. 6, the co-culture of the AECs and AFCs in the SFM1 media according to the method described above resulted in the highest total protein concentration by Bradford assay. Using the LC-MS/MS method a higher number of proteins (by identity) is observed compared to AECs or AFCs alone. The viable cell results from the trypan blue exclusion assay show that the AFC alone cell count is the same as the co-AC cell count, indicating that the higher protein concentration and increased number of distinct protein identities results from the same number of cells per well. These data show the synergistic effect of the co-culture of the AECs and AFCs in the SFM1 media that can yield a conditioned media comprising both increased protein concentration and complexity.

FIG. 7 is a Venn diagram of the LC-MS/MS data shown in FIG. 6 showing that the co-culture of the AECs and AFCs in the SFM1 media yields 84 unique proteins by identity not observed in either the AEC- or AFC alone conditioned SFM1. This result illustrates the synergistic effect of the co-culture of the AECs and AFCs in the SFM1 media that can yield a conditioned media with increased protein complexity.

FIG. 8 shows, by quantitative analysis, the number and percentage of proteins identified by LC-MS/MS in the conditioned SFM1 from the co-culture of the AECs and AFCs according to the method described above. The data in FIG. 8 show that the co-culture of the AECs and AFCs yielded quantitatively higher levels of proteins than in either AECs only, AFCs only, or the sum of AECs and AFCs only. The first row in FIG. 8 is normalized total spectral counts for the co-culture of the AECs and AFCs in SFM1 that is greater than zero (co-AC>0); the second row in FIG. 8 is co-AC after subtracting the background contribution of unconditioned media (co-AC>BG), the third row in FIG. 8 is co-AC protein levels after subtracting background plus AEC alone-conditioned SFM1 protein levels (co-AC>(BG+AEC)), the fourth row in FIG. 8 is co-AC protein levels after subtracting background plus AFC alone-conditioned SFM1 protein levels (co-AC>(BG+AFC)), and the fifth row in FIG. 8 is co-AC protein levels after subtracting background plus AEC alone-conditioned SFM1 plus AFC alone-conditioned SFM1 protein levels (co-AC>(BG+AEC+AFC)). The results in FIG. 8 show that the quantity of 225 of the identified proteins (27.3% of the total) are present at a higher level in the conditioned media from co-culture of AECs and AFCs than the additive level of AEC alone-conditioned SFM1 plus AFC alone-conditioned SFM1. These data illustrate, using a quantitative analysis of the proteome, the synergistic effect of the co-culture of the AECs and AFCs in the SFM1 media that can yield a conditioned media with increased protein concentration and complexity, and rule-out a simply additive effect of AFC and AEC conditioning alone.

Gene ontology (GO) term analysis was performed to identify significantly enriched biological pathways represented within the proteome of conditioned SFM1 from the co-culture of the AECs and AFCs according to the method described above. The results are shown in FIG. 9. LC-MS/MS data from the conditioned SFM1 was compared to unconditioned SFM1 LC-MS/MS data (input as background data set) to derive enriched ($p \leq 0.05$) GO terms. Selected GO terms are shown on the Y-axis and p-values are plotted on the X-axis as leX with X being the value shown on the X-axis.

FIG. 10 shows a Western blot comparing protein presence and abundance between amniotic fluid (AF) and coACCM. Protein level was determined by Bradford method relative to bovine serum albumin and 7 micrograms total protein was loaded per well on 8% SDS-PAGE for AF and ~1 microgram total protein loaded for coACCM, each in biological triplicate. Nitrocellulose membranes were probed with the indicated primary antibody, then visualized on Odyssey CLx using infrared imaging of infrared-conjugated secondary antibodies. Mean protein signal per microgram of protein loaded is shown below, +/− standard deviation (*P<0.01 by student's t-test). These results demonstrate that the composition of AF vs. coACCM is markedly different Example 3. Effects of ACCM on Liver Cell-based assays are performed to test ACCM in promoting liver cell homeostasis. Assays are performed to test hepatocyte and cholangiocyte growth in ACCM vs. unconditioned media. Assays are performed to determine the role of ACCM in the prevention of cell death induced by reactive oxygen species (ROS) by culturing cells in ACCM as compared to cells cultured in unconditioned media. The capability of ACCM to reduce stellate cell activation (induces liver fibrosis long-term) is tested by comparing cells cultured in ACCM to those cultured in unconditioned media.

Example 4. Effects of ACCM in Promotion of Wound Healing In Vitro

Myocytes from neonatal rat hearts are grown until forming a near-confluent monolayer on a tissue culture dish according to standard protocols. The cultures are subsequently allowed to culture for a further 5 days in the presence of the compositions as described herein (the treated group), or in the presence of an untreated control with no culture medium.

Culture media is changed every 24 hours during the experiment. Gap junction formation is compared between the treated group and the untreated control.

NIH-3T3 cells are grown over 2-3 days until forming a near-confluent monolayer on a tissue culture dish according to standard protocols and the monolayer is then pre-treated with the compositions described herein, and "scratch-injured" with a p200 pipette tip. The "scratch injury" is subsequently allowed to repopulate for 24 hours in the presence of the compositions described herein, in in the presence of untreated control. The repopulation of the "scratch injury", which occurs in part via migration of the transformed cells crawling into the "scratch injury" area is determined by microscopic observation. Further, proliferating cell nuclear antigen (PCNA) immunolabeling of cells in the "scatch injury" or at the injury edge can be used to determine the effect of the compositions described herein on cell proliferation in the wound.

FIG. 11 shows the results of ScratchTest experiments. FIG. 11A shows brightfield microscopy (20× objective) showing representative images of C2C12 myoblasts during scratch test wound healing assay at time (hours) 0, 12, 24, and 36 incubated with unconditioned serum-free media (uncSFM), unconditioned serum-free media+10% amniotic fluid (uncSFM+AF), co-cultured amniotic cell conditioned media (co-ACCM), or complete media (ComplM; DMEM+ 10% FBS). Dotted lines outline areas not occupied by cells; scale bar denotes 50 μm. FIG. 11B shows quantitation of scratch area (in pixels) in conditions described in FIG. 11A. Area was calculated using ImageJ software and three independent replicates for each condition and timepoint were measured. Each datapoint shows the mean area value in pixels, +/− standard deviation (*P≤0.05 by student's t-test, relative to uncSFM; additionally all P for co-ACCM were ≤0.005 relative to uncSFM+AF, except for 0 h timepoint, by student's t-test). These results demonstrate that coACCM elicits a significantly different biological effect/cell phenotype than the "natural product" (AF)

FIG. 12A shows the results of ScratchTest experiments. FIG. 12A shows brightfield microscopy (20× objective) showing representative images of MMM fibroblasts during scratch test wound healing assay at time (hours) 0, 12, 24, and 36 incubated with unconditioned serum-free media (uncSFM), unconditioned serum-free media+10% amniotic fluid (uncSFM+AF), amniotic cell co-culture conditioned media (co-ACCM), or complete media (ComplM; DMEM+ 10% FBS). Dotted lines outline area not occupied by cells; scale bar denotes 50 μm. FIG. 12B shows quantitation of scratch area (in pixels) in conditions described in A. Area was calculated using ImageJ software and three independent replicates for each condition and timepoint were measured. Each datapoint shows the mean area value in pixels, +/− standard deviation (*P≤0.005 or **P≤0.001 by student's t-test, relative to uncSFM; additionally all P for co-ACCM were ≤0.001 relative to uncSFM+AF, except for 0 h timepoint, by student's t-test). This results indicates that coACCM elicits a significantly different biological effect/cell phenotype than the "natural product" (AF)

Example 5. Effect of coACCM on EMT

EMT endows cells with migratory and invasive properties, induces stem cell properties, prevents apoptosis and senescence, and contributes to immunosuppression. Thus, the mesenchymal state is associated with the capacity of cells to migrate to distant organs and maintain stemness, allowing their subsequent differentiation into multiple cell types during development and the initiation of metastasis. The effects of coACCM on EMT were examined.

FIG. 13A shows results of qPCR for various epithelial-to-mesenchymal transition (EMT) genes. Following 72 h incubation in respective media type for scratch test assays, RNA was extracted from C2C12 myoblasts, reverse transcribed, then mRNA abundances were measured to determine level relative to hydroxymethylbilane synthase (housekeeping gene). Left panel shows the relative abundances of E-Cadherin (E-Cad) and N-Cadherin (N-Cad), and right panel shows the relative abundance of fibronectin. Ordinary one-way ANOVA was used to measure statistically significant differences, with ns=not significant, *P≤0.05, P≤0.01, *P≤0.001, ****P≤0.0001 denoting results. FIG. 13B shows results from the same experiments performed in FIG. 13A, but performed with MMM cells. EMT biomarkers are an increase in N-Cad with concomitant decrease in E-Cad, and an up-regulation of fibronectin. Mesenchymal-to-epithelial transition (MET) is measured in the opposite. Thus, these results show that coACCM appears to activate EMT, while AF activates MET. Additionally, this indicates coACCM elicits a different biological effect/molecular phenotype than the "natural product" (AF). FIG. 14A shows the results of qPCR for Tgfb-Col-Acta2. Following 72 h incubation in respective media type for scratch test assays, RNA was extracted from C2C12 myoblasts (left column) or MMM fibroblasts (right column), reverse transcribed, then mRNA abundances were measured to determine level relative to hydroxymethylbilane synthase (housekeeping gene). Top row shows the relative abundances of TGF-beta receptor1 (Tgfbr1) and bottom TGF-beta receptor2 (Tgfbr2). Ordinary one-way ANOVA was used to measure statistically significant differences, with ns=not significant, *P≤0.05, P≤0.01, *P≤0.001, ****P≤0.0001 denoting results. FIG. 14B shows results from the same experiments performed in FIG. 14A, where type I collagen (Col1a1; top row) or smooth muscle actin (Acta2; bottom row) were measured. Tgf-beta signaling activity can be measured by an up-regulation of Tgfbr1 or Tgfbr2 (Kleef and Korc JBC 1998). Thus, without being bound by theory, these results suggest that EMT may be induced by coACCM through this pathway. Increase in Tgfbr1 indicates enhanced cooperative signaling, while increased Tgfbr2 direct ligand binding. Increased Acta2 indicates an increase in fibrosis, which is usually associated with poor healing outcomes and excessive scarring. Increased Col1a1 can be beneficial in cosmetic applications (increased collagen production), and can indicate ECM remodeling/cell activation in wound healing; it may be beneficial to downregulate collagen in late wound healing events, though. Additionally, this indicates coACCM elicits a different biological effect/molecular phenotype than the "natural product" (AF).

FIG. 15A shows indirect immunofluorescence imaging of C2C12 cells incubated with uncSFM, uncSFM+AF, coACCM, or complM for 24 h, and then stained with anti-Vimentin antibody, phalloidin, and DAPI. Representative images shown collected using 20× objective on Opera Phenix High Content Screening Microscope (Perkin Elmer); scale bar denotes 100 μm and inset region shows zoomed-in image with arrowheads indicating perinuclear vimentin localization. In FIG. 15B, using images collected as described above, the $\log_2$ fold-change in vimentin relative to phalloidin was calculated for each cell recorded (see cell number "n" below x-axis labels) and its distribution plotted using the Tukey box plot method. P-values were calculated using the Mann-Whitney non-parametric test for statistical significance. This is both a qualitative (A) and quantitative (B) assessment of vimentin (an EMT biomarker) protein. Increased total vimentin is a well-established indicator of EMT, and perinuclear aggregation/localization of vimentin is correlated with microtubule inhibition/inactivation (Goldman 1971), decreased cell motility (Mendez et al 2010), and reduced organelle movement (Chang et al 2009). Additionally, this indicates coACCM elicits a different biological effect/molecular phenotype than the "natural product" (AF).

Example 6. Exosome-Depleted coACCM Appears to Repress EMT and Modulate Healing-Related Gene Expression Relative to coACCM FIG. 16 shows a size distribution histogram of extracellular vesicles. The size and concentration of extracellular vesicles from coACCM and AF were measured using the ZetaSizer PMX-120 (Malvern), then the number of particles measure per milliliter (y-axis) were plotted relative to the size of the vesicles (x-axis). Dashed vertical lines demarcate sizes of 50-200 nm. Data were analyzed using the Spearman correlation and r value and P value are shown in legend. The size range of ~50-200 nm is generally recognized to be the size range of "exosomes". These results indicate coACCM is considerably different from the natural product (AF) by composition.

FIG. 17 shows the results of Western blot analysis of exosome markers and TGFBI in total coACCM (total), crude exosomal fraction from ExoQuick TC-ULTRA kit (SBI Biosciences) initial centrifugation step (exo-crude), purified exosomes eluted from column on final purification step from ExoQuick TC-ULTRA kit (SBI Biosciences; exo-pure), and exosome-depleted coACCM (exo(−)). Blots were probed with antibodies directed toward CD63 (top), CD9 (middle), and TGFBI (bottom), with molecular weight (MW) markers indicated in kilodaltons (kDa) at right. CD63 and CD9 are used as exosome biomarkers; TGFBI is included to show it likely is exosome-bound.

FIG. 18A shows brightfield microscopy (20× objective) showing representative images of C2C12 myoblasts during scratch test wound healing assay at time (hours) 0, 12, and 24 incubated with uncSFM, coACCM, uncSFM plus an equal quantity of exosomes derived from coACCM as in an equal volume to total coACCM (uncSFM+coACCMexos), or coACCM depleted of exosomes (exo(−) coACCM). Dotted lines outline area not occupied by cells; scale bar denotes 50 μm. FIG. 18B shows quantitation of scratch area displayed as percent area relative to measured scratch area at time zero in conditions described in A. Area was calculated using ImageJ software and three independent replicates for each condition and timepoint were measured. Each datapoint shows the mean relative percent area, +/− standard deviation (*$P \leq 0.05$ by student's t-test, $P \leq 0.01$, *$P \leq 0.001$ relative to uncSFM). FIG. 19 shows the results of RT-qPCR analysis from RNA extracted from C2C12 myoblasts from scratch test analysis incubated for 24 h with uncSFM, coACCM, uncSFM plus an equal number of coACCM exosomes as that measure from total coACCM (uncSFM+coACCMexos), or exosome-depleted coACCM (exo(−)coACCM). N-Caherin/E-Cadherin ddCt ratio, Snail (Snail), Type I Collagen (Col1a1), and Smooth muscle actin (Acta2) abundance was measured as ddCt relative to Hydroxymethylbilane synthast (Hmbs; loading control). The N-Cad/E-Cad ratio is to measure EMT, but the ratio measurement precludes validity for measuring statistical significance, so none was reported/measured. Snail is a transcription factor that induces EMT. Col1a1 and Acta2 are "healing related" biomarkers. These results demonstrate that exosome-depleted coACCM appears to repress EMT and modulate healing-related gene expression relative to coACCM.

Example 7. Effects of ACCM in Promotion of Wound Healing In Vivo

Wound healing can be assessed using a model with full thickness excisional wounds of a pre-determined diameter on 8 week old mice. Followed by immunohistochemistry and histology, with RT-PCR analysis of gene expression.

Skin wounds repair by a combination of re-epithelializing action and, connective tissue contraction followed by an angiogenic response which leads to a dense network of blood vessels in the wound granulation tissue (Grose, R. and Werner, S. (2004). Wound-healing studies in transgenic and knockout mice. Mol Biotechnol 28, 147-66.). A robust inflammatory response commences soon after any tissue damage. This both protects the wound from microbial infection and produces many kinds of bioactive substances that act on the host cells at the wound site. A variety of inflammatory cells migrate into the wound fulfilling several different functions. Neutrophils are the earliest leukocytes to be recruited to the wound and their main role is to defend the host from invasion by microbes, which they do by releasing toxic free oxygen radicals and secreting proinflammatory cytokines. Subsequently, macrophages clear away spent neutrophils and other cell and extracellular matrix debris at the wound site. Macrophages are also the major producers of cytokines, chemokines and growth factors that will direct subsequent cell and tissue migration of the repair response. Whilst many of the signals regulating the inflammation and tissue repair process are clearly diffusible and operate over long distances, local cell-cell communication via cell adhesion molecules and cell-cell junctions appears also to play a significant role.

One junctional link between cells which may play a significant regulatory role is the gap junction which is a hexameric channel formed of proteins from the connexin family. Gap junctions are reported to be expressed by almost all cells in the body (Wei, C. J., Xu, X. and Lo, C. W. (2004). Annu Rev Cell Dev Biol 20, 811-38.) and have been reported to mediate changes in cell migration. The level of connexin 43 (Cx43) protein at the epidermal wound edge has been reported to naturally decreases over 24-48 hours. Downregulating Cx43 protein levels by application of antisense oligodeoxynucleotides (asODN) to skin wound and burn injury sites has been reported to lead to significantly accelerated healing compared with control sense oligodeoxynucleotides (sODN) treated wounds (Qiu, C, Coutinho, P., Frank, S., Franke, S., Law, L. Y., Martin, P., Green, C R. and Becker, D. L. (2003). Targeting connexin 43 expression accelerates the rate of wound repair. Curr Biol 13, 1697-703; Coutinho, P., Qiu, C, Frank, S., Wang, C M., Brown, T., Green, C R. and Becker, D. L. (2005). Limiting burn extension by transient inhibition of connexin 43 expression at the site of injury. Br J Plast Surg 58, 658-67).

Experiments can be performed to determine, e.g., the downregulation of Cx43 protein at a wound site, and the change in keratinocyte proliferation and migration, and in the rate at which fibroblasts migrate into the wound and lay down collagen matrix. An increase in keratinocyte proliferation and migration, and in the rate at which fibroblasts migrate into the wound and lay down collagen matrix is expected following treatment with the pharmaceutical compositions described herein.

Wound Model and ODN Treatment

Male, 8 week old, ICR mice are used in the following experiments. Mice are anaesthetized by halothane inhalation. Four full-thickness excisional wounds of a predetermined diameter (e.g. 6 mm) are made on the shaved back on either side of the dorsal midline with a biopsy punch. To each pair of wounds a topical application of the pharmaceutical composition of the present invention, at a range of concentrations, is made to one wound, and an identical application of control composition is made to the other. Each wound region is digitally photographed at pre-determined time intervals, and the areas of the wounds are calculated. All wound areas are expressed as percentages of the initial wound areas. In some series of experiments, wounds and their surrounding area, including the scab and epithelial margins, are harvested with an 8 mm biopsy punch (Kai Industries) at the indicated time intervals after mice were killed with an overdose of chloroform. A minimum of eight mice are used for each time point examined.

Histology and Immunostaining

Wound tissues are fixed in 4% formaldehyde buffered with PBS, and embedded in paraffin. Sections (6 µm thick) were subjected to hematoxylin and eosin staining or immunostaining. Measurement of granulation tissue area in H&E is performed. For immunohistochemistry, deparaffinized sections are treated with endogenous peroxidase blocking reagent (Dako Cytomation A/S) and proteinase K (Dako Cytomation A/S) for 20 minutes and 6 minutes at room temperature, respectively. They are then incubated with rabbit antimyeloperoxidase (MPO) polyclonal antibody (NeoMarkers) diluted 1:200, rat anti-mouse F4/80 monoclonal antibody (mAb) (Abcom Limited) diluted 1:400 or rat antimouse CD31 (platelet endothelial cell adhesion molecule 1, PECAM-I) mAb (PharMingen) or rabbit anti-mouse TGF-/31 polyclonal antibody (Santa Cruz Biotechnology, Inc) both diluted 1:200 overnight at 40 C after blocking with 15% skimmed milk for 1 hour at room temperature. In addition, some sections were reacted with phalloidin-tetramethylrhodamine B isothiocyanate (Sigma-Aldrich) diluted 1:500 for 1 hour at room temperature. The antibodies are appropriately diluted in Antibody Diluent with Background Reducing Components (Dako Cytomation A/S). The sections reacted with anti-MPO antibody and anti TGF-b1 antibody were stained with EnVision+™ (Dako Cytomation A/S) to enhance the signal, according to the manufacturer's instructions. The sections that had been reacted with anti-F4/80 and anti-CD31 antibodies were incubated with biotinylated rabbit anti-rat immunoglobulin (Dako Cytomation A/S) diluted 1:200 for 1 hour at 370 C. The signal was then enhanced using the Catalyzed Signal Amplification System® (Dako Cytomation A/S) according to the manufacturer's instructions. Thereafter, counterstaining is performed with methyl green (Dako Cytomation A/S) followed by MPO, TGF-/31, F4/80, and CD31 staining or 4',6-diamidino-2-phenylindole (DAPI) followed by phalloidin staining.

Immunostaining for connexin 43, blood vessels or a smooth muscle actin is carried out on cryostat sections of wounds. Sections were fixed in acetone at 40 C for 5 minutes prior to blocking for 45 minutes. Incubation in primary antibody is for one hour at the following dilutions: rabbit anti-Cx43 (Sigma) 1:3,000; isoLectin B_FITC 1:2000; von Willebrand Factor (rabbit Dako) 1:400; anti-α smooth muscle actin (Sigma) 1:400 at room temperature. Sections were washed for 3×5 minutes in PBS before a one hour incubation in anti-rabbit-FITC secondary antibody (Dako) 1:200 at room temperature. Washing 3×5 minutes in PBS, in some cases with 1 µM bis-benzimide (Sigma) in the first wash as a nuclear counter stain, and mounted in Citifluor (Citifluor, London, UK). Sections were imaged by confocal microscopy with all parameters kept constant to allow direct comparison of digital images.

TUNEL Staining

Wound tissues are fixed in 4% formaldehyde buffered with PBS, and embedded in paraffin and sectioned. Deparaffinized sections are treated with proteinase K (Dako Cytomation A/S) for 5 minutes at room temperature. They are then stained using the In Situ Cell Death Detection Kit (Roche) according to the manufacturer's instructions. Thereafter, counterstaining was performed with 4',6-diamidino-2-phenylindole (DAPI). TUNEL stained section were imaged and positive cells are counted in the granulation tissue in three random fields, in the two sides and center of each wound (each field was 0.332 mm2).

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present Examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

What is claimed is:

1. A method for making a composition comprising components of amniotic fluid, the method comprising: (a) transferring amniotic epithelial cells (AECs) and amniotic fluid cells (AFCs) to a cell culture system and co-culturing the AECs and AFCs in a defined serum free medium consisting of a base medium, wherein the base medium is 50% Iscove's Modified Dulbecco's Medium (IMDM), 50% F12 Medium; 450 µM monothioglycerol, 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alphatocopherol acetate, 10 mg/L linoleicacid, 10 mg/L linolenicacid, 10 mg/L myristic acid, 10 mg/L oleic acid, 10 mg/L palmitic acid, 10 mg/L palmitoleic acid, and 10 mg/L stearic acid; and wherein a synergistic effect of the co-culture of the AECs and AFCs in the base medium results in both increased protein concentration and increased protein complexity when compared to a culture of AECs or AFCs alone; (b) separating the AECs and AF Cs from the culture medium to obtain a conditioned supernatant; (c) removing large molecules and other cell debris from the conditioned supernatant; and (d) ensuring the sterility of the conditioned supernatant, wherein the conditioned supernatant is the composition comprising components of amniotic fluid.

2. The method of claim 1, wherein
  (a) the AECs are attached to a surface of the culture system and the AFCs are deposited on top of the AECs; or
  (b) the AECs are mitotically inactivated prior to transferring to the cell culture system; or
  c the AECs and AFCs are expanded prior to transferring to the cell culture system by passaging the AECs and AFCs one, two or three times; or
  d the AECs and AFCs are derived from a mammalian tissue without having been previously frozen.

3. The method of claim 2, wherein the mammalian tissue is a human tissue.

4. A method for making a composition comprising components of amniotic fluid, the method comprising: (a) transferring amniotic fluid cells (AFCs) and amniotic epithelial cells (AECs) to a cell culture system and co-culturing the AFCs and AECs in a defined serum free medium consisting of a base medium, wherein the base medium is 50% Iscove's Modified Dulbecco's Medium (IMDM), 50% F12 Medium; 450 µM monothioglycerol, 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alphatocopherol acetate, 10 mg/L linoleicacid, 10 mg/L linolenicacid, 10 mg/L myristic acid, 10 mg/L oleic acid, 10 mg/L palmitic acid, 10 mg/L palmitoleic acid, and 10 mg/L stearic acid; and wherein the AECs and AFCs are co-cultured until a pre-determined target protein concentration in the culture medium is reached, and wherein a synergistic effect of the co-culture of the AECs and AFCs in the base medium results in both increased protein concentration and increased protein complexity when compared to a culture of AECs or AFCs alone; (b) separating the AECs and AFCs from the culture medium to obtain a conditioned supernatant; (c) removing large molecules and other cell debris from the conditioned supernatant; and (d) ensuring the sterility of the conditioned supernatant, wherein the conditioned supernatant is the composition comprising components of amniotic fluid.

5. The method of claim 4, wherein
  (a) the AECs and AFCs are derived from a mammalian tissue without having been previously frozen; or
  (b) wherein the mammalian tissue is a human tissue.

6. A composition comprising components of amniotic fluid, wherein the composition is produced by a process comprising: (a) transferring amniotic epithelial cells (AECs) and amniotic fluid cells (AFCs) to a cell culture system and co-culturing the AECs and AFCs in a defined serum free medium consisting of a base medium; wherein the base medium is 50% Iscove's Modified Dulbecco's Medium (IMDM), 50% F12 Medium; 450 µM monothioglycerol, 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alpha-tocopherol acetate, 10 mg/L linoleic acid, 10 mg/L linolenic acid, 10 mg/L myristic acid, 10 mg/L oleic acid, 10 mg/L palmitic acid, 10 mg/L palmitoleic acid, and 10 mg/L stearic acid; and wherein a synergistic effect of the co-culture of the AECs and AF Cs in the base medium results in both increased protein concentration and increased protein complexity when compared to a culture of AECs or AFCs alone; (b) separating the AECs and AF Cs from the culture medium to obtain a conditioned supernatant; (c) removing large molecules and other cell debris from the conditioned supernatant; and (d) ensuring the sterility of the conditioned supernatant, wherein the sterile conditioned supernatant is the composition comprising components of amniotic fluid.

7. The composition produced by the process of claim 6, wherein
  (a) the AECs are attached to a surface of the cell culture system and the AFCs are deposited on top of the AECs; or
  (b) the AECs are mitotically inactivated prior to transferring to the cell culture system; or
  (c) the AECs and AFCs are expanded prior to transferring to the cell culture system by passaging the AECs and AFCs one, two or three or more times; or
  (d) the AECs and AFCs are derived from a mammalian tissue without having been previously frozen; or
  (e) the components of amniotic fluid are present in concentrations effective to induce a cell population to undergo an epithelial-to-mesenchymal transition (EMT).

8. The composition of claim 7, wherein the mammalian tissue is a human tissue.

9. A method for preservation of an organ, the method comprising surrounding the organ in a composition comprising components of amniotic fluid according to claim 6, wherein the organ is preserved in the composition.

10. The method of claim 9, wherein the organ is useful as a transplant organ.

11. The composition produced by the process of claim 7, wherein the cell population is an epithelial cell population or a progenitor cell population.

* * * * *